United States Patent
Körner et al.

(10) Patent No.: US 11,566,998 B2
(45) Date of Patent: Jan. 31, 2023

(54) METHOD AND SHEAR-INVARIANT MICHELSON-TYPE INTERFEROMETER FOR SINGLE SHOT IMAGING FT-SPECTROSCOPY

(71) Applicant: Universitat Stuttgart, Stuttgart (DE)

(72) Inventors: Klaus Körner, Berlin (DE); Alois M. Herkommer, Aalen (DE)

(73) Assignee: Universität Stuttgart, Stuttgart (DE)

( * ) Notice: Subject to any disclaimer, the term of this patent is extended or adjusted under 35 U.S.C. 154(b) by 0 days.

(21) Appl. No.: 17/217,924

(22) Filed: Mar. 30, 2021

(65) Prior Publication Data
US 2021/0310937 A1    Oct. 7, 2021

(30) Foreign Application Priority Data

Mar. 31, 2020 (EP) ..................................... 20167240

(51) Int. Cl.
| | |
|---|---|
| *G01N 21/31* | (2006.01) |
| *A61B 5/00* | (2006.01) |
| *G01N 21/45* | (2006.01) |

(52) U.S. Cl.
CPC ........... *G01N 21/31* (2013.01); *A61B 5/7257* (2013.01); *G01N 21/45* (2013.01); *A61B 5/0059* (2013.01); *G01N 2201/0636* (2013.01)

(58) Field of Classification Search
CPC ............. G01J 2003/2826; G01J 3/2823; G01J 9/0215
See application file for complete search history.

(56) References Cited

U.S. PATENT DOCUMENTS

| | | |
|---|---|---|
| 1,565,533 A | 12/1925 | Twyman et al. |
| 3,684,379 A | 8/1972 | Girard |

(Continued)

FOREIGN PATENT DOCUMENTS

| | | |
|---|---|---|
| CN | 106338342 A | 1/2017 |
| DE | 689 06 154 T2 | 8/1993 |

(Continued)

OTHER PUBLICATIONS

Gao, P., et al., "Parallel two-step phase-shifting point-diffraction interferometry for microscopy based on a pair of cube beamsplitters", Optics Express, vol. 19, No. 3, pp. 1-6 (Jan. 31, 2011).
Hirai, A., et al., "Application of Multiple-Image Fourier Transform Spectral Imaging to Measurement of Fast Phenomena", Optical Review, vol. 1, No. 2, pp. 205-207 (1994).

(Continued)

*Primary Examiner* — Maurice C Smith
(74) *Attorney, Agent, or Firm* — Shook, Hardy & Bacon, LLP

(57) ABSTRACT

Fourier Transformation Spectrometer, FT Spectrometer, comprising: Michelson-Type Interferometer (601, 602, 603, 604, 605, 606, 607, 608, 609) comprising: at least one beam splitter unit designed to split an incident light beam (EB) of a spatially expanded object into a first partial beam (TB1) and a second partial beam (TB2); and for at least partially overlaying the first partial beam (TB1) and the second partial beam (TB2) with a lateral shear (s); a first beam deflection unit designed to deflect the first partial beam (TB1) at least once; a second beam deflection unit designed to deflect the second partial beam (TB2) at least once; wherein at least one among the first beam deflection unit and the second beam deflection unit represents a (2n+1) periscope group with (2n+1) mirror surfaces, and all (2n+1) mirror surfaces are arranged vertically in relation to a common reference plane, in order to respectively deflect the (Continued)

first partial beam (TB1) and/or the second partial beam (TB2) (2n+1) times, and wherein the (2n+1)-fold deflection generates the lateral shear (s) between the first partial beam (TB1) and the second partial beam (TB2), and wherein n is a natural number ≥1.

16 Claims, 18 Drawing Sheets

(56) References Cited

U.S. PATENT DOCUMENTS

| | | | |
|---|---|---|---|
| 4,523,846 | A | 6/1985 | Breckinridge et al. |
| 4,976,542 | A | 12/1990 | Smith |
| 5,131,747 | A | 7/1992 | Cerutti-Maori et al. |
| 5,539,517 | A | 7/1996 | Cabib et al. |
| 5,541,728 | A | 7/1996 | Dierking |
| 5,777,736 | A | 7/1998 | Horton |
| 6,930,781 | B2 | 8/2005 | Agladze et al. |
| 8,934,104 | B2 | 1/2015 | Koerner et al. |
| 2019/0162520 | A1 | 5/2019 | Shaked et al. |

FOREIGN PATENT DOCUMENTS

| | | | | |
|---|---|---|---|---|
| DE | 10 2010 006 239 B3 | | 3/2011 | |
| EP | 2 526 373 B1 | | 12/2013 | |
| EP | 2843360 A1 | * | 3/2015 | ........... A61B 5/0066 |
| WO | 2013/140396 A1 | | 9/2013 | |
| WO | WO-2014067651 A1 | * | 5/2014 | ......... G01B 9/02061 |

OTHER PUBLICATIONS

Kelsall, D., "Optical Frequency Response Characteristics in the presence of Spherical Aberration measured by an automatically recording Interferometric Instrument", DepartJnent of Physics, pp. 465-479 (1958).

Kudenov, M. W., and Dereniak, E. L., "Compact Snapshot Real-Time Imaging Spectrometer", Electro-Optical Remote Sensing, Proc. of SPIE, pp. 1-12 (2011).

Liu, C., et al., "Large field-of-view Fourier transform imaging spectrometer using dual-channel stitching", Optics Express, vol. 24, No. 25, pp. 28473-28490 (Dec. 12, 2016).

Malacara, D., "Optical Shop Testing", Second Edition, John Wiley & Sons, Inc., pp. 3 (1992).

Okamoto, T., et al., "Fourier Transform Spectrometer With A Self-Scanning Photodiode Array", Applied Optics, vol. 23, No. 2, pp. 269-273 (Jan. 15, 1984).

Wu, Y., et al., "Global estimates of lunar iron and titanium contents from the Chang' E-1 IIM data", Journal Of Geophysical Research, vol. 117, E02001, pp. 1-23 (2012).

* cited by examiner

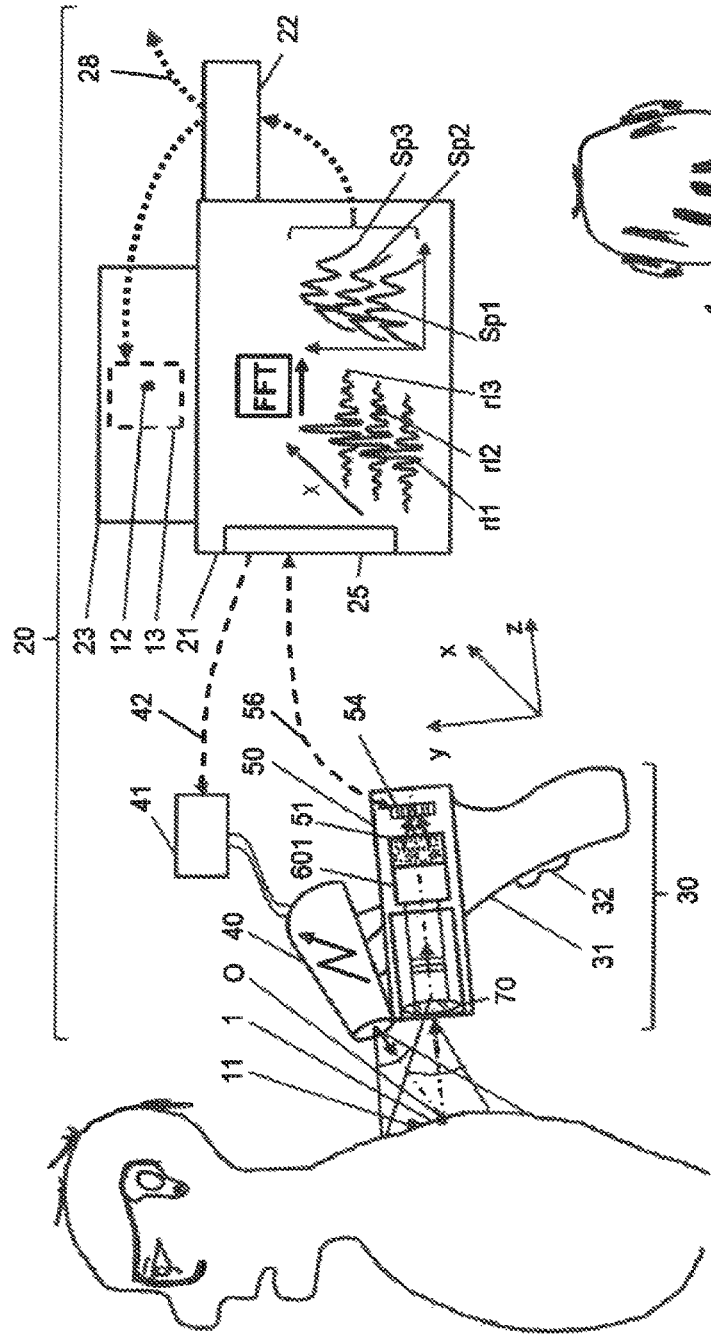
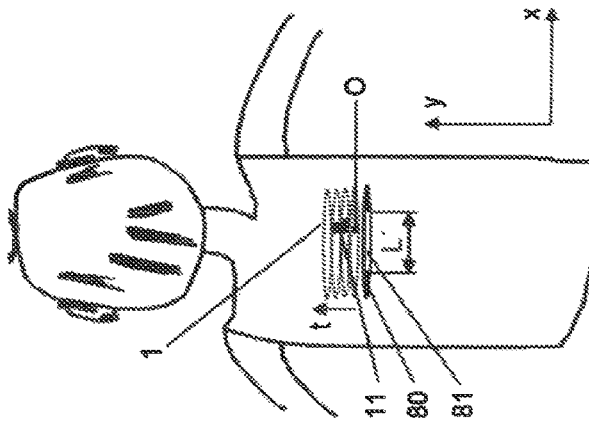
Figure 1
Figure 2

METHOD AND SHEAR-INVARIANT MICHELSON-TYPE INTERFEROMETER FOR SINGLE SHOT IMAGING FT-SPECTROSCOPY

This U.S. Non-Provisional Patent application claims priority to European Patent Application No. 20167240.9, filed Mar. 31, 2020, titled "Verfahren and Shear-invariantes Michelsontyp-Interferometer zur Single-Shot-Imaging-FT-Spektroskopie," the entire contents of which is incorporated herein by reference.

The invention relates to a Fourier transformation (FT) spectrometer for obtaining hyperspectral partial images using the single shot method with a Michelson-Type Interferometer and a method for interferometric measurement, in particular for measuring chaotic movements of the object or the measurement equipment, and for scenes based on at least one "(2n+1)" periscope group that is arranged in at least one arm of the Michelson-Type Interferometer.

Single Shot Fourier Transformations Spectroscopy can in particular be used with a comparatively low to moderate spectral resolution. The spectral resolution for this spectroscopy is preferably in the range from delta_sigma of about 4 $cm^{-1}$ to about 1000 $cm^{-1}$ (1 $cm^{-1}$=1/cm=reciprocal centimeters, unit of the wave number), wherein the spectral range is preferably addressed from ultraviolet up to the terahertz range of the wavelength of electromagnetic radiation, but typically not in a single instrument. The invention can preferably be used in the visual spectral range (VIS), in the near infrared range (NIR), in the midinfrared range (MIR), in the far infrared range (FIR), in the terahertz range, or also in combined spectral ranges.

An application for the invention can be the examination of human skin by a doctor, for example for skin cancer screening. A further application can be the examination of at least partially exposed organ tissue during a surgical procedure on living human beings. A further example can be the examination of the interior of the eye, for example an examination of the retina.

A further application can for example be the analysis of foods, in particular when these are moved on an agitated and/or jerking conveyor belt. This also includes the examination of agricultural foods, for example bulk products such as grains and legumes, for which a 100% inspection is required while the conveyor is moving and/or for which at least a high sampling rate is required.

The invention can also be used for fluorescent light analysis of objects and scenes using UV incident light with analysis of the fluorescent light as the information carrier.

The invention can also be applied for measuring objects that exhibit internal movement, such as erupting volcanoes and/or firestorms during forest fires, with a relatively uniform movement of the spectrometer while overflying by helicopter and/or airplane.

The approach according to the invention can also be used to record swirling particles, for example in a flow, spectrally and spatially resolved at least with restrictions.

It is also possible to identify and sort a variety of plastics in household waste and/or in industrial waste based on the spectrum, even while in motion. Based on the spectrum, it is also possible to identify objects made of a variety of plastics when sorting waste on land and/or also objects moving in the waters of an ocean, and to facilitate local sorting as needed.

When taking measurements using the portable spectrometer according to the invention based on a manual scan over the object, objects collected as crime scene evidence, from medicine, hygiene, archaeology, botany, mineral sciences, agriculture can be analyzed hyperspectrally, typically with significantly more than 10 spectral channels per measurement point and spatially resolved. The focus in this case is generally not on the spectral information and not on the hyperspectral image of the measured object. In spite of elaborate image post-processing, the hyperspectral image can exhibit certain residual artifacts, which in many cases is regarded as tolerable since for a significant number of metrology tasks, the primary interest is on the spectral information, which should be recorded largely without loss of resolution.

The invention can also be used for close and far range thermal imaging. But it is also possible to use the invention in particular in the terahertz range for airport scanners in security gates for passenger and cargo using the transmitted light method with spectral resolution.

Prior Art

Noncyclical double beam interferometer arrangements are in this case regarded as the prior art. Nevertheless, the U.S. Pat. No. 4,976,542 by Smith with a cyclical interferometer in the form of the Sagnac interferometer, which represents a common path arrangement, will be discussed herein. In FIG. 1, it describes a Sagnac interferometer arrangement with cylinder optics 38 in combination with Fourier optics 36. The cylinder optics 38 render a focused gap opening 24 in lengthwise gap direction onto a raster detector, here in the form of a CCD chip. In combination with the Fourier optics 36, the cylinder optics 38 represents an anamorphic imaging stage. In the lateral gap direction, the effect of the Fourier optics 36 in combination with the lateral shear generating Sagnac interferometer generates a plurality of spatial interferograms on the CCD chip. This then creates the ability to detect spatial interferograms in single shot mode, and to computationally assemble these into a hyperspectral partial image in stripe form, according to the gap. However, the gap, which in this case then acts as a field of view aperture or as a field of view discriminator, is arranged upstream of the Sagnac interferometer. Due to the comparatively long optical paths, this significantly reduces the opening angle of the beam in the Sagnac interferometer.

The U.S. Pat. No. 5,777,736 by Horton describes an interferometer of type Mach-Zehnder, which features comparatively long optical paths in the interferometer in comparison a Michelson interferometer. As an interferometer of type Mach-Zehnder, it is principally difficult to adjust in comparison to a Michelson-type interferometer, which only features a single beam splitter. This difficulty also exists due to the arrangement of two beam splitters in the Mach-Zehnder interferometer. Accordingly, an interferometer of type Mach-Zehnder comparatively exhibits no particularly high long-term stability without significant engineering effort and can only be given a compact design within limits. FIG. 22 of this patent shows a pronounced astigmatism caused by the respectively single path through a tilted beam splitter plate, and which is not compensated in the interferometric beam path. This can result in non-linearities in the spatial interferogram that can cause significant difficulties for spectrum calculation or result in highly undesirable artifacts in the calculated spectrum. The resulting full image of the measured object, the scene, or the light source on the detector is overlayed by a single spatial interferogram because a composite lens—described as "exit lens" therein—is arranged as relay optics. A serial interferogram can then only be obtained with a relative motion between the interferometer and the measured object; singe shot mode is not possible because obtaining the interferogram requires uniform motion of the scene, and because the interferogram is at all times created serially and can only be extracted from an image stack for each measurement point. Document U.S. Pat. No. 5,777,736 also does not arrange field of view discriminators in the interferometer in the image position.

U.S. Pat. No. 3,684,379A by Girard describes a compact Michelson-Type Interferometer with wedge interferences for field use. The image is created on the two plane mirrors of a Michelson interferometer. But there is no field of view discriminator in the interferometer. Since these are opened beams, the wedge introduced here can generate undesirable wave front aberrations, which can significantly interfere with a spatial interferogram. When analyzing a Fourier transformation, this can result in significant problems and result in unacceptable spectrum errors.

The U.S. Pat. No. 4,523,846 by Breckingridge also describes a very compact Michelson-Type interferometer with a monolithic design, having a non-rectangular arrangement of a plane mirror as interferometer end mirror. This creates the interference of wavefronts tilted toward each other. Here too, the wedge made of refractive material and introduced into the interferometer can generate wavefront aberrations that can significantly interfere with a spatial interferogram. A gap for discriminating the field of view that acts as an effective source is in this case located at the input of the interferometer, that is to say outside of the latter. In a position of the instrument, only the spatial interferogram of the entire slot detected in the pupil plane is evidently obtained. There is then evidently no local resolution within the elongated slot. The convex surface with gap aperture at the interferometer input represents a field lens, and is therefore positioned at the image location or approximately in an interim image plane. During a relative motion between the interferometer and the measured object, in this case for example when a satellite flies over a landscape, a one-dimensional hyperspectral image can then be prepared from the sequentially detected spatial interferograms based on the Pushbroom principle. In this case, evidently only a single—in this case stripe-shaped image section—supplies a spatial interferogram at any one point in time. Due to the arrangement of the gap at the input of the interferometer, the opening angle for the beam is somewhat limited due to the optical distance from the input to the output of the interferometer. A half opening angle of approximately 10° can nevertheless be achieved. Accordingly, the light yield through the limited opening angle can nevertheless be somewhat restricted. This can result in a non-optimal signal-to-noise ratio in the measured interferogram and therefore also in the calculated spectrum.

The lateral shear can in an optical arrangement be used as a basis for generating interferences of wavefronts tilted toward each other. An entirely classical approach for this is a Michelson interferometer arrangement with two rooftop reflectors in order to generate the required lateral shear. This approach using two rooftop reflectors is generally also used for wavefront analysis and is well known to persons skilled in the art, also refer to Malacara, Optical Shop Testing, John Wiley & Sons, Inc., 1992, p. 140-141, Figure 4.16 [1] and also to Steel, Interferometry, Cambridge University Press, 1967, p. 83 last paragraph up to top of p. 84 [2].

The approach published by Kelsall in 1959 in Proc. Phys. Society, 73, p. 470, Figure 1 [3] using two triple reflectors as end reflectors of a Michelson interferometer is also known. The lateral shift of a triple reflector also generates a lateral shear between object and reference wavefronts at the output of a Michelson interferometer. To the best of our knowledge however, use of a triple reflector in the reference beam path of a Michelson interferometer is already disclosed by Twyman and Green, in this regard also refer to U.S. Pat. No. 1,565,533 and to Figure 6 therein.

In document U.S. Pat. No. 5,131,747 and DE 68906154T2, Cerutti-Maori describe a hyperspectral method with an intrinsically rigid Michelson interferometer having a double rooftop arrangement. In this case, the Michelson interferometer generally experiences a very constant movement as it flies over terrain using an aircraft. The image of the terrain is in this case created on the raster detector. The interferogram with image information is formed on the raster detector by wavefronts tilted toward each other. By synchronizing the system components, a constant movement allows each pixel of the raster detector to record a time-series signal of a double-beam interferogram as the latter passes by. But this method does not accommodate the single shot recording of an interferogram. This approach cannot be used to obtain a non-disrupted interferogram when an interferometer moves over the measured object unevenly, or for objects with chaotic relative motions, or for turbulent scenes such as bubbling magma. The document CN 106338342 A by Dou Jianyun and others describes a hyperspectral method with a double rooftop arrangement in a Michelson interferometer for objects scanned using a rotating scanning mirror. The complete image of a static scene is generated on the planar raster detector in the Fourier plane of the optics. The lateral shear introduced by an interferometer causes a spatial interferogram to overlay the image. But this interferogram—which is mapped to an object point—is also only obtained as a time series while flying over the scene. A prerequisite then is that this flyover and also the rotation of the scanning mirror must be very uniform since the resulting interferogram signals are otherwise disrupted. This hyperspectral method is then in no way suited for turbulent scenes, or even for objects with internal chaotic movements, or for handheld equipment when operated in a comparatively unsteady or jittery hand.

FIG. 1 in the industry article "Large field-of-view Fourier transform imaging spectrometer using dual-channel stitching" by Chengmiao Liu and others in OPTICS EXPRESS, Vol. 24, No. 25 dated Dec. 12, 2016, p. 28473-28490, http://dx.doi.org/10.1364/OE.24.028473, [4] shows a Lateral-Shear Interferometer with rooftop reflectors. The spatial interferogram is created in the Fourier plane of a downstream lens with image information. But this system operates on a timeseries to obtain the interferogram signal and is therefore unsuited for single shot applications.

In other words: although a spectral metrology method based on the documents U.S. Pat. No. 5,131,747, CN 106338342 A or also [4] will at all times supply a complete image of the measured object or scene, a spatial interferogram is nevertheless obtained based on a timeseries. This then implies a nearly constant relative motion between the interferometer and the measured object, as is generally the case during a calm flyover by a satellite or an aircraft over terrain. Accordingly, due to the chaotic movements in the scene—such as during an automobile crash test—or during nonuniform or even chaotic movements of the interferometer when the instrument is freely held by hand, this approach is rather unsuited for turbulent scenes because the interferogram signals are highly likely disrupted and completely unsuited for typical analysis using Fourier transformation.

The family patents DE 102010006239 B3, EP 2526373 B1, and U.S. Pat. No. 8,934,104 B2 by K. Korner, R. Berger and W. Osten each describe a Michelson-Type Interferometer wherein a constant lateral shear can be achieved by using a special triple mirror in the interferometer, see FIG. 2. On this interferometer, the three plane mirrors of the triple mirror are arranged vertically in relation to a common reference plane, in relation to which the beam splitter surface is likewise arranged vertically. The special triple mirror described therein generates an invariant lateral shear. The invariance of the lateral shear for a lateral shift v of the special triple mirror is shown in FIG. 3 of the family patents cited above.

The optical arrangement shown in the family patents cited above with a special triple reflection in an arm of a Michelson-Type Interferometer, on which the three mirror surfaces are each arranged vertically in relation to a reference plane, is designed for recording the distance, depth, profile, shape, waviness, and/or roughness of technical or biological objects. The reference plane is arranged vertically in relation to the beam splitter surface of the Michelson-Type Interferometer. This optical arrangement presented there is however completely unsuited for imaging FT spectroscopy. because the measured object is in this case arranged in the beam path of the interferometer, and is therefore itself part of the Michelson-Type Interferometer. Such an object arrangement is already generally unsuited for spectroscopy because the "interferometric gain" of the interferometer results in obtaining rather substantially falsified spectrums of the measured object that can only be numerically corrected within limits.

In the prior art, it is generally comparatively simple to assemble a shaky image from non-equidistant image points, compared to obtaining a low-error spectrum from a disrupted interferogram, in particular when the type and strength of the disruption in the interferometer is largely unknown, which is frequently the case.

According to an aspect, the task underlying the invention is to operate an FT spectrometer in single shot mode. The task in particular consists of simultaneously generating two spatial interferograms of individually selected regions of the image of the object to be detected, preferably however a larger number of spatial interferograms that at least partially contain the information about the searched spectrum, and to thus record two or more generally complete spatial interferograms in a single recording.

According to an aspect, a Fourier transformation spectrometer, FT spectrometer, comprises the following:
  Michelson-Type Interferometer comprising:
    at least one beam splitter unit with a planar beam splitter surface that is designed
      to split an incident light beam of a spatially expanded object into a first partial beam and a second partial beam; and
      to at least partially overlay the first partial beam and the second partial beam with a lateral shear;
    a first beam deflection unit designed to deflect the first partial beam at least a first time;
    a second beam deflection unit designed to deflect the second partial beam at least a first time;
    wherein at least one among the first beam deflection unit and the second beam deflection unit represents a (2n+1) periscope group with (2n+1) mirror surfaces and all (2n+1) mirror surfaces are arranged vertically in relation to a common reference plane, in order to respectively deflect the first partial beam and/or the second partial beam (2n+1) times, and wherein the (2n+1)-fold deflection generates the lateral shear between the first partial beam and the second partial beam, wherein n is a natural number $\geq 1$;
  wherein the FT spectrometer additionally comprises:
    at least one lens arranged opposite the beam splitter unit such that the incident light passes the lens at least partially before said light beam is split on the beam splitter unit and the first partial beam and the second partial beam respectively generate a plurality of coherent image points of the spatially expanded object in an image plane between the beam splitter unit and a raster detector;
    the raster detector having at least one detector field to record a plurality of spatial interferograms on the basis of the spatial overlay of the first partial beam and the second partial beam, which corresponds to the at least partial imaging of the plurality of coherent image points; and
    at least one computing unit for the Fourier transformation of the plurality of spatial interferograms to generate a plurality of spectrums, and based thereon, to generate at least one hyperspectral image of the spatially expanded object.

According to the invention, a (2n+1) periscope group, in particular a triple periscope group with n=1 or another (2n+1) periscope group with n=2, 3, 4 is used as end reflector in a Michelson-Type Interferometer to generate a lateral shear s for Fourier spectroscopy.

In other words, a Fourier transformation spectrometer is designed for at least partial hyperspectral single shot imaging of a measured object as a product of a calculation using a computer system with a computing program to obtain spectrums by means of Fourier transformation, wherein the Fourier transformation spectrometer has a lens arranged upstream of the Michelson-Type Interferometer that is used as imaging system for the measured object, formed with the optical axis OAT to generate at least one focused input beam for the Michelson-Type Interferometer, and wherein the Michelson-Type Interferometer further comprises:
  A beam splitter with planar beam splitter surface, wherein the beam splitter is used for beam splitting, thus forming two partial beams, and also for at least partial beam unification with a lateral shear s between the two partial beams, and wherein in particular a reference plane can exist on the Michelson-Type Interferometer that is spanned by the normal of the planar beam splitter surface and by the optical axis of the upstream lens at the input of the Michelson-Type Interferometer;
  preferably at least one light source;
  a raster detector, wherein at least one spatial interferogram can be formed on the raster detector,
  wherein in particular either at least an approximately planar end mirror or a planar end mirror surface can be arranged in the first interferometer arm of the Michelson-Type Interferometer, and a triple periscope group can be arranged in the second interferometer arm as an end reflector, and the triple periscope group can consist of an arrangement of—in total—three at least approximately planar mirrors or at least approximately planar mirror surfaces in throat or W shape, and the latter are respectively aligned in relation to each other at angles that are essentially vertical in relation to the reference plane, or
  wherein respectively one triple periscope group can be arranged as an end reflector in each of the two interferometer arms of the Michelson-Type Interferometer, that is to say wherein a (2n+1)-fold periscope group with n=2, 3, 4 is arranged as an end reflector in at least one of the two interferometer arms of the Michelson-Type Interferometer, the periscope group consisting of an arrangement of—in total (2n+1)— planar mirrors or planar mirror surfaces, preferably in throat or W shape or in a mixed form, and the latter are respectively aligned in relation to each other at angles that are essentially vertical in relation to a common reference plane, and wherein in all cases the total number of mirrors or mirror surfaces in the Michelson-Type Interferometer is at least four, and—even given a total number greater than four—is generally an even number; and wherein in all cases, the rays of a partial beam are respectively only reflected once on every mirror or on every mirror surface in the Michelson-Type Interferometer upon passing an interferometer arm.

In other words, a shear invariant double beam interferometer formed as a Michelson-Type Interferometer can be used with a raster detector, in particular for measuring with chaotic relative movements of a measured object and/or for turbulent scenes, with at least partial hyperspectral imaging. On this interferometer, two coherent partial beams TB1 and TB2 are formed on the output with a lateral shear s, in that at least one of the two arms of the interferometer, an intrinsically preferably rigid periscope group with an odd number of plane mirrors, but at least three, is arranged as an end reflector to generate the lateral shear. The plane mirrors are aligned at angles in relation to each other, and also at all times essentially vertically in relation to a common reference plane in a throat or W shape. The total number of mirrors or mirror surfaces in the two arms of the Michelson-Type Interferometer is at least four and is at all times an even number. In particular, a pair of coherent images or partial images of the measured object or the scene is formed in the interferometer, and these images or partial images are subject to a field of view discrimination prior to forming spatial interferograms by means of anamorphic imaging of the selected field of view, wherein said interferograms are used to calculate spectrums with fast Fourier transformation.

The invention in particular relates to an FT spectrometer comprising the following:

A double beam interferometer having a first and a second arm, wherein the double beam interferometer corresponds to a Michelson-Type Interferometer, comprising:
  at least one beam splitter unit having a planar beam splitter surface, wherein the beam splitter unit and in particular the beam splitter layer is designed
    to split an incident light beam of a spatially expanded object into a first partial beam in the first arm of the Michelson-Type Interferometer by means of transmission through the beam splitter layer, and a second partial beam in a second arm of the Michelson-Type Interferometer by means of reflection on the beam splitter surface; and
    for at least partial overlaying of the first partial beam and the second partial beam with a lateral shear by transmission of the second partial beam through the beam splitter layer and by reflection of the first partial beam on the beam splitter layer;
  a first beam deflection unit designed to deflect, in particular to reflect or mirror, the first partial beam at least a first time;
  a second beam deflection unit designed to deflect, in particular to reflect or mirror, the second partial beam at least a first time;

wherein at least one among the first beam deflection unit and the second beam deflection unit represents a (2n+1) periscope group with (2n+1) mirror surfaces or mirror surface sections and all (2n+1) mirror surfaces or mirror surface sections are essentially arranged vertically in relation to a common reference plane, in order to respectively deflect the first partial beam and/or the second partial beam (2n+1) times in the first one, and wherein the (2n+1)-fold deflection generates the lateral shear s between the first partial beam and the second partial beam;

wherein the FT spectrometer additionally comprises:
  at least one lens, that can be comprised of e.g. lens elements and/or hollow mirrors, wherein the lens is arranged opposite, in particular upstream of, the beam splitter unit such that the incident light passes or travels through the lens at least partially and said incident light is then focused or formed into a beam before said light beam is split on the beam splitter unit and the first partial beam and the second partial beam respectively generate a plurality of coherent image points of the spatially expanded object in an image plane in light direction downstream of the beam splitter unit and upstream of a raster detector;
  the detector having at least one detector field to record a plurality of spatial interferograms on the basis of the spatial overlay of the first partial beam and the second partial beam, which corresponds to at least the partial imaging of the plurality of coherent image points; and
  at least one computing unit for the Fourier transformation of the plurality of spatial interferograms to generate a plurality of spectrums, and based thereon, to generate at least one hyperspectral image of the spatially expanded object.

Since the lateral shear is invariant in this Michelson-Type Interferometer according to the invention, a high wave number accuracy can be achieved, in particular after calibration, and a high wave number constancy can be achieved. This is particularly meaningful for a high spectral resolution. On fine field of view discriminators that permit high-resolution hyperspectral images, there is no risk of the interferometer coming out of adjustment—barring extreme conditions.

Regarding the lens arranged upstream of the beam splitter unit, there is in particular the advantage that light with a comparatively large solid angle of a measurement location can be captured of the measured object or the scene, and that said light can be detected as interference light using a double beam interferometer. This can permit use of a downstream lens at the interferometer output to capture said interference light with the largest possible aperture angle alpha in order to use the largest possible share of the captured light energy for detection. This can also permit comparatively short integration times of a raster detector, so that single shot measurements can also be made of moving measured objects and of turbulent scenes.

When actively illuminated with a light source, the energy of the latter can potentially be put to optimized use. All the light of the latter can for example as much as possible and essentially in its entirety be guided onto a narrow object field. In this case, it may then under the aspect of energy use essentially represent no disadvantage when only a small, narrow field, or an object section is recorded in a single shot measurement, because only the former may then also have to be fully illuminated.

In particular, high ruggedness can be achieved by reducing a highly undesired and out of adjustment state of the interferometer. This can in particular be the case when the interferometer is essentially miniaturized, in particular when the beam splitter unit and the end reflectors of the interferometer are miniaturized, for example also when a foil beam splitter or a pellicle beam splitter are to be used as needed. These are relatively insensitive to vibrations at large expansions. A further advantage is that particularly short distances can be realized in the arms of the interferometer.

Moreover, the two partial beams that leave the interferometer can be generated as much as possible free of astigmatism.

A further advantage is that an adaptability to the object can be achieved as needed when a region of said object proves to be of particular interest, along with a pattern projected onto the measured object. This can also facilitate wide-ranging flexibility for the selection of the lateral resolution in the image of the measured object.

A particular advantage is that even if vibrations occur in the environment of the metrology arrangement, or if turbulence occurs in a scene to be measured, that is to say in for example field use, or also for handheld instruments, generally largely unfalsified spectrums can be obtained on the basis of the calculation using Fourier transformation of minimally disrupted spatial interferograms. In this case, certain errors are however tolerated in the spectral image when scanning the measured object or the scene for imaging purposes of turbulent scenes or when performing handheld measurements, that is to say when rendering the image with the associated spectrums. A spectral image is also known as a hyperspectral image, which can generally be available in the form of a data cuboid (x, y, sigma) having the wave number sigma or (x, y, lambda) with the wavelength lambda.

A particular advantage of the invention relates to obtaining spatial interferograms in single shot mode using a double beam interferometer with a lower optical distance in the interferometer in comparison to a Sagnac interferometer, also known as a cyclical interferometer. As a result, beams with a larger opening angle than on a Sagnac interferometer can be used. The beam guidance in the optical setup according to the invention provides the opportunity for significant miniaturization of the interferometer. This is accomplished by using optical invariances, in this case an invariant lateral shear in conjunction with a special mirror arrangement. This invariant lateral shear permits achieving a very high wave number accuracy that then also permits a high spectral resolution.

In particular during signal recording, there are essentially also no moving, and instead essentially (inherently) rigid components in the entire spectrometer. This has the advantage that the FT spectrometer can exhibit relatively high ruggedness.

By concurrently operating a comparatively simple monitor camera, preferably arranged on the Fourier transformation spectrometer and for concurrent image recording of the object while measuring with the FT spectrometer, assembling slightly or only moderately shaky image series from the spectrometer measurements using image postprocessing becomes comparatively simple—in comparison to obtaining a low-error spectrum from a disrupted interferogram. This monitor camera can firstly preferably be designed for the visible spectral range, but can alternatively also be designed for the near infrared spectral range.

The single shot approach may also permit the use of the comparatively cost-effective, while also very high-powered, light sources, which are essentially not very stable over time with regard to their output power, and therefore can exhibit power output fluctuations by as much as 10%. Fluctuations of the output power can potentially present a problem when recording interferograms based on serial methods, because these can result in highly undesired modulation in the determined interferogram.

The reference plane is preferably spanned by the normal of the beam splitter unit and by the optical axis of the upstream lens.

The (2n+1) periscope group preferably corresponds to a throat or a W shape.

Each of the mirror surfaces is preferably arranged to reflect the first partial beam or the second partial beam once.

In particular at least one among the first beam deflection unit and the second beam deflection unit is designed to deflect the first partial beam or the second partial beam once by means of single reflection on a mirror surface or an individual mirror surface of the corresponding beam deflection unit.

In a particularly preferred case, the vertical incidence of the partial beam onto the mirror surface can represent a reverse reflection, that is to say a deflection that essentially corresponds to 180°.

In particular at least one among the first beam deflection unit and the second beam deflection unit is designed to deflect the first partial beam or the second partial beam three times by means of triple reflection on three mirror surfaces of a triple periscope group of the corresponding beam deflection unit.

The first beam deflection unit and the second beam deflection unit together in particular has a number of mirror surfaces that either corresponds to (2n+1)+1 or $(2n_1+1)+(2n_2+1)$, and wherein n is a natural number $\geq 1$, $n_1$ is a natural number $\geq 1$ and $n_2$ is a natural number $\geq 1$.

In other words, the total number of the mirrors or mirror surfaces in the Michelson-Type Interferometer in both arms is at least 4, that is to say either (2n+1)+1 or $(2n_1+1)+(2n_2+1)$, in which case the total number is an even number.

For example, one arm can have a (2n+1) mirror group that comprises three mirrors for n=1, and the other arm can have a single mirror. In this case, the total number is 4 mirrors or mirror surfaces.

For example, one arm can have a (2n+1) mirror group that comprises five mirrors for n=2, and the other arm can have a single mirror. In this case, the total number is 6 mirrors or mirror surfaces.

For example, one arm can have a $(n_1+1)$ mirror groups, where $n_1=1$ comprises three mirrors, and the other arm can have a further $(n_2+1)$ mirror group, where n2=1 comprises three mirrors. In this case, the total number is 6 mirrors or mirror surfaces. $n_1$ in this case relates to the first arm, and $n_2$ relates to the second arm.

For example, one arm can have a $(n_1+1)$ mirror groups, where $n_1=2$ comprises five mirrors, and the other arm can have a further $(n_2+1)$ mirror group, where $n_2=1$ comprises three mirrors. In this case, the total number is 8 mirrors or mirror surfaces.

The Michelson-Type Interferometer also in particular comprises at least one field of view discriminator unit arranged downstream of the beam splitter unit, where the field of view discriminator unit is arranged such that the first partial beam and/or the second partial beam is spatially selected.

In particular, at least one field of view discriminator unit is arranged between two of the (2n+1) mirror surfaces of the (2n+1) periscope group of the at least one beam deflection unit such that the first partial beam and/or the second partial beam is spatially selected.

In particular, at least one field of view discriminator unit is integrated in one of the mirror surfaces of the first beam deflection unit and/or the second beam deflection unit.

The Michelson-Type Interferometer also in particular comprises at least one field of view discriminator unit arranged downstream of the first beam splitter unit, and a second field of view discriminator unit is arranged such that the first partial beam and the second partial beam are spatially selected, and such that the first field overview discriminator unit is optically conjugated in relation to the second field of view discriminator unit.

The field of view discriminator unit in particular comprises at least one of the following:
a gap-shaped shading aperture,
a micro-gap shading aperture array,
a pinhole shading aperture,
a one-dimensional or a two-dimensional pinhole shading aperture array in the form of an aperture disk,
a micro-gap shading aperture array with a plurality of micro gaps in a laterally shifted arrangement,
a micro-gap shading aperture array with mechanically movable elements,
a reflective gap-shaped region that represents a part of the first and/or the second beam deflection unit.

In other words, this can optionally relate to a Fourier transformation spectrometer, wherein at least one field of view discriminator is mapped to the Michelson-Type Interferometer.

This can in particular relate to a Michelson-Type Interferometer on which at least one field of view discriminator is arranged.

This can preferably relate to a Fourier transformation spectrometer, wherein at least one field of view discriminator is arranged downstream of the beam splitter of the Michelson-Type Interferometer.

This can in particular relate to a Fourier transformation spectrometer on which a field of view discriminator is arranged in an interferometer arm of the Michelson-Type Interferometer in a real mirror surface.

This can in particular also relate to a Fourier transformation spectrometer on which a field of view discriminator is arranged the Michelson-Type Interferometer in the first interferometer arm in a surface optically conjugated in relation to the apparent end mirror surface of the second interferometer arm.

This can in particular also relate to a Fourier transformation spectrometer on which a second field of view discriminator is arranged in the second interferometer arm of the Michelson-Type Interferometer, wherein said second field of view discriminator is optically conjugated in relation to the field of view discriminator in the first interferometer arm and is at approximately formed geometrically equivalent to the first field of view discriminator.

Additionally or alternatively, this can also relate to a Fourier transformation spectrometer on which at least one field of view discriminator is arranged directly upstream of the Michelson-Type Interferometer.

Additionally or alternatively, this can also relate to a Fourier transformation spectrometer on which at least one field of view discriminator is mapped to the image of a measured object in the beam path in the Michelson-Type Interferometer, which is formed by means of an upstream lens.

Additionally or alternatively, this can also relate to a Fourier transformation spectrometer on which a first field of view discriminator in the Michelson-Type Interferometer is mapped to the plane mirror or the end mirror, and a second field of view discriminator is mapped to the triple periscope group.

Additionally or alternatively, this can also relate to a Fourier transformation spectrometer on which a first field of view discriminator in the Michelson-Type Interferometer is formed by the plane mirror or the end mirror, or by a mirror of the triple periscope group.

In particular, this can also relate to a Fourier transformation spectrometer on which at least one field of view discriminator in the Michelson-Type Interferometer is formed as a raster mirror or as a raster mirror surface.

In particular, this can also relate to a Fourier transformation spectrometer on which the elements of the raster mirror or the raster mirror surface in the Michelson-Type Interferometer are mapped to computer controllable motion elements.

Additionally or alternatively, this can also relate to a Fourier transformation spectrometer on which given a placement of respectively one field of view discriminator in each interferometer arm of the Michelson-Type Interferometer, said two field of view discriminators are arranged optically conjugated in relation to each other.

In particular, this can also relate to a Fourier transformation spectrometer on which at least one field of view discriminator is formed as a gap-shaped shading aperture.

In particular, this can also relate to a Fourier transformation spectrometer on which at least one field of view discriminator is formed as a micro-gap shading aperture array.

Additionally or alternatively, this can also relate to a Fourier transformation spectrometer on which at least one field of view discriminator is formed as a pinhole shading aperture.

Additionally or alternatively, this can also relate to a Fourier transformation spectrometer on which at least one field of view discriminator is formed as a one-dimensional or two-dimensional pinhole shading aperture array in the form of an aperture disk.

In particular, this can also relate to a Fourier transformation spectrometer on which a micro-gap shading aperture array is formed with micro-gaps in a laterally shifted arrangement.

In particular, this can also relate to a Fourier transformation spectrometer on which a micro-gap shading aperture array is formed with mechanically movable elements.

In particular, this can also relate to a Fourier transformation spectrometer on which a fine structured field of view discriminator in gap form or in dotted line form is mapped to the measured object or to the field of a light source, and the lengthwise direction of the field of view discriminator is aligned vertically in relation to the reference plane.

In particular, this can also relate to a Fourier transformation spectrometer on which the light source itself is formed with a fine structure in gap form or in the form of fine luminescent elements in a straight line or in a zigzag line, and the lengthwise direction of the latter is aligned vertically in relation to the reference plane.

In particular, this can also relate to a Fourier transformation spectrometer on which the field of the measured object and the field of the light source are in at least a partial region arranged optically conjugated in relation to each other.

In particular, this can also relate to a Fourier transformation spectrometer on which the Michelson-Type Interferometer is formed as an air type or as a prism type or as a hybrid air-prism arrangement.

Additionally or alternatively, this can also relate to a Fourier transformation spectrometer on which a confocal arrangement is arranged upstream of the Michelson-Type Interferometer.

Additionally or alternatively, this can relate to a Fourier transformation spectrometer on which the confocal arrangement is formed with a rigid aperture disk or a rotating aperture disk.

In particular, this can also relate to a Fourier transformation spectrometer on which the confocal arrangement is formed with a spatial light modulator in reflection or transmission.

In particular, this can also relate to a Fourier transformation spectrometer on which the confocal discriminator elements of a confocal arrangement are at least approximately optically conjugated with at least one effective mirror surface in the arm of a Michelson-Type Interferometer.

In particular, this can also relate to a Fourier transformation spectrometer on which at least one field of view discriminator in the Michelson-Type Interferometer is formed as a controllable spatial light modulator in reflection.

In particular, this can also relate to a Fourier transformation spectrometer on which at least one field of view discriminator in the Fourier transformation spectrometer system is formed as a controllable spatial light modulator in transmission.

In particular, this can relate to a Fourier transformation spectrometer on which motion devices are mapped in the depth axis to the measured object or the mobile measurement head or a component of the mobile measurement head.

In particular, at least one among the first beam deflection unit and the second beam deflection unit has a prism but at least one reflection surface that is designed to reflect the first partial beam and/or the second partial beam once.

In particular, the Fourier transformation spectrometer further comprises a confocal arrangement arranged upstream of the Michelson-Type Interferometer.

In particular, the confocal arrangement has a rigid aperture disk or a rotating aperture disk and/or a spatial light modulator in reflection or transmission.

In particular, the beam splitter unit represents an amplitude beam splitter and has a planar beam splitter layer, a mylar foil, or a lattice.

In other words, this can optionally relate to a Fourier transformation spectrometer on which the beam splitter is formed as an amplitude beam splitter, represented by a planar beam splitter layer, or a mylar foil, or a lattice.

According to a further aspect, a method for interferometric measurement by means of a Fourier transformation spectrometer with Michelson-Type Interferometer comprises:
- splitting an incident light beam transmitted from a spatially expanded object into a first partial beam and a second partial beam using a beam splitter unit;
- at least a one-time deflection of the first partial beam using a first beam deflection unit;
- at least a one-time deflection of the second partial beam using a second beam deflection unit, wherein the first partial beam and/or the second partial beam is deflected (2n+1) times on at least one among the first beam deflection unit and the second beam deflection unit by means of a (2n+1) periscope group with (2n+1) mirror surfaces in order to generate a lateral shear between the first partial beam and the second partial beam, wherein n is a natural number ≥1;
- sending the incident light beam through a lens prior to the splitting to generate a plurality of coherent image points of the spatially expanded object in an image plane between the beam splitter unit and a raster detector;
- at least partially spatially overlaying the first partial beam and the second partial beam using the beam splitter unit;
- at least partially rendering the plurality of coherent image points while at the same time generating a plurality of spatial interferograms on a detector field of the raster detector on the basis of the spatial overlay;
- recording the plurality of interferograms using the raster detector;
- Fourier transforming the plurality of spatial interferograms to generate a plurality of spectrums, and based thereon, generating a hyperspectral image of at least a section of the spatially expanded object.

The method preferably comprises the steps that are triggered and at least partially executed by means of at least one computing unit:
- multiple simultaneous recording of the plurality of spatial interferograms at respectively different points in time;
- Fourier transforming the plurality of spatial interferograms recorded at respectively different points in time to generate a plurality of spectrums; and
- generating at least one hyperspectral image of the spatially expanded object.

A particular advantage is that among individually selected regions of the image of the object to be detected at least two spatial interferograms can be generated and recorded, but generally a larger number of spatial interferograms that at least partially contain the information about the searched spectrum, and in that two or several complete spatial interferograms can recorded in this manner in a single recording.

The use of a field of view discriminator is merely optional. A field of view discriminator can for example be omitted in the FT spectrometer according to the invention in particular when examining isolated point light sources (star without neighboring stars).

The following describes further embodiments, features, and examples that firstly do not restrict the invention, and secondly can be combined with each other, provided they do not exclude each other.

The objective is essentially to obtain largely unfalsified spectrums even in the presence of vibrations and/or turbulences in a scene to be measured, and therefore for example in field use; nevertheless, certain errors need to be permitted when scanning the measured object—that is to say when generating a hyperspectral image in the form of a known data cuboid (x, y, sigma), with sigma as the wave number or (x, y, lambda) with lambda as the wavelength. The spectral information is to be obtained in single shot mode. As a result, said information is less error-prone than the local information of the object, which is obtained in series.

For the purposes of this invention, the measured object is generally located outside of the interferometer, and is in this case generally arranged upstream of the interferometer.

It is firstly stated for the record that this also refers to single shot imaging when only two or a few spatial interferograms can be obtained of a measured object in single shot mode to computationally obtain a hyperspectral partial image. However, generally at least one hundred spatial interferograms are to be obtained with the invention in single shot mode. These spatial interferograms can for example originate from a line, a narrow area or from a raster, respectively on the measured object.

Spatial interferograms for Fourier spectroscopy using a lateral shear between object and reference wavefronts can be obtained at the output of a Michelson-Type Interferometer by using an anamorphic lens with positive refractive power arranged downstream of the interferometer. A spatial interferogram can in this case be detected in the Fourier plane of the downstream lens. The Fourier plane represents the downstream focal plane of the specified lens. Using a numerically configured Fourier Transformation, the spectrum is calculated from the spatial interferogram.

In comparison to methods working serially with a spatial interferogram in the full image, the present invention either has a one-dimensionally limited measurement field or also two-dimensionally distributed spectrums in a relatively coarse raster of measurement locations. However, this disadvantage is somewhat diminished in significance when the measured object is actively illuminated with an artificial light source, and the available light energy P_total from this light source is concentrated onto for example a stripe-shaped surface A_stripe instead of for example onto a circular surface A_circle, resulting in a significantly higher illumination strength. The illumination strength on the smaller stripe-shaped surface is then correspondingly higher, and the integration time of a raster detector can be correspondingly reduced. The solution according to the invention then has an advantage in particular for illuminating with a light source geometrically matched to the measurement field of the measured object. A particular advantage is given for the case when a very high illumination strength can be used on a nonbiological measured object at least for a short duration when illuminating the latter, for example in the form of a narrow light stripe on the measured object. The measured object can also be illuminated with a bundle cross-section converter that is shaped into an elongated, narrow area.

The features of the invention are described as follows.

The invention in particular relates to a Fourier transformation spectrometer with at least partial hyperspectral imaging of a measured object as a product of a calculation using a computer system for calculating spectrums by means of Fourier transformation.

The Fourier transformation spectrometer is in particular formed with a lens arranged upstream of the Michelson-Type Interferometer, the lens having an optical axis OAI and is used as a focusing imaging system to generate at least one focused input beam for the Michelson-Type Interferometer. The upstream lens can be formed with one stage, two stages, or also multiple stages. The Michelson-Type Interferometer is then arranged downstream of the upstream lens, and is known to have two interferometer arms. There is generally a plurality of focused input beams at the input of the Michelson-Type Interferometer because one focused input beam is mapped to every recorded object point. These input beams are in this case therefore generally understood to be an ensemble of input beams because imaging information is transported and a separate input beam is mapped to each image point, so that a plurality of input beams are then also mapped to a plurality of image points. An ensemble of input beams then generally exists. In the further description in the figures, a beam ultimately refers to the ensemble of beams, and one beam is identified as a representative or shown in the figures. Hereinafter, the same is also the case for partial beams. Each partial beam is in the sense of the invention in this case representative for an ensemble of partial beams.

The Michelson-Type Interferometer in particular also comprises:

A beam splitter with a planar beam splitter layer, preferable formed by a planar beam splitter surface or preferably a mylar foil, or preferably a lattice. The beam splitter is used for both beam splitting, thus forming two partial beams, and also for at least partial beam unification using a lateral shear s between the two partial beams TB1 and TB2.

In particular a reference plane RE is formed on the Michelson-Type Interferometer that is spanned at the input of the Michelson-Type Interferometer by the normal NT of the planar beam splitter surface of the Michelson-Type Interferometer and by the optical axis OAI of the upstream lens.

For detection, a raster detector can be arranged downstream, of the Michelson-Type Interferometer. The raster detector can be a UV camera, and a CCD or a CMOS camera in the visible spectral range. An InGaAs camera can be advantageously used in the near infrared spectral range. A Focal Plane Array (FPA) (also called IRFPA), which is also cooled if appropriate, is used as a raster detector in the medium infrared range. A raster detector with a mercury-cadmium telluride compound (MCT) is advantageously used for hybrid CMOS FPA technology.

Bolometer matrix detectors, in particular microbolometers, can be used for the entire infrared range. Matrix detectors are preferably used for this invention.

For any of the already aforementioned technologies and spectral ranges, it is however preferably also possible to arrange two or several fast line detectors downstream of the Michelson-Type Interferometer. In this case, the individual line detectors are preferably for purposes of primary data recording generally arranged in parallel in relation to each other in a common detector field, but digitally-electronically independent of each other. These are then operated independently to achieve a maximum readout speed. The number of line detectors corresponds to the number of measurement points. The individual pixels of a line can in this case also be formed with a particularly high aspect ratio to detect the largest possible amount of light energy for purposes of a high signal-to-noise ratio. Such uses are in particular employed for aerospace applications. This makes sense when a higher lateral resolution in the image is desired in one direction, the y direction in this case, but not in the x direction.

Additionally, for purposes of illuminating the measured object, the Michelson-Type Interferometer is preferably firstly either equipped with at least one light source that is preferably also controllable and can form light patterns. And secondly, the measured object can also be self-radiating, such as a hot exhaust cloud with radiation in the infrared spectral range.

The Fourier transformation spectrometer is formed with a lens arranged upstream of the Michelson-Type Interferometer that is used as imaging system for the measured object, with the optical axis OAT to generate at least one focused input beam EB for the Michelson-Type Interferometer.

An upstream lens is accordingly positioned upstream of the Michelson-Type Interferometer, the lens being used as the imaging system for the measured object. It is in particular used to generate at least one focused input beam EB for a Michelson-Type Interferometer. The upstream lens is preferably at least approximately telecentrically formed on the side facing the interferometer. This upstream lens can preferably also be formed telecentrically on both sides.

A telecentricity on the side facing the interferometer generally significantly reduces the requirements on the downstream optics because no very oblique rays occur.

The Michelson-Type Interferometer can preferably also be formed as a mobile measurement head with an upstream lens, in particular with a flashlight source synchronized to the raster detector.

Either, only one spatial interferogram is formed on the raster detector. The latter is preferably generated by means of a Fourier lens, and at the least approximately planar waves are caused to interfere. Alternatively, an approach without a Fourier lens and without further optical components at the interferometer output can also be implemented. This then causes the interference of two spherical waves on the raster detector because beams are not formed. The interference of spherical waves, in particular with a small curvature radius, is however not a particularly satisfactory technical solution for FT spectroscopy because the spatial interferogram can have nonlinearities in the edge region that can render the calculation of spectrums significantly more difficult.

Alternatively, instead of only one spatial interferogram, a plurality of spatial interferograms is formed on the raster detector with an anamorphic imaging stage that is arranged downstream of the Michelson-Type Interferometer. This is the preferred approach.

The Michelson-Type Interferometer can preferably be constructed with an angle of 90 degrees between the two interferometer arms. Furthermore, the Michelson-Type Interferometer can preferably also be constructed with an angle between the two interferometer arms greatly different from 90 degrees (1 degree=1/360 of the full circle). The two interferometer arms can preferably certainly also have an angle of up to 135 degrees or also preferably up to 150 degrees, or preferably of 45 degrees, also preferably up to 30 degrees in relation to each other. Deviating from rectangularity between the interferometer arms can present significant advantages under certain boundary conditions—such as an elongated construction space specified in the design.

The measured object can be illuminated, and reflected, scattered, or also florescent light can be spectrally analyzed. But transmitted light can also be analyzed, including as florescent light.

However, the measured object can also be a self-luminescent object, in the form of hot exhaust gases of an aircraft jet engine, with a dominant spectrum also in the midinfrared spectral range.

The invention is now firstly also characterized in that preferably either an at least approximately planar end mirror or a planar end mirror surface is arranged in the first interferometer arm of the Michelson-Type Interferometer. This planar end mirror or planar end mirror surface is preferably formed narrow. A triple periscope group is arranged as an end reflector in the second interferometer arm. According to the definition, the triple periscope group consists of an arrangement of in total three at least approximately planar mirrors or at least approximately planar mirror surfaces in throat or W shape, and respectively with an angle in relation to each other. These at least approximately planar mirrors or at least approximately planar mirror surfaces are in this case generally aligned vertically in relation to the reference plane RE, wherein the reference plane RE in the Michelson-Type Interferometer is generally arranged vertically in relation to the beam splitter surface.

FIG. 3 in the patent document DE 10 2010 06 239B3 shows the case of an invariant lateral shear for a triple periscope group according to the definition cited above. When a lateral shift v of a triple periscope group occurs, the lateral shear between the input and output beams remains unchanged.

The invention is additionally also characterized in that preferably respectively one triple periscope group according to the definition cited above is arranged as an end reflector in each of the two interferometer arms of the Michelson-Type Interferometer.

Furthermore, the invention is now also characterized in that preferably one (2n+1)-fold periscope group, where n=2, 3, 4 . . . is arranged as an end reflector in at least one of the two interferometer arms of the Michelson-Type Interferometer, wherein said periscope group consists of an arrangement of in total (2n+1) planar mirrors or planar mirror surfaces in throat or W shape, or in a mixed shape, and respectively with an angle in relation to each other. These at least approximately planar mirrors or at least approximately planar mirror surfaces are generally aligned vertically in relation to a common reference plane RE, wherein here too, the reference plane RE in the Michelson-Type Interferometer is generally arranged vertically in relation to the beam splitter surface.

In all cases, the total number of mirrors or mirror surfaces in the Michelson-Type Interferometer is at least four, and is generally an even number for a total number larger than four.

The use of a triple periscope group according to the definition cited above is regarded as technically particularly advantageous in comparison to periscope groups with a number of mirrors larger than three, because the optical distances are comparatively the shortest in this case, and because their construction is comparatively straightforward.

In this case, a triple periscope group or a (2n+1)-fold periscope group where n=2, 3, . . . is formed and arranged in the interferometer such that the mirrors and mirror surfaces of the latter are generally arranged vertically in relation to a reference plane RE. The angle of incidence of the main beam of a partial beam in the interferometer onto one of the planar mirrors or one of the planar mirror surfaces is in this case generally larger than two degrees. The aperture angle of the partial beam is generally less than the angle of incidence of the main beam; as a result, there is then in no case a vertical incidence of rays—not even of edge rays—onto one of the planar mirrors or one of the planar mirror surfaces.

The rays of a partial beam are respectively in all cases only reflected once on every mirror or on every mirror surface in the Michelson-Type Interferometer upon passing an interferometer arm.

A triple periscope group or a (2n+1)-fold periscope group with n=2, 3, . . . generally causes an invariant lateral shear at the output of the interferometer. Even when this periscope group is moved laterally, the lateral shear resulting from the geometry of this periscope group is generally entirely unchangeable.

This constant lateral shear preferably firstly either creates in the Fourier plane of a Fourier lens plane wavefronts tilted toward each other, or cylindrical wavefronts preferably tilted toward each other. These cylindrical wave fronts tilted toward each other are generated at the output of an anamorphic imaging stage arranged downstream of the interferometer. These cylindrical waves generated by beam splitting generally form spatial interferences and are guided toward detection using a raster receiver.

Given a plurality of spatial interferograms, the spectrum is calculated by means of Fourier transformation from each spatial interferogram, and is mapped to an image point.

Secondly, spherical waves with a lateral shear can however also be caused to interfere at the output of the interferometer.

The individual mirrors or mirror surfaces preferably at least approximately fully cover the cross-section of a partial beam; as a result, preferably no beam passes a rooftop or is split by the latter.

The Michelson-Type Interferometer is preferably matched with respect to the optical distances for the main beams in the two interferometer arms, so that for this difference of the optical distances (OPD=optical path difference), the value is equal to zero, and symmetric interferograms are formed. However, by inserting refractive materials, for example a comparatively thin transparent plane parallel plate arranged vertically in relation to the axis in an arm of the Michelson-Type Interferometer—or respectively one plane parallel plate in each interferometer arm with a slightly unequal thickness—the optical path difference OPD can be preferably made unequal to zero for the main beams. For a given detector, the spectral resolution can then in the known manner be increased by a factor of almost two with an asymmetric position of the spatial interferogram on the raster detector.

On the Fourier transformation spectrometer with Michelson-Type Interferometer, the beam splitter of this interferometer is in this case preferably formed as an amplitude beam splitter. This is preferably a planar beam splitter layer or a mylar foil or a lattice.

Using splitter layers, this beam splitter can be formed for the UV spectral range, for the visible range, for the near infrared range, for the mid-infrared range (MIR), or also for the far infrared range (FIR) using a mylar foil. For the terahertz range or the far infrared spectral range, a beam splitter can also be fabricated using a fine wire lattice structure, also known as a grid structure.

On the Fourier transformation spectrometer, at least one field of view discriminator is preferably mapped to the Michelson-Type Interferometer. In the simplest case, the field of view discriminator can be formed as a pinhole, that is to say as a very fine aperture opening. The field of view discriminator is preferably formed as a gap aperture or as a micro-mirror or as a narrow, elongated mirror.

On the Fourier transformation spectrometer, at least one field of view discriminator is preferably arranged in the Michelson-Type Interferometer. What was already written above for the field of view discriminator also applies for this field of view discriminator.

On the Fourier transformation spectrometer, at least one field of view discriminator is preferably arranged downstream of the beam splitter of the Michelson-Type Interferometer in the direction of light. What was already written above for the field of view discriminator also applies for this field of view discriminator.

On the Fourier transformation spectrometer, a field of view discriminator is preferably arranged in an interferometer arm in a real mirror surface. As already described, the real mirror surface is formed by the surface of an individual plane mirror in the arm of the Michelson-Type Interferometer. This is also where the focused image of the measured object is preferably generated. Due to its special shape, the plane mirror can in this case by itself affect the field of view discrimination, in that the latter is preferably itself formed very narrow or even as a micro-mirror.

A field of view discriminator can in this case preferably also be formed as a shading aperture applied on the plane mirror. But this shading aperture can preferably also be formed on the mirror as an imprint. The mirror can preferably also be formed as a linear or narrow two-dimensional array of micro-mirrors.

On a Fourier transformation spectrometer, a field of view discriminator is alternatively arranged in the first interferometer arm in a surface optically conjugated in relation to the apparent end mirror surface of the second interferometer arm. In an interferometer arm with three mirrors or three mirror surfaces in a periscope arrangement, the resulting apparent end mirror surface is located outside of the end mirror arrangement.

On an end mirror arrangement with an odd number of mirrors or mirror surfaces in a periscope arrangement greater than three, the optical distances are however generally significantly enlarged compared to an arrangement with three mirrors or mirror surfaces, thus reducing the opening angle, which is seen as technically rather not advantageous.

In total a generally even number of mirrors or mirror surfaces in the Michelson-Type Interferometer that each only have a single reflection in the beam path, and in this case for a generally odd number of mirrors or mirror surfaces in at least one arm of the interferometer, that is to say 3, 5, . . . 2n+1, where n is an integer, causes the wavefronts interfering on the Michelson-Type Interferometer to have the same orientation, and therefore to be not inverted. This is a crucial condition for generating spatial interferograms with high contrast and with a laterally expanded light distribution at the interferometer input.

On a Fourier transformation spectrometer, the field of view discriminator is preferably optically mapped to the apparent end mirror surface of the triple periscope arrangement. For this purpose, the field of view discriminator is preferably arranged between the first and the third mirror of said first triple periscope arrangement. Given a symmetrical arrangement, the field of view discriminator of the second mirror surface can preferably also be formed with a shading aperture applied on the mirror surface. The second mirror surface can preferably also be formed as a narrow mirror, so that a field of view discrimination occurs, given a focused image on the mirror surface.

The second interferometer arm preferably has a periscope arrangement as an end mirror arrangement with an odd number of mirrors or mirror surfaces equal to three or greater than three, in throat or W shape. These mirrors or mirror surfaces are generally arranged vertically in relation to the reference plane. In this second triple periscope arrangement, a second field of view discriminator is preferably arranged that is optically conjugated to the field of view discriminator in the first interferometer arm, and is preferably at least approximately formed geometrically equivalently to the first field of view discriminator. However, it is not mandatory that the geometry of the two periscope arrangements is equivalent.

On the Fourier transformation spectrometer, a triple periscope arrangement is preferably arranged in each arm of the interferometer of the Michelson-Type Interferometer, and the field of view discriminator is at least approximately mapped to the second mirror or the second mirror surface of the triple periscope arrangement.

On the Fourier transformation spectrometer, this second mirror or this second mirror surface is preferably formed narrow in a direction parallel in relation to the reference plane, and thus discriminates the field of view. On the second mirror or the second mirror surface, respectively also an at least approximately focused image of the object is at least approximately formed using a focusing imaging system at the location of at least one triple periscope arrangement.

On the Fourier transformation spectrometer, a triple periscope arrangement is preferably arranged in each arm of the interferometer in the Michelson-Type Interferometer, wherein the lateral shear is added, that is to say the value of the latter is added. A particularly large lateral shear can then be generated given a moderate construction size for each individual triple periscope arrangement.

On the Fourier transformation spectrometer, a triple periscope arrangement is preferably arranged in each arm of the interferometer in the Michelson-Type Interferometer, wherein the lateral shear is largely compensated, that is to say the value of the latter is subtracted. A particularly small lateral shear can then be achieved largely independently of the field of view width.

A plurality of spatial interferograms can be generated by a field of view discriminator formed elongated in a direction vertically in relation to the reference plane RE. This direction is in this case defined as the height direction, which in this case is the x direction. There is exactly only one spatial interferogram for each x value. Given a plurality of spatial interferograms, and given knowledge of the x value for each spatial interferogram, the spectrum is calculated by means of Fourier transformation from each spatial interferogram, and is mapped to an image point in x direction. They value is determined from the current relation between the object and the field of view discriminator, and from the geometric embodiment of the field of view discriminator. Given a gap-shaped embodiment of the field of view discriminator with a vertical position of the gap in relation to the reference plane, the same y value is assigned to each of the spatial interferograms for a recording using a raster detector. The optical interference is reduced when using a field of view discriminator with a preferred arrangement of pinholes in a zig-zag line. For each x value, there is then only exactly a single pinhole, and therefore exactly only a single spatial interferogram, and the spectrums are mapped to the corresponding images of the pinholes in x and y direction.

On a Fourier transformation spectrometer, a second field of view discriminator is preferably arranged in the second interferometer arm, wherein said second field of view discriminator is optically conjugated in relation to the field of view discriminator in the first interferometer arm and is at least approximately formed geometrically equivalent to the first field of view discriminator.

On the Fourier transformation spectrometer, at least one field of view discriminator is preferably arranged directly upstream of the Michelson-Type Interferometer.

The field of view discriminator can preferably be formed as a gap aperture or in reflection as a narrow mirror or mirror surface area.

The field of view discriminator can preferably be formed as a rigid arrangement.

The field of view discriminator can preferably be formed as a moving arrangement in rotation or translation.

The field of view discriminator can preferably also be formed as a rigid or as a moving pinhole array.

The field of view discriminator can preferably also be formed as a spatial light modulator.

On the Fourier transformation spectrometer, at least one field of view discriminator is preferably mapped to the image of a measured object in the beam path in the Michelson-Type Interferometer. This image is formed by means of an upstream lens as an imaging system upstream of the Michelson-Type Interferometer. The field of view discriminator can preferably be formed as a gap aperture or in reflection as a narrow mirror or mirror surface area. On a Fourier transformation spectrometer, a first field of view discriminator is preferably mapped to the end mirror and a second field of view discriminator is mapped to the triple periscope group.

On a Fourier transformation spectrometer, the field of view discriminator is preferably formed by the end mirror or by a mirror of the triple periscope group arrangement. The end mirror or a mirror of the triple periscope group is in this case preferably formed comparatively narrow.

On the Fourier transformation spectrometer, at least one field of view discriminator is preferably formed as a raster mirror or as a raster mirror surface.

On the Fourier transformation spectrometer, computer-controllable motion elements are preferably mapped to the elements of the raster mirror or the raster mirror surface.

On a Fourier transformation spectrometer, given a placement of respectively one field of view discriminator in each interferometer arm of the Michelson-Type Interferometer, said two field of view discriminators are preferably arranged optically conjugated in relation to each other.

On the Fourier transformation spectrometer, at least one field of view discriminator is preferably formed as a gap-shaped shading aperture.

On the Fourier transformation spectrometer, at least one field of view discriminator is preferably formed as a micro-gap shading aperture array.

The field of view discriminator can preferably be formed as a micro-gap shading aperture array as a moving arrangement in rotation or translation.

On the Fourier transformation spectrometer, at least one field of view discriminator is preferably formed as a pinhole shading aperture.

The pinhole shading aperture can preferably be formed as a moving arrangement in rotation or translation. The pinhole shading aperture can in this case preferably be formed as a rotating circular desk with preferably only one track of pinholes. The pinhole shading aperture can preferably be illuminated in order to illuminate the object with preferably fine white spots using mapped imaging optics, with the direction of light pointed away from the interferometer. This represents an incident light arrangement. These mapped imaging optics are preferably formed as a microscopic imaging stage. The images of the fine white spots of the object on the return path of the light, that is to say with the direction of light toward the interferometer, are preferably confocally discriminated on the pinholes of the pinhole shading aperture, which is preferably formed as an aperture disk, in order to minimize the scattered light from the measured object in the known manner, and to largely mask the light outside of the depth of field focal range of the light spots. A relative motion can preferably be performed in the depth axis between the measured object and the Fourier transformation spectrometer in order to obtain depth-resolved spectrums, that is to say spectrums that are also mapped to a position along the depth axis in the measured object. It is then possible—either by the combination of lateral movement of the pinhole shading aperture or a lateral relative movement between the measured object and the Fourier transformation spectrometer, and also a relative motion in the depth axis between the measured object and the Fourier transformation spectrometer—to map spectral information to spatially distributed points in the measured object, so that a four-dimensional data set with three spatial coordinates is created. This approach represents the combination of a confocal microscope with the Fourier transformation spectrometer according to the invention. For the terahertz range or for the far infrared range, this described combination with confocal discrimination can also be scaled toward a coarser resolution, such that the light spots in the object region can then preferably lie in the order of magnitude of one millimeter or respectively also preferably in the tenth of a millimeter range.

In particular in the terahertz range or in the far infrared range, the measured object can be preferably structurally illuminated with fine light spots for transmitted light arrangements, and a confocal discrimination can be performed with a field of view discriminator. The confocal discrimination can in this case occur upstream of the interferometer, but also in the interferometer. In the latter case, a field of view discriminator is then preferably arranged in the interferometer in each arm of the interferometer, wherein the two field of view discriminators are optically conjugated in relation to each other.

The field of view discriminator can preferably also be formed as a spatial light modulator.

It is noteworthy in this case that the term "light" is herein used as a synonym for electromagnetic radiation, also in the infrared, far infrared, and in the terahertz range, and therefore represents no restriction to the visible spectral range.

On the Fourier transformation spectrometer, at least one field of view discriminator is preferably formed as a one-dimensional or two-dimensional pinhole shading aperture array in the form of an aperture disk. This aperture disk can preferably be used for confocal discrimination. This aperture disk can preferably be arranged rigidly, or can be formed to rotate with motion devices.

On the Fourier transformation spectrometer, a micro-gap shading aperture array is preferably formed with micro-gaps in a laterally shifted arrangement.

On the Fourier transformation spectrometer, the micro-gap shading aperture array is preferably formed with mechanically moving elements.

On the Fourier transformation spectrometer, a fine structured field of view discriminator in gap shape or in dotted line shape is preferably mapped to the measured object or to the field of the light source. Individual, fine object regions of particular interest can then be recorded in order to form respectively one spatial interferogram from the light that only originates from said object regions. The lengthwise direction of the field discriminator is in this case aligned vertically in relation to the reference plane RE.

On the Fourier transformation spectrometer, the light source itself is preferably formed in fine structured gap-shape or in the form of preferably fine luminescent elements in a straight line or in a zigzag line, and the lengthwise direction of said light source, which represents the x direction, is aligned vertically in relation to the reference plane RE. An arrangement of luminescent elements in a zigzag line generally reduces the optical interference based on the larger distance of the luminescent elements in comparison to an arrangement of the elements in a straight line.

On the Fourier transformation spectrometer, the field of the measured object and the field of the light source are preferably arranged optically conjugated in relation to each other at least in a partial region.

On the Fourier transformation spectrometer, the Michelson-Type Interferometer is preferably formed as an air type or a prism type, or as a hybrid air-prism arrangement.

On the Fourier transformation spectrometer, a confocal arrangement is preferably arranged upstream of the Michelson-Type Interferometer. Scattered light from a light scattering sample can then be kept away, and a depth discrimination can also be achieved in the measured object.

On the Fourier transformation spectrometer, the confocal arrangement is preferably formed with a rigid aperture disk or with a rotating aperture disk upstream of the Michelson-Type Interferometer. In this case, any form of field of view discrimination is omitted in the Michelson-Type Interferometer itself, because said field of view discrimination is already effectively given by the confocal arrangement.

On the Fourier transformation spectrometer, the confocal arrangement is preferably formed with a spatial light modulator in reflection or transmission. This spatial light modulator is preferably formed as a digital micro-mirror array or as a liquid crystal display.

On the Fourier transformation spectrometer, the confocal discriminator elements that [ . . . ] the upstream confocal arrangement [ . . . ] are preferably at least approximately optically conjugated with at least one effective mirror surface in the arm of a Michelson-Type Interferometer. The confocal discriminator elements are preferably formed as pinholes or as micro mirrors, preferably also as controllable micro mirrors of a digital micro mirror array.

On the Fourier transformation spectrometer, preferably at least one field of view discriminator (BFD) is formed in the Michelson-Type Interferometer as a controllable spatial light modulator in reflection.

On the Fourier transformation spectrometer, preferably at least one field of view discriminator (BFD) is formed in the Fourier transformation spectrometer system as a controllable spatial light modulator in transmission.

A relative movement between the measured object and the mobile measurement head preferably also occurs in the depth axis. For this purpose, motion devices in the depth axis are mapped to the measured object or the mobile measurement head. Motion devices in the depth axis are preferably also mapped to a component of the mobile measurement head.

However, an imaging component of the mobile measurement head can preferably also be formed with variable refractive power, for example as a computer-controllable liquid lens.

Spectrums with associated depth information can then be obtained in the close-up region of the comparatively small measured object or a small region of the latter. For this purpose, firstly, a fine structured illumination preferably occurs of the measured object as incident light or in transmission using a preferably elongated light spot pattern. Secondly, image points of pinholes of a confocal arrangement formed as a component of the mobile measurement head can in this case preferably also illuminate the measured object.

DESCRIPTION OF THE FIGURES

The following describes the details of several exemplary embodiments, wherein the invention is not restricted to the described exemplary embodiments. Individual features described in a particular embodiment can be arbitrarily combined, provided they do not exclude each other. Moreover, various features provided together in the exemplary embodiments are not to be seen as restricting the invention.

A description of the drawing follows, and the exemplary embodiments show:

FIG. 1 is a schematic side view of an exemplary use of an exemplary FT spectrometer on a patient;

FIG. 2 is a schematic reverse imaging of an exemplary use of an exemplary FT spectrometer on a patient;

Figure 3:
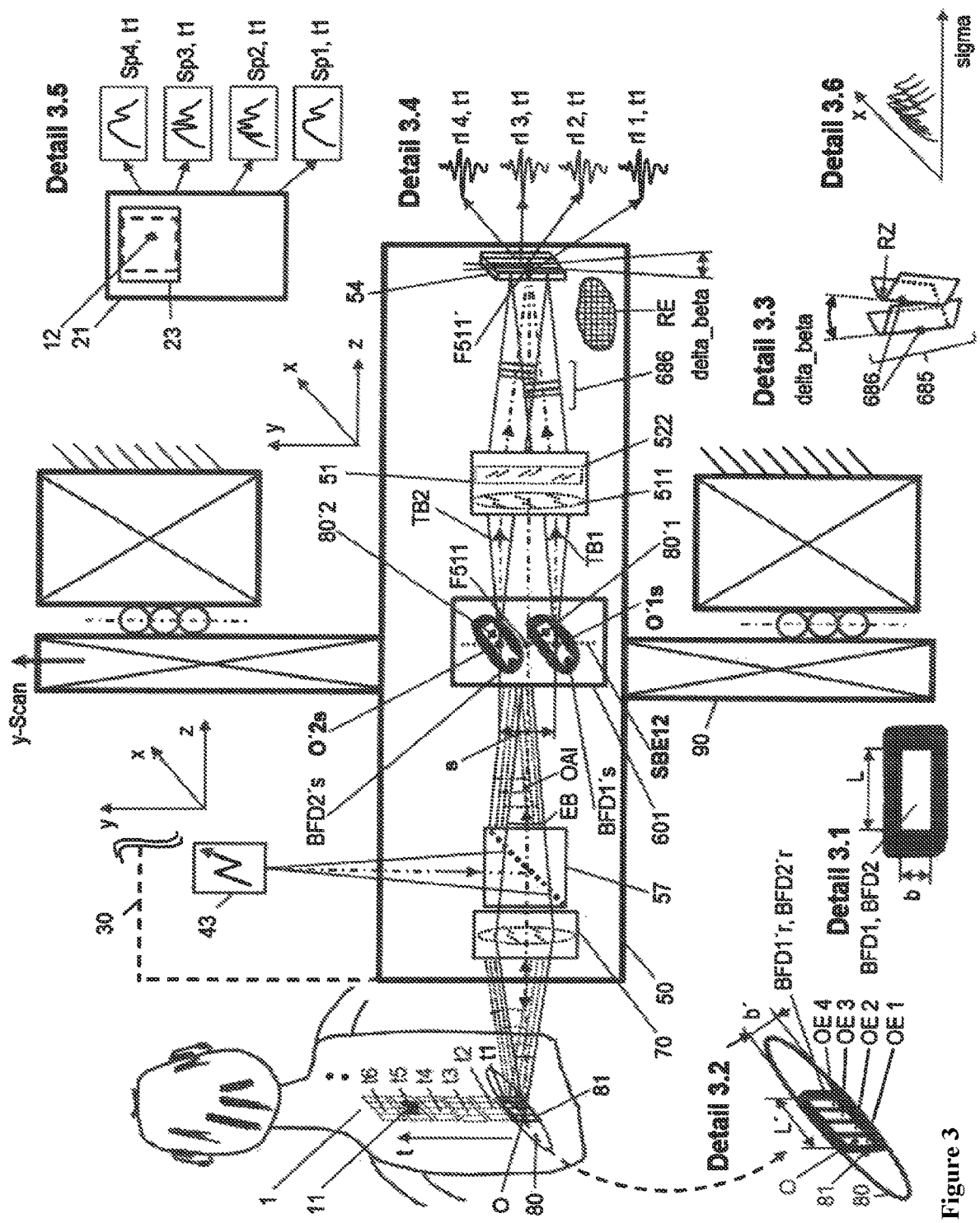
FIG. 3 is a schematic view of an exemplary FT spectrometer, in particular of a single shot line spectrometer.

A description is provided by means of 20 Figures and by means of three exemplary embodiments without a figure (not shown schematically based on a drawing). In the description to follow, the term 'light' is generally used as a synonym for electromagnetic radiation from the UV up to the terahertz range, including thermal radiation.

The term "spectrometer system" used herein in particular relates to a compact single shot Fourier transformation spectrometer with a Michelson-Type Interferometer that generates a lateral shear s. This can in particular either be based on an active illumination of the measured object, which preferably can also represent a structured illumination, or the measured object is self-luminescent. The term "single shot" used herein relates to obtaining spatial interferograms using double beam interferometry.

For a single shot method, the detector—in this case generally a raster matrix detector in the FT spectrometer—respectively records a single image after an external or internal digital start command for the matrix detector. Using Michelson-Type Interferometers, a plurality of spatial interferograms arranged next to each other are generated on the matrix detector. For typical matrix detectors, the number of such spatial interferograms is in the order of magnitude from one-hundred to one-thousand. The spatial interferograms on a camera image generally respectively belong to a linear partial region of the measured object. This at least represents a selected partial region of the measured object by means of spatial discrimination. Fast Fourier Transformation (FFT) is employed to numerically compute the spatial interferograms into spectrums, where appropriate, also only after interim storage. Fast Fourier-Transformation (or fast Fourier transform, and therefore typically abbreviated as FFT) is an algorithm for efficiently calculating the Discrete Fourier Transformation (DFT).

The recording time—or the time window for the single shot—is in this case generally determined by the integration time (more generally: image recording time) of the raster matrix detector, which depending on the detector type and light conditions can extend from the single-digit microsecond range up to the three-digit millisecond range. In an extreme case, the integration time can also extend up to the single-digit second range at extremely low light energy and comparatively very low dynamics in the measured object. But for flash illumination or pulsed illumination of the measured object—synchronization implied—the flash or pulse duration determines the time window for the single shot and analogously also the opening time of a controlled aperture, provided that the latter are respectively shorter than the aforementioned integration time of the matrix detector.

Several recordings of the raster detector array in the fastest possible sequence, for example with a recording frequency of 60 Hz, then result in a plurality of adjacent, generally linear partial regions of a measured object, so that a spectrum can be incrementally generated by means of relative motion for each resolvable surface increment of a surface-based measured object, thus resulting in a hyperspectral image. The achievable lateral resolution in the hyperspectral image is in this case—as known—determined by the parameters of the optical components in the imaging system and potentially also from the raster constant of the (raster) matrix detector of the FT spectrometer. Late-model high-speed matrix detectors also permit integration times (image recording times) in the range of 10 microseconds, possibly also less than that.

FIG. 1 shows a use of an exemplary FT spectrometer. FIG. 1 is a schematic illustration, in particular of an arrangement of a patient with safety goggles, wherein a medically conspicuous skin feature 2 on the back 1 of the patient is to be examined. In particular, the diagnostics are tasked to determine whether the skin feature 2 is a birthmark or a melanoma. The diagnostic procedure is to be validated as objectively as possible, in particular also by means of a spectral measurement, using a spectrometer system 20. For this purpose, the dermatologist can for skin screening make use of an essentially mobile measurement head 30 in single shot mode, which is formed as a handheld device for scanning over a measured object, in this case the region of a back 1. This device is in particular mapped to a pulsed NIR light source 40 for essentially active illumination in stripe shape and/or for a fine structured illumination of the back 1 and an optics unit 50 with an integrated Michelson-Type Interferometer 601.

This essentially mobile measurement head 30 is in particular guided relatively slowly by hand, e.g. with a speed of approximately v=1 cm/s over the back 1 of the patient, here from bottom to top, or in +y direction.

Although not shown here, a VIS monitoring camera is integrated in this case in the mobile measurement head 30 for diagnostic purposes of the skin surface on the back 1. The imaging data recorded with this monitoring camera is in particular additionally used to support the construction of a hyperspectral image, in particular when the scan movement of the mobile measurement head 30 by hand is essentially not performed at a constant speed. Two position markers not shown here are for this purpose applied on the back 1. The spatial interferograms rI incrementally collected during a moderate movement of the mobile measurement head 30, and which are generally obtained in single shot mode using an InGaAs camera 54 for the near infrared spectral range, in this case along a line in horizontal direction, are in particular converted into spectrums SP and can be assembled into a hyperspectral image set. The InGaAs camera 54 and likewise the pulsed NIR light source 40 is preferably controllable by the computer 21. These two components (40 and 54) are synchronized by the computer 21.

The spatial interferograms rI generally recorded in a single shot using an interferometer 601 and can therefore be computationally processed into spectrums along this line preferably using a program 101 to execute fast Fourier transformation (FFT). This is in particular done line by line, or in rows, for the skin region selected on the back 1, which can be recorded in the width of the optics unit 50 of the mobile measurement head 30. After the recording of spatial interferograms rI is completed in an upward motion that covers the skin region of diagnostic interest, the calculated spectrums can be mapped point by point to an image map of the examined skin region, so that a hyperspectral image is built step-by-step. It is in this case seen as admissible when not perfectly or not optimally uniform, and not perfectly laterally guided hand motions of the dermatologist while using the mobile measurement head 30 causes the image point raster to have certain elongated and compressed areas, but is without gaps. Using a program 22 for analyzing the spectrums SP, executed on a high-performance computer 21 and/or a computing system, in particular risk and high-risk regions can be identified based on the spectral signatures of the spectrums SP.

In this case, algorithms for spectrum analysis, for example based on the Principal Component Analysis approach, can be used or approaches with artificial intelligence can also be candidates. The algorithms for analyzing the spectrums for purposes of assessing a tumor risk are not an area of focus for purposes of this invention, because the present invention in particular relates to the fast provisioning of optical primary data, or spatial interferograms rI. The results of the analysis of the spectrums can be shown on a monitor 23.

Different than shown in FIG. 1, the illumination can in a further exemplary embodiment 1 (not shown schematically based on a drawing) essentially be performed coaxially by coupling in the light using a beam splitter. Only then can a projected light stripe and the measurement field essentially at all times overlap based on an arbitrary position of the measurement field. A zoom function can then also essentially readily be integrated into the optics unit 50 of the mobile measurement head 30. The approach with coaxially coupling in the light to illuminate the back 1 is for example used in FIG. 3.

FIG. 2 shows a schematic illustration of the back view of the patient. The projected exemplary light stripe 80, which is created on the back 1 of the patient using an NIR stripe light source, is significantly longer than the measurement field 81 of the optics unit 50 of the mobile measurement head 30. The length of the measurement field 81 is L'. The measurement field is then essentially fully illuminated even for moderate distance changes of the measurement head 30. During measurement, the mobile measurement head 30 can be moved, in particular by hand and laterally across a region of the back. In this case, using the Michelson-Type Interferometer 601, the optics unit 50 can constantly record spatial interferograms rI in single shot mode, wherein the light source 40 can generate a synchronized flash light for the purpose of illuminating the measurement field 81 in the shape of a stripe 80. Because FIG. 1 shows a straight-ahead arrangement, that is to say an essentially unfolded arrangement, the coordinate directions y and x on the back 1 of a person correspond to those of the Michelson-Type Interferometer 601. Such a mobile measurement head 30 can during a surgical procedure under sedation also be used for tissue differentiation.

FIG. 3 shows the principle for the approach for a single shot line spectrometer with an illumination of the back 1 of a person with a stripe 80. A y scan can be executed here using a transport carriage 90 with a stepper motor drive not shown here. This y scan of the mobile measurement head 30 can in particular the executed laterally to the stripe 80 across the back 1 of a person sitting still. The back 1 can in this case be subject to essentially intense illumination in the form of a stripe 80 using a pulsed stripe light source 43. In this example, a coupling beam splitter cube 57 is used to coaxially couple the light into the optics unit 50 of the mobile measurement head 30. The measurement field 81 can then be illuminated with stripes 80. The region on the back 1 illuminated in this manner can be rendered by using an upstream lens 70, essentially in focus into the Michelson-Type Interferometer 601 by a plurality of individual beams. In particular, one beam can be associated with each object point. A representative beam is shown with solid lines, where the beam can belong to an object point O on the optical axis. Three further beams, representing a plurality of beams, are drawn as dotted lines in FIG. 3.

In this case, telecentricity applies at least approximately for the object rendering on the side of the upstream lens 70 facing the Michelson-Type Interferometer 601 with the optical axis OAI, however, a telecentricity aperture is not shown here. The upstream lens 70 can further have an autofocus function. The object distance determined with the latter can be constantly handed over or transmitted by the autofocus function to the analysis program as information during the recording, because a distance change changes the imaging scale during in the imaging, which is preferably taken into account during the analysis and rendering of the hyperspectral image. The Michelson-Type Interferometer 601 generates a lateral shear s, and in each of the two interferometer arms has a field of view discriminator BFD1 and BFD2 of respectively equal construction, which are shown in the detail FIG. 3.1 as the field of view discriminators BFD1 and BFD2 with the respective width b and the length L. FIG. 3 shows a symbolic illustration (additionally rendered visible by rotating out in perspective) of the apparent images BFD1's and BFD2's of the field of view discriminators BFD1 and BFD2 in the likewise symbolically illustrated Michelson-Type Interferometer 601 in the apparent image plane SBE12. At least one point each of one of these apparent images BFD1's and BFD2's of the field of view discriminators BFD1 and BFD2 is conjugated with respectively one apparent image point O'1s and O'2s of the object point O, wherein the apparent image points O'1s and O'2s are optically conjugated, or capable of interference, in the Michelson-Type Interferometer 601 by beam splitting, and, given that the Michelson-Type Interferometer 601 is accurately adjusted, essentially lie together in the apparent image plane SBE12—but separated by a lateral shear s. For the downstream anamorphic lens 51, the apparent image plane SBE12 in turn represents the object plane. Pairs of essentially coherent partial beams are created at the output of the double beam interferometer 601 that are shown here as examples in the figures as two partial beams TB1 and TB2, which are however generally representative for a plurality of partial beams.

The two field of view discriminators BFD1 and BFD2 are arranged in the double beam interferometer 601 such that the latter are optically conjugated, e.g. that they are optically no longer differentiatable as seen from the input of the interferometer into the interferometer. The field of view discriminators BFD1 and BFD2 are in this case expanded laterally such that in spite of discrimination, several beams of several object points can nevertheless pass these. It is implied that one point is always mapped to one beam. An image 80'1 is created on the field of view discriminator BFD1 by imaging, and an image 80'2 of the stripe 80 is generated on the field of few discriminator BFD2 by imaging. In each interferometer arm, essentially only part of the light from each of these two images 80'1 and 80'2 can pass the discriminators BFD1 and BFD2 with a field of width b and length L. This part of the light is the selected part of the light. Light outside of this field is excluded from the further imaging, and is therefore desirably lost. The reverse imaging of the two field of view discriminators BFD1 and BFD2 determines the width of the measurement field b' and their length L' on the back 1 with the imaging scale of the upstream lens 70.

The detail FIG. 3.2 shows the measurement field 81 with width b' and length L'. As examples and as representatives for many object elements, the detail FIG. 3.2 in this case only shows four object elements with appropriately small surface area, namely OE1 to OE4, with an increased height for better visibility. The actual number of object elements is however typically in an order of magnitude of approximately 500 in the MIR spectral range, with the appropriate use of an MIR camera with approximately about 500 pixels in x direction. For every object element OE, the measurement method determines exactly one spectrum SP when this object element OE is sufficiently cooperative for a measurement. The width of the measurement field b' on the back 1 is in this case approximately 0.2 mm. The width of the measurement field b' can in particular range between approximately 0.05 mm and 20 mm. Moreover, the detailed FIG. 3.2 indicates the two coincidental real images BFD1'r and BFD2'r of the two field of view discriminators BFD1 and BFD2 that are created by imagined or fictitious reverse imaging on the back 1 using the upstream lens 70.

The illuminated field of view discriminators BFD1 and BFD2, which essentially represent two coherent light sources, are rendered on the output of an anamorphic lens 51 arranged downstream of the Michelson-Type Interferometer 601, wherein the lens 51 is also preferably chromatically corrected. The imaging of the object 51, which is formed with a rotational component 511 and also with a cylindrical component 512, generates respectively essentially two cylindrical waves tilted toward each other, which here are projected onto a detector as a raster detector, in particular onto an InGaAs camera 54, wherein each pair of cylindrical waves respectively forms one spatial interferogram rI that is mapped to an object element OE. The cylindrical wavefronts 385 are shown in the detail FIG. 3.3 with the peak lines 386 that are tilted towards each other by delta beta. This special optical function of the anamorphic lens 51 is visualized in the illustrations in FIG. 13 and FIG. 14. The accurate adjustment of interferometer, including a matching of the optical distances of the arms of the Michelson-Type Interferometer 601 is known. It is noteworthy in this case that due to the comparatively low value of the width b of approximately 0.2 mm, the requirements for adjusting an end mirror or a triple periscope group in the Michelson-Type Interferometer 601 are not very high in the present case, which represents a special advantage regarding ruggedness, for example in rough ambient conditions and with comparatively fast temperature changes. The lower the selected value b, the less critical the adjustment of the interferometer 601. Even a tilt of an interferometer mirror about a tilt axis in the Michelson-Type Interferometer 601 that is parallel in relation to the reference plane RE is comparatively noncritical. This insensitivity is the product of the spatial resolution of the spatial interferograms rI using the raster receiver. The detail FIG. 3.4 shows several spatial interferograms rI.

The somewhat varying optical path differences of the field of view in the spatial interferograms rI caused by a not entirely perfect adjustment of the interferometer 601 do not present a problem for the numerical analysis of the spatial interferograms rI, given the prior art.

A high signal-to-noise ratio can only be achieved in the spectrum when the contrast of the spatial interferograms rI is sufficiently good. It is therefore very important that the interferometer hardware ensures a highest possible contrast of the spatial interferograms rI, because the search for spectral signatures, in particular in biological measured objects, are already frequently not significantly pronounced.

The field of view discriminators BFD1 and BFD2 in this exemplary embodiment according to FIG. 3 can also be narrow mirrors of width b and with a large length L. Light outside of the mirror is trapped by light traps or by matte-black masking on the narrow mirror, the masking having the width b.

The detail FIG. 3.5 shows calculated spectrums Sp1 to Sp4 from an exemplary recording. According to the detail FIG. 3.5, said spectrums are in this case mapped to the x coordinate according to detail FIG. 6. Using a y scan of the [ . . . ], the known data cube can be determined in the form (x, y, wave number) or (x, y, wavelength) for a region of the back 1.

In a further exemplary embodiment 2 (no figure), a multi-axis robot arm is used to move the mobile measurement head 30. The latter creates significantly greater flexibility than a linearly operating transport carriage 90, and frequently presents major advantages for a surgical procedure due to its flexible local positioning.

Figure 4:
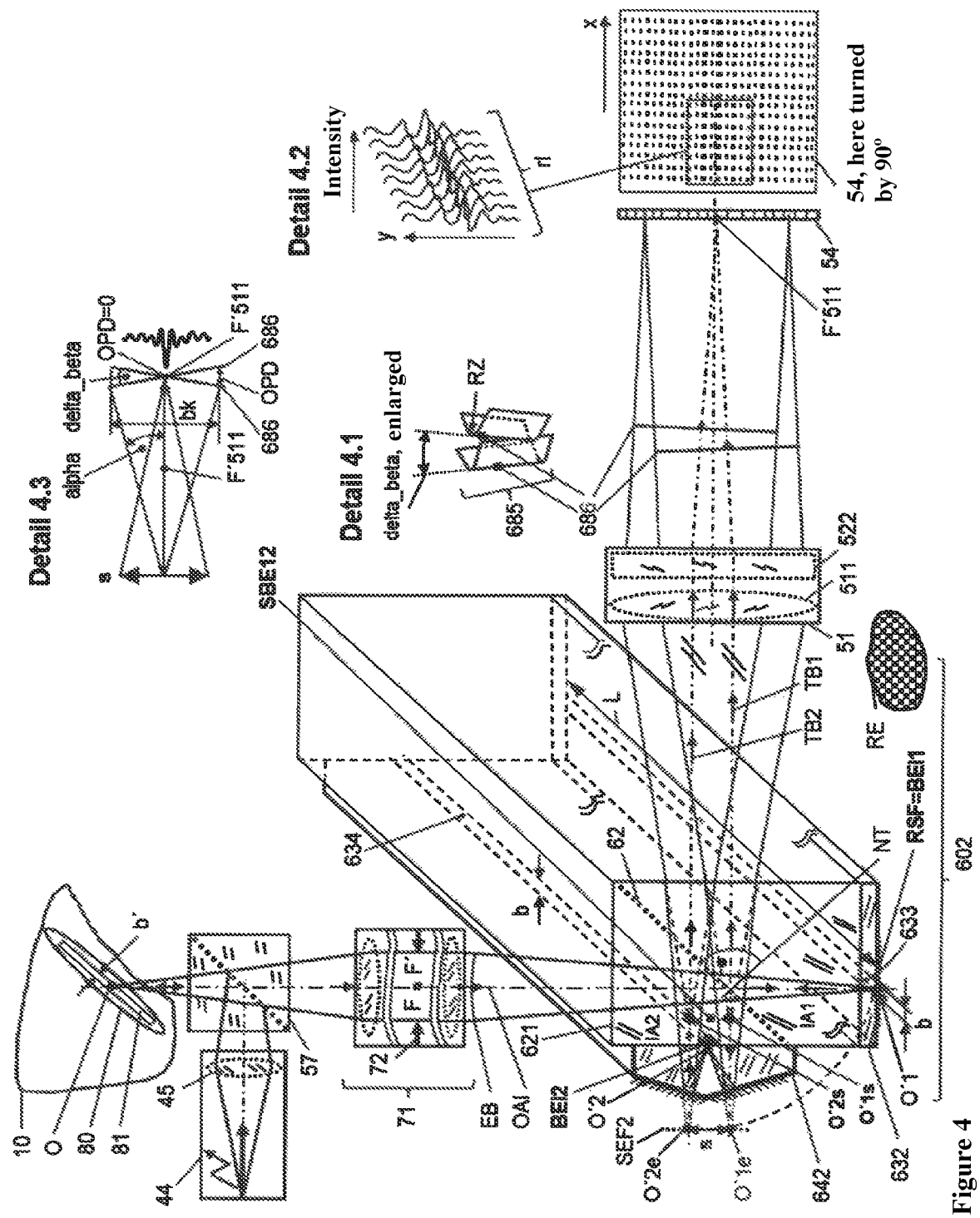
FIG. 4 is a schematic view of an exemplary Michelson-Type Interferometer.

FIG. 4 shows a particularly compact exemplary Michelson-Type Interferometer 602 that is in particular designed for the NIR range. The interferometer arrangement shown here is formed rather elongated so that—given the corresponding upstream and downstream lenses 71 and 51 (which are shown here at a reduced scale for illustration purposes)—the comparatively long measurement field of length L, in particular formed elongated in the x direction, can be recorded in a single shot. The pulsed light source 44 is in particular used to project a matching long stripe 80 onto the measured object 10, for example having a length of 20 mm; the pulsed light source 44 is for this purpose equipped with integrated imaging optics 45. Using a coupling beam splitter 57, the light is essentially coaxially coupled into the illumination beam path and illuminates the measured object 10 in the form of a light stripe 80. After yet again passing the coupling beam splitter 57, the light originating on the axis from a light point O (representative for the luminescent object points) of the illuminated measured object 10 enters the Michelson-Type Interferometer as transmitted light through the tele-centric imaging stage 71 as the essentially focused incident beam EB. The imaging stage 71—shown here only symbolically and at rather small scale—has a telecentric aperture 72 in the coincidental focus planes. The Michelson-Type Interferometer 602 is in this case formed by means of a cemented glass block 621, which in this case is however shown greatly enlarged, with a beam splitter layer 62. The beam is split on said beam splitter layer into the two arms IA1 and IA2 of the Michelson-Type Interferometer 602. As the partial beam passes through, it is projected in the arm IA1 onto the narrow plane mirror 633 with an outer protective layer that is applied onto a mirror plate whose thickness is adjusted. The plane mirror 633 essentially defines the real mirror surface RSF, which essentially matches the plane mirror 633.

This plane mirror 633 is positioned in the image plane in the Michelson-Type Interferometer 602 as a part of the illuminated measured object 10 is rendered, and represents the first field of view discriminator BFD1, whose reverse imaging determines the measurement field 81 on the measured object 10.

The partial beam reflected on the beam splitter layer 62 enters the triple periscope group 642, formed on an exemplary basis as a prism arrangement in W shape, in which the narrow mirror 634 is located. This narrow mirror 634, with an exemplary width of 1 mm, is positioned in the image plane in the Michelson-Type Interferometer 602 when the measurement field illuminated by stripe 80 is rendered. This mirror 634 represents the second field of view discriminator and whose reverse imaging determines the measurement field size on the measured object 10 because the two mirrors are located in positions that are optically conjugated in relation to each other. Moreover, these mirrors 633 and 634 are designed significantly wider than the Airy disk, for example with a width of up to 1 mm, so that comparatively large amounts of light can be detected, thus facilitating fast measurements, for example with an image recording rate of 100 Hz. A field of view discrimination or restriction then occurs directly in the Michelson-Type Interferometer 602. If needed following a very high lateral resolution, for example of 0.1 mm on the object, two very narrow mirrors 633 and 634, for example with a width of significantly less than 0.1 mm, can also be used as field of view discriminators.

The light reflected as the partial beam TB1 by the narrow mirror 633 and the partial beam TB2 returning or reflected back by the triple periscope group 642 now with a lateral shear s, travels through an anamorphic imaging stage 51—also with cylindrical component 522—and are caused to interfere with the cylindrical waves 685. These cylindrical waves 685 are shown in the detail FIG. 4.1 and are used to generate spatial interferograms rI. The spatial interferograms rI are detected using a detector, preferably using an InGaAs camera 54 for the NIR range. The angle delta_beta between the interfering cylindrical wavefronts 685, that is to say the angle delta_beta between the two peak lines 686, is shown here in greatly enlarged form. The light from the coherent and apparent light source points O'1s and O'2s in the apparent image plane SBE12 respectively generates a spatial interferogram rI. This spatial interferogram rI is in this case essentially centered on the chip of the InGaAs camera 54, because in this case—given the corresponding adjustment of the interferometer—the location with the optical path difference is approximately zero in the center of the chip. Here, the spatial interferometer rI is accurately matched in the two interferometer arms IA1 and IA2 with regard to its optical distances. A measured object scanning mechanism for the y direction is available, but is not shown here.

In contrast to spherical waves, the shapes of cylindrical waves represent sections of cylindrical surfaces with respectively one peak line.

The maximum achievable optical path difference (OPD) in the Michelson-Type Interferometer can be approximately calculated with the illustration in detail FIG. 4.3. When this case assumes a numerical aperture A=sin(alpha) of approximately 0.1, which in air corresponds to an aperture angle alpha of approximately 5.7 degrees and represents a comparatively small value, and given a lateral shear of approximately s=1.04 mm, this results in a maximum path difference OPD on the chip of the InGaAs camera 54 in the detection plane DE of the lens 51, of OPD=A*s or approximately 0.104 mm. The spatial interferogram is in this case essentially centered on the chip. Given an assumed triangular apodization of the intensity values of the spatial interferogram rI when calculating the spectrum using fast Fourier transformation, a spectral resolution of approximately 96 $cm^{-1}$ can be achieved with the reciprocal value of the optical path difference OPD, here approximately 1/0.102 mm. Given a wavelength of approximately 1000 nm, this corresponds to a spectral resolution in the wavelength region of approximately 9.6 nm. Given a focal length f' 511 of approximately 60 mm for the lens 511, the formula a=2A*f' 511 is used to approximately determine the required minimum edge length of the InGaAs camera 54 at approximately 15.0 mm. The InGaAs camera Goldeye P-032 SWIR from Allied Vision has a width bk of approximately 15.9 mm and a pixel pitch of approximately 25 μm, and approximately 636×508 pixels. Assuming compliance with the scanning theorem, a symmetrical, spatial interferogram rI can be fully recorded with the optical path difference of approximately 0.104 mm in the spectral range from approximately 900 nm to 1700 nm, because the interference stripes of the shortest wavelength of approximately 900 nm on the camera chip—here with a width of approximately about 52 μm—are wider than double the pixel pitch of this InGaAs camera chip. The interference stripe width can be approximated from the quotient f' 511 divided by the lateral shear s and multiplied with the respective wavelength.

Provided the physiological conditions are carefully observed, this arrangement can also be used to perform a measurement on the human eye.

When such an arrangement is appropriately modified, the spectrum of florescent light can also be measured, in particular when an excitation light source in the ultraviolet spectral range is used.

Figure 5:
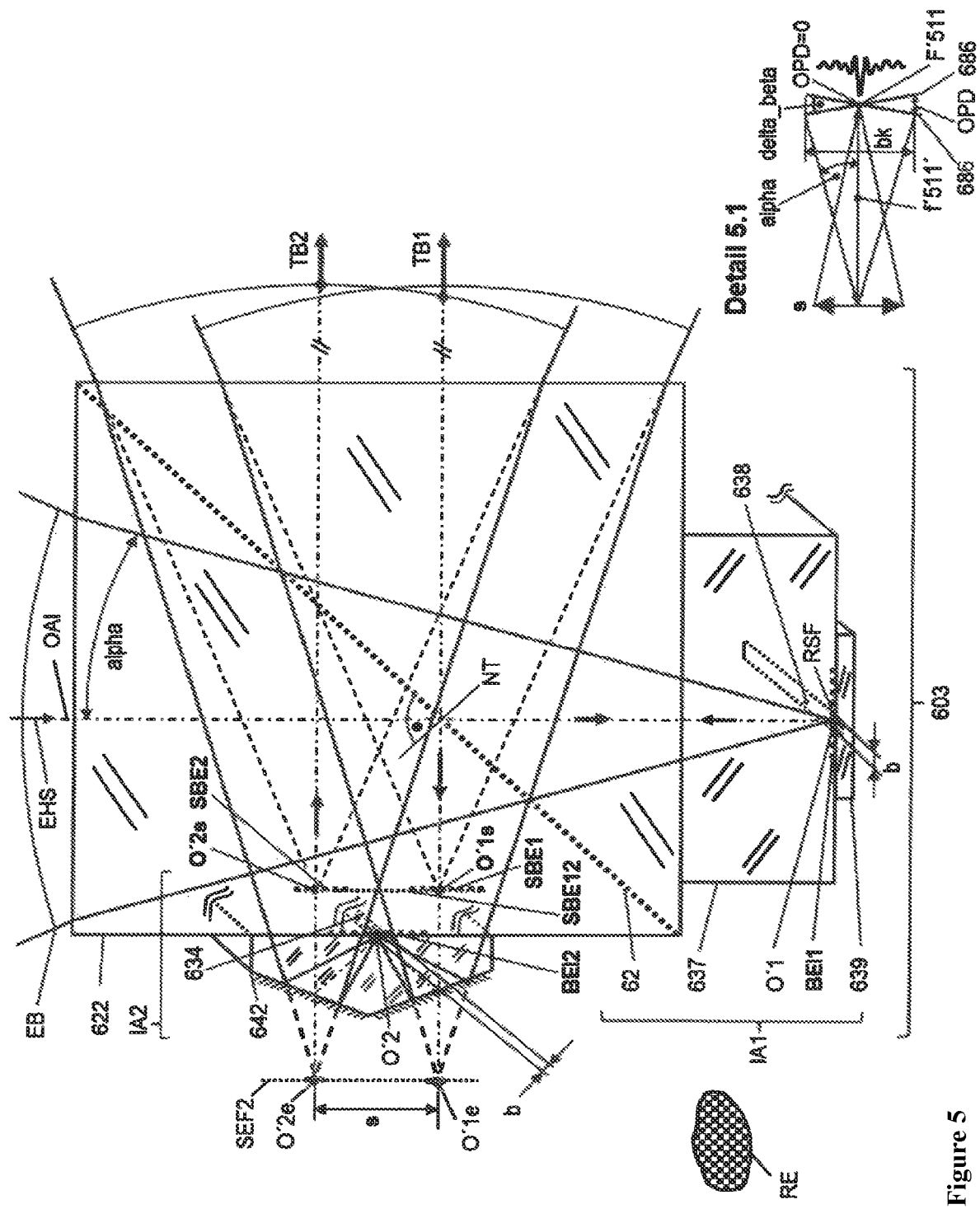
FIG. 5 is a schematic view of an exemplary Michelson-Type Interferometer.

FIG. 5 is intended to show the potential for a comparatively large aperture angle alpha of an incident beam EB of the arrangement with a beam splitter cube 622 and a compensation plate 637 with a narrow mirror surface 638. The narrow mirror surface 638, here for example with a width b of 0.2 mm, represents a real mirror surface RSF in the image plane BEI1 and is also the field of view discriminator BFD1 in the image plane BEI1. A triple periscope group 642 formed as a prism arrangement in W shape is for example arranged in the interferometer arm IA2. In this case, a maximum aperture angle of up to approximately 15 degrees is achieved in the Michelson-Type Interferometer 603, that is to say in the refractive material. This represents a comparatively large aperture angle. However, this can be achieved with an only narrow measurement field of width b of 0.2 millimeters. It is important to note that the stripe mirror 634 is essentially not arranged vertically in relation to the axis in the beam path, and a certain unfocused boundary of the measurement field can then occur in the interferometer arm IA2, in particular for large stripe widths b, for example above 0.2 mm.

The maximum achievable optical path difference (OPD) in the Michelson-Type Interferometer 603 can be computationally approximated using the illustration in the detail FIG. 5.1, wherein an application in the VIS range is assumed in this case. The anamorphic lens 51 (not shown here), see FIG. 13 and FIG. 14 in this regard, which contains the lens 511, is likewise designed for the visible spectral range. In this case, a CMOS camera 55 with approximately 20 million pixels is used for detection. The computational example in this case is based on a numerical aperture A=sin(alpha) in air of the anamorphic lens 51 of approximately A=0.2, which corresponds to an aperture angle alpha in air of approximately 11.5 degrees. Given a lateral shear of approximately s=1.6 mm, this results in the following maximum path difference OPD on the chip of the CMOS camera 55 (not shown here) in the detection plane DE of the lens 51 with OPD=A*s of approximately 0.32 mm. In this case, the spatial interferogram is centered on the chip of the CMOS camera 55. Given an assumed triangular apodization of the intensity values of the spatial interferogram rI when calculating the spectrum using fast Fourier transformation, a spectral resolution of approximately 31.3 $cm^{-1}$ can be achieved with the reciprocal value of the optical path difference OPD, here for example approximately 1/0.32 34 mm. Given a wavelength of approximately 400 nm, this corresponds to a spectral resolution in the wavelength region of approximately 0.5 nm. Given a focal length f' 511 of approximately 20 mm for the lens 511, the formula a=2A*f' 511 is used to determine the required minimum edge length of the CMOS camera 55 at approximately 8.0 mm. An exemplary CMOS camera with approximately 20 million pixels has a width bk of approximately 8 mm and a pixel pitch of approximately 2 µm, and approximately 4000 pixels, here in the width direction (y). Assuming compliance with the scanning theorem, a symmetrical, spatial interferogram rI can be fully recorded with the optical path difference of approximately 0.32 mm in the spectral range from approximately 400 nm to 900 nm, because the interference stripes of the shortest wavelength of approximately 400 nm on the camera chip—here with an interference stripe width of approximately about 5—are wider than double the pixel pitch of approximately 2 µm of this CMOS camera chip 55. The interference stripe width can be approximated from the quotient f' 511 divided by the lateral shear s and multiplied by the wavelength.

Figure 6:
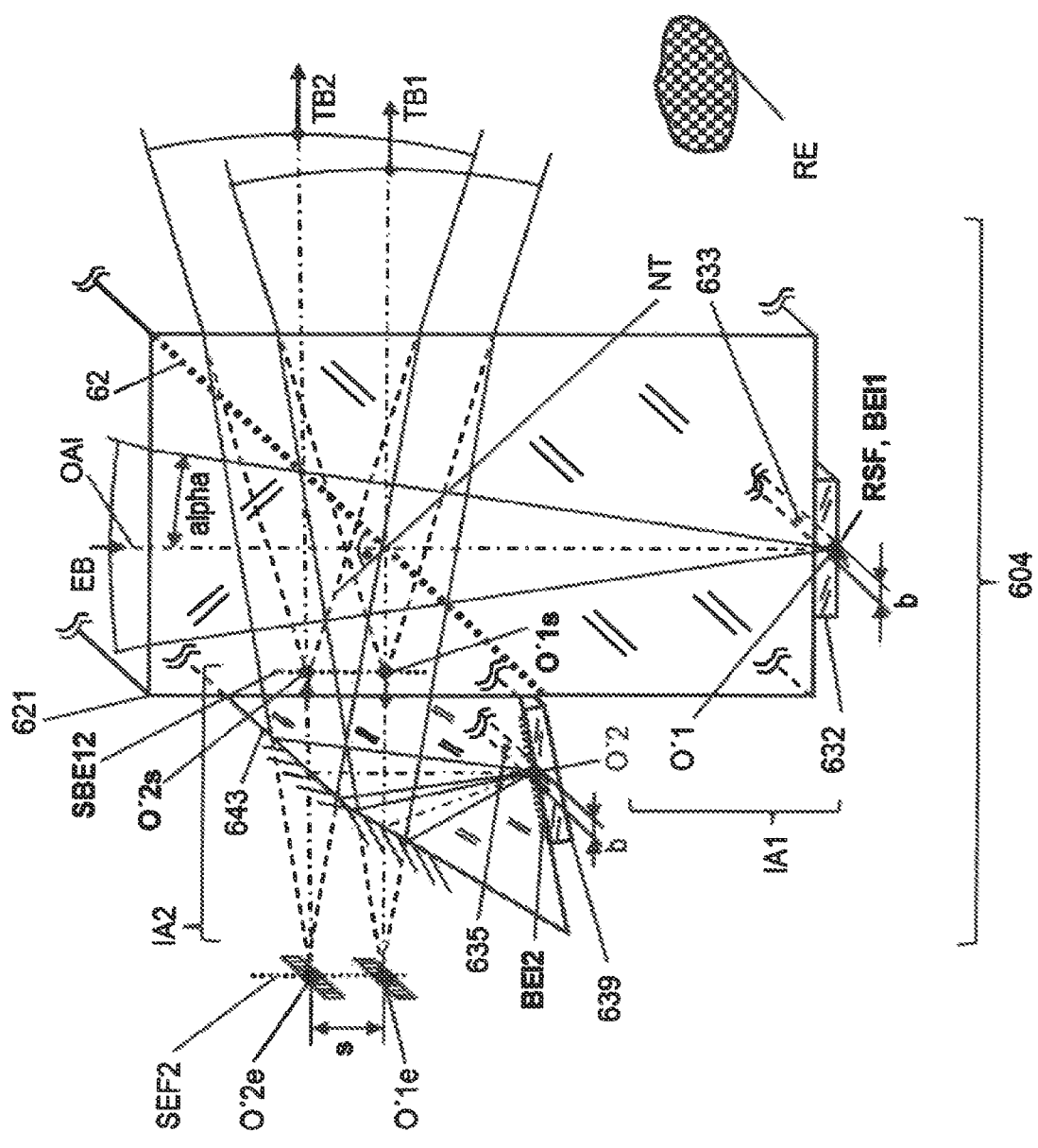
FIG. 6 is a schematic view of an exemplary Michelson-Type Interferometer.

FIG. 6 represents a further arrangement of a Michelson-Type Interferometer 604 with a triple periscope group 643, formed as a prism arrangement in throat shape, that is to say a triple plane mirror prism reflector. The linear mirrors 633 and 635 in this case act as field of view discriminators. Here too, the aperture angle alpha in the refractive material is comparatively large. The triple plane mirror prism reflector 643 can in particular also be used in a Michelson-Type Interferometer according to FIG. 4 or FIG. 5 in the visible and/or in the near infrared spectral range, provided suitable refractive materials are employed.

Figure 7:
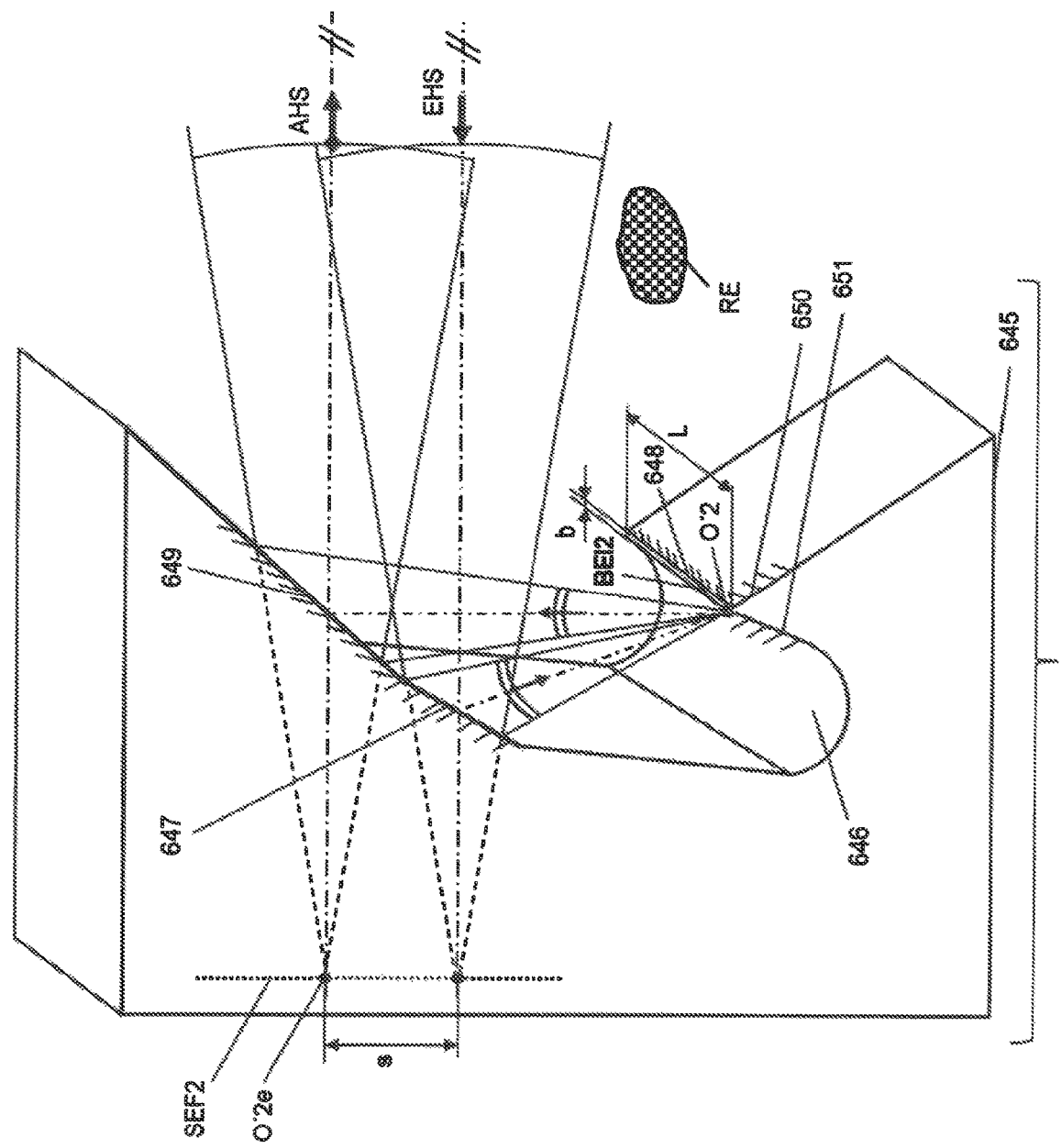
FIG. 7 is a schematic view of an exemplary triple periscope group.

FIG. 7 shows a triple periscope group 644 in a metal block 645, having a linear mirror 648 of width b, the mirror in this case having been formed very narrow, for example with a width of 0.1 mm and a length of 10 mm. An effective one-dimensional field of view discrimination can then be achieved.

Figure 8:
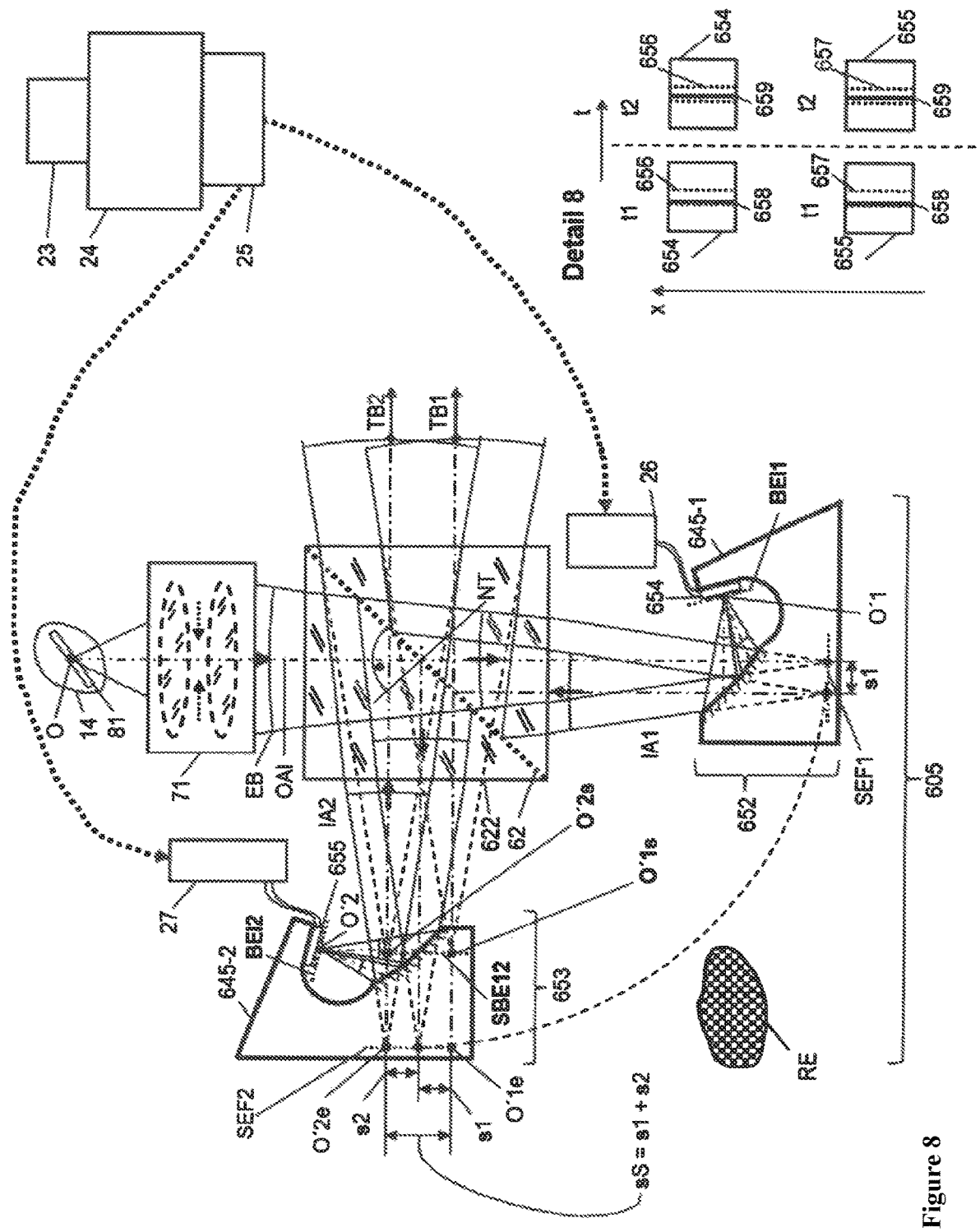
FIG. 8 is a schematic view of an exemplary Michelson-Type Interferometer.

In FIG. 8, the two triple periscope groups 652 and 653 in respectively one metal block 645-1 and 645-2 are arranged such that the resulting lateral shear sS is determined by adding the values of the lateral shear s1 and the lateral shear s2. The apparent image plane SBE12 with the apparent image points O'1s and O'2s is drawn in FIG. 8 as a clarifying illustration. Detail 8 intends to clarify that the two digital micro-mirror arrays 654 and 655 are operated in a synchronized manner. These represent the field of view discriminators BFD1 and BFD2. At a time t1, t2, [ . . . ], tn, respectively the same stripe-shaped image sections are then discriminated—or recorded—by means of the reflective, preprogrammed regions 658 and 659 by synchronizing the two digital micro-mirror arrays 654 and 655; as a result—given successive and synchronized shifting of the stripe-shaped image sections—a measured object can be completely scanned incrementally in a time series. This represents an internal scan of the two optically conjugated images of the measured object in the optically conjugated image planes BEI1 and BEI2. Using an arrangement according to FIG. 8, a relative movement between a measured object and the FT spectrometer can then be entirely omitted, while a hyperspectral full image can nevertheless be obtained with the internal scan. However, this implies comparatively low dynamics in the measured object in relation to the image rate of a raster detector (not shown here), which can be in the kilohertz range. It is then possible to obtain a hyperspectral video sequence of processes that run "at a snail's pace", such as slowly flowing, glowing magma as the measured object. Given suitable light conditions, a high-speed camera, for example with an image repetition rate of 10 kHz, can be used as a raster detector in this case.

Figure 9:
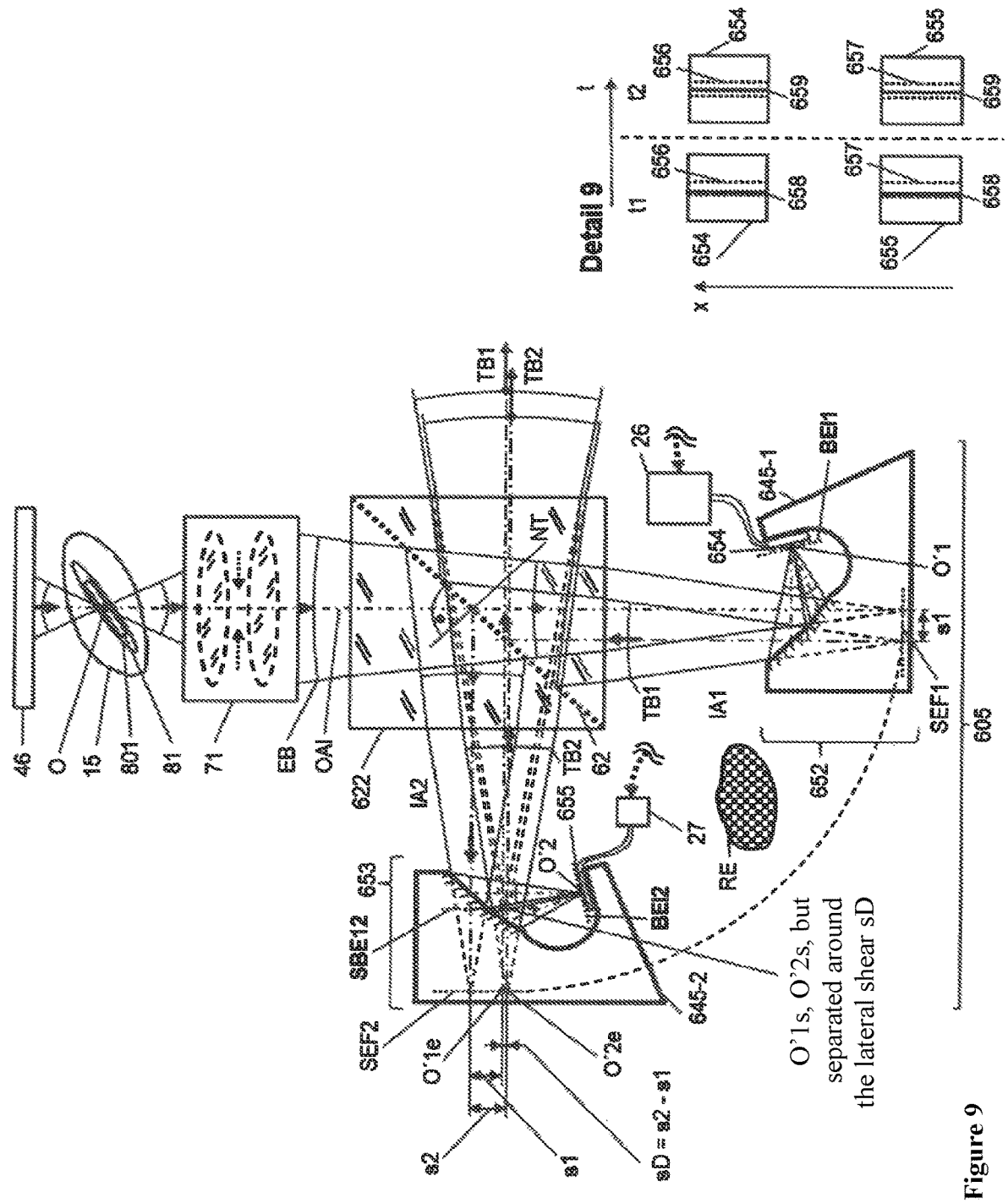
FIG. 9 is a schematic view of an exemplary Michelson-Type Interferometer.

In FIG. 9, the two triple periscope groups 652 and 653 are arranged in respectively one metal block 645-1 and 645-2 in a Michelson-Type Interferometer 605 such that the resulting lateral shear sD is partially compensated and is determined by the difference of the values of the lateral shear s1 and the lateral shear s2. The throat geometry is therefore formed somewhat smaller on the triple periscope group 652. So that the optical path difference nevertheless remains compensated, the triple periscope group 652 in the interferometer arm IA1 must for this purpose have a somewhat larger distance from the beam splitter cube 622 with the beam splitter layer 62, that is to say in the order of magnitude of several tenth of a millimeter. Strictly for illustration purposes, FIG. 9 shows the wave fronts at the output of the Michelson-Type Interferometer 605 somewhat shifted in the depth axis. The illustration of data lines was entirely omitted in FIG. 9 because these correspond to those in FIG. 8. The apparent image points O'1s and O'2s, which are also only slightly separated by the lateral shear sD, and also the unfolded image plane SBE12 are drawn in FIG. 9. The detail 9 corresponds to the detail 8 in FIG. 8 and is described there.

Figure 10:
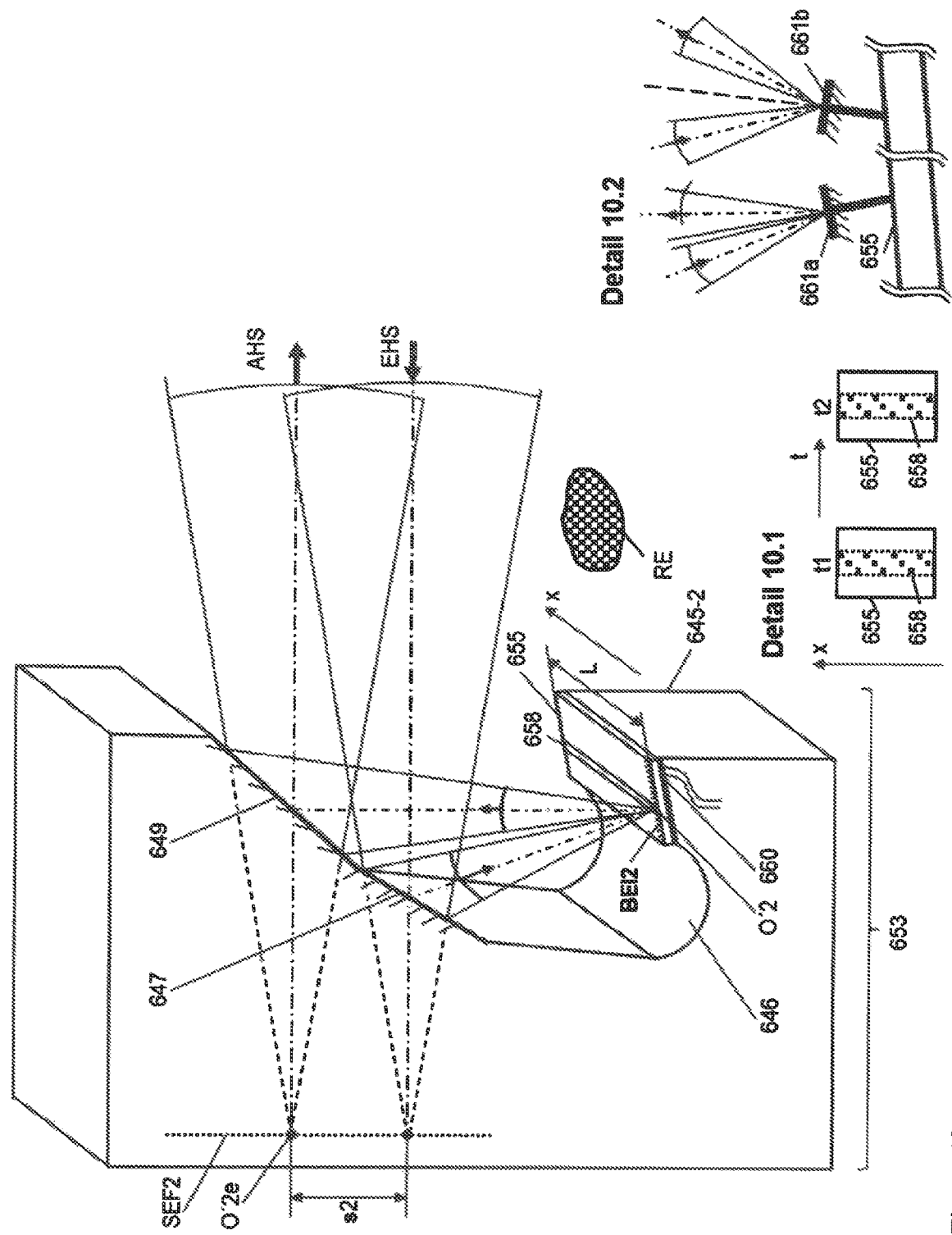
FIG. 10 is a schematic view of an exemplary triple periscope group.

FIG. 10 once again shows the second triple periscope group 653 in a modified metal block 645-2. A mirror surface is formed by a digital micro-mirror array 655. Various templates for field of view discrimination can then be preprogrammed in a digital micro-mirror array 655, which is symbolically illustrated in detail FIG. 10.1. The position of a micro-mirror 661a of the digital micro-mirror array 655 shown on the left in the detail FIG. 10.2 is used for reflecting the light that continues to be used and is therefore detected, that is to say selected. The position of a micro-minor 661b of the digital micro-minor array 655 shown on the right causes the light to be reflected away. The illustration of data lines was entirely omitted in FIG. 10 because these correspond to those in FIG. 8.

Figure 11:
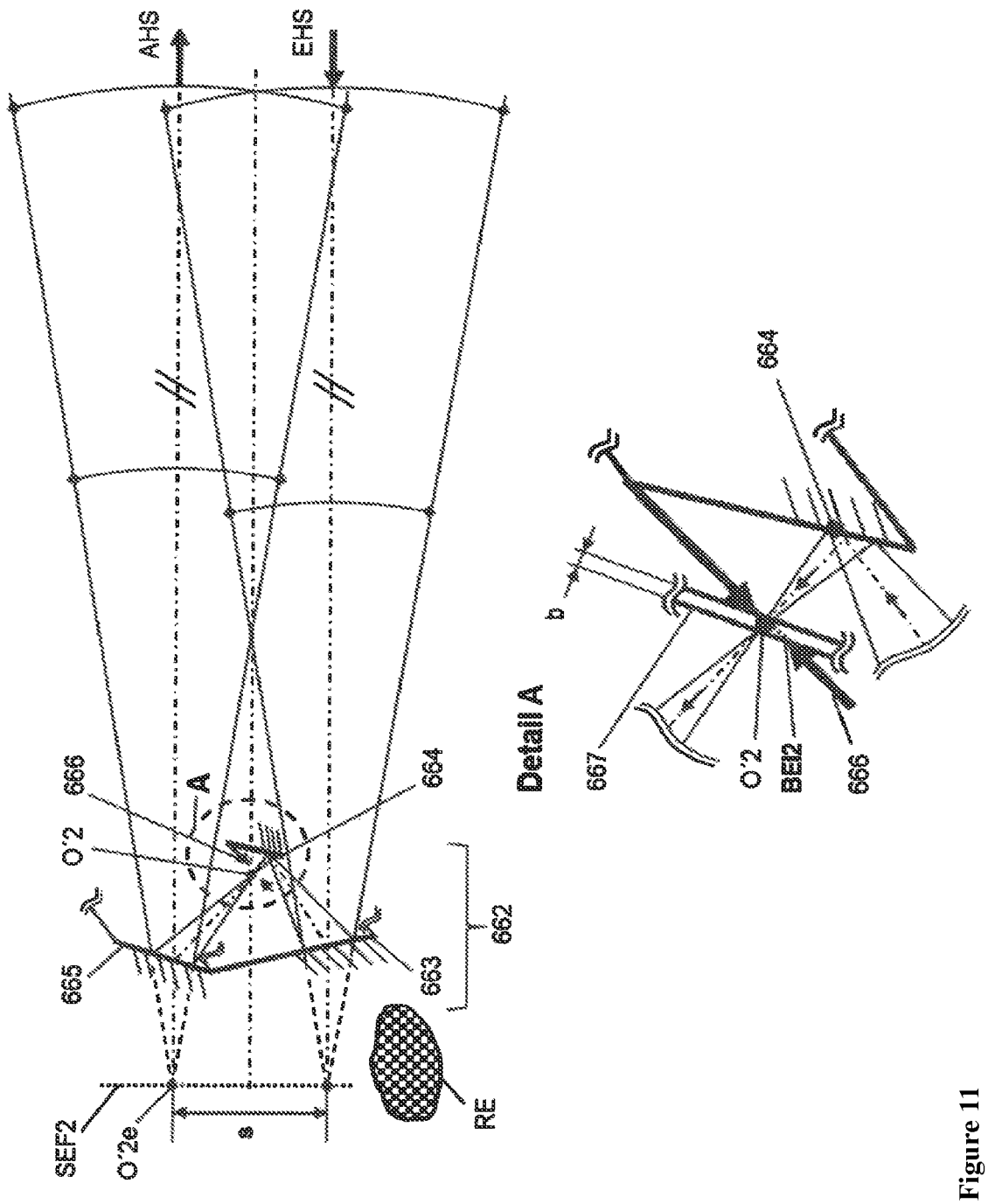
FIG. 11 is a schematic view of an exemplary asymmetric triple periscope group.

FIG. 11 shows an essentially asymmetric triple periscope group 662 with a gap aperture 666 having a gap 667. The image point O'2 in this case lies in the gap 667 in air and therefore at a location suited for field of view discrimination. A gap aperture 666 is highly effective for the field of view discrimination because the latter essentially fully blocks the light outside of the free gap.

Figure 12:
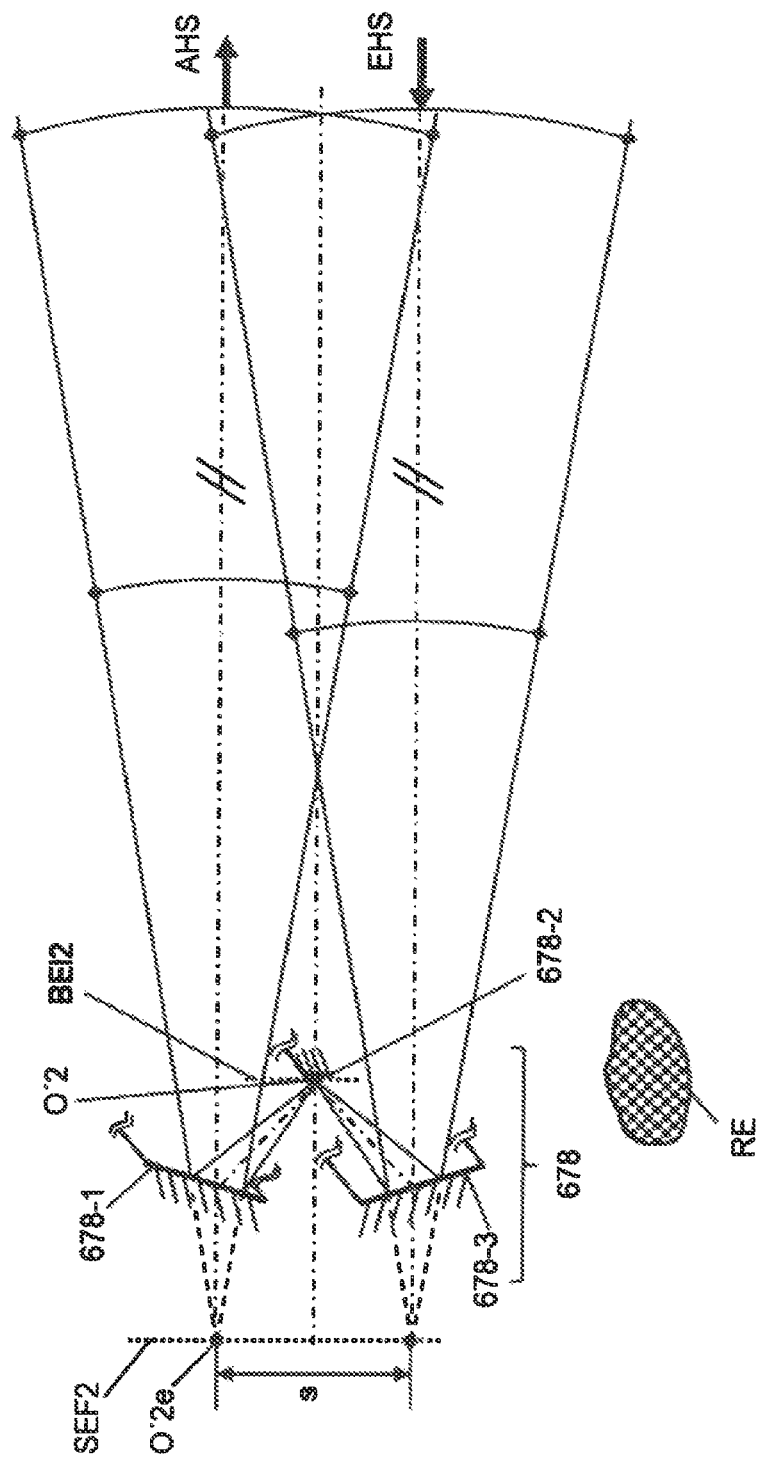
FIG. 12 is a schematic view of an exemplary symmetric triple periscope group.

FIG. 12 represents an essentially symmetrical triple periscope group 678 without gap aperture. This assembled symmetrical triple periscope group is formed as an arrangement in W shape in air and for the MIR range. The field of view discrimination in this case occurs using the second plane mirror of the triple periscope group 678-2, which is in this case formed narrow, and in the example shown here has a width of 0.2 mm. This triple periscope group 678 is inserted into a Michelson-Type Interferometer 608 in FIG. 17.

Figure 13:
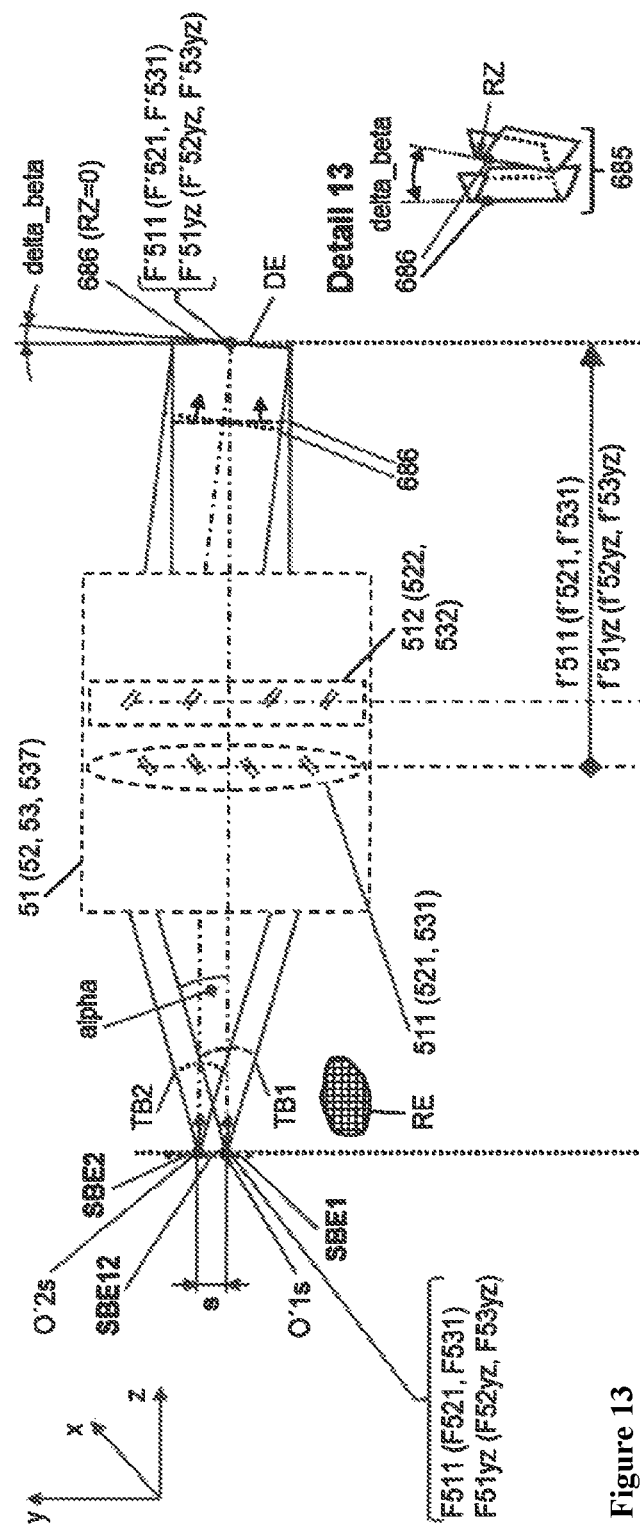
FIG. 13 is a schematic view of exemplary apparent image points with downstream anamorphic lens.
Figure 14:
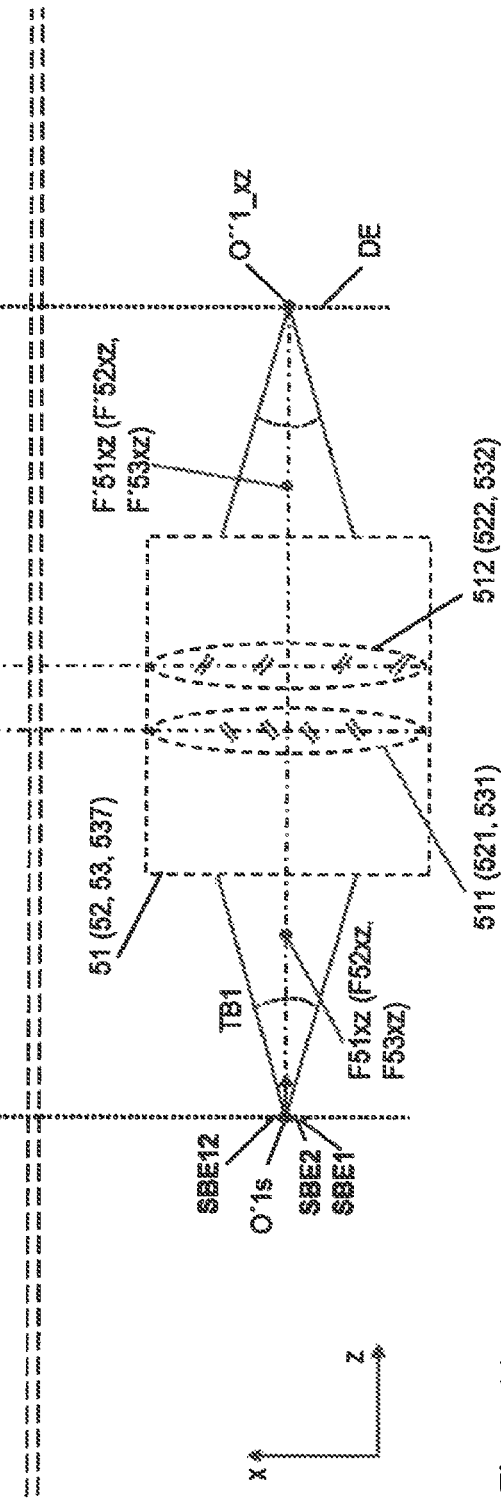
FIG. 14 is a schematic view of exemplary apparent image points with downstream anamorphic lens.

FIG. 13 and FIG. 14 show the imaging properties of an anamorphic and predominantly achromatic lens 51 arranged downstream of the Michelson-Type Interferometer and which used for detecting spatial interferograms rI. The function of this lens 51 is in this case explained in the metrology arrangement from FIG. 4.

The drawing plane in FIG. 13 is the yz plane, which also contains the apparent image points O'1s and O'2s, which are located in the apparent image plane SBE12, which essentially also includes the two apparent image planes SBE1 and SBE12. The apparent image plane SBE12 essentially also contains the focal point F511 of the anamorphic lens 51. By way of amplitude splitting, the apparent image points O'1s and O'2s represent essentially optically coherent image points in the interferometer, wherein said image points are separated from each other by the lateral shear s. A particularly good correction of the aberration must occur in the yz plane for the entire used spectral range of the Fourier spectrometer, that is to say originating from the object up to the raster detector, so that the spatial interferograms remain largely undisturbed. The imaging properties described herein are principally also exhibited by the anamorphic lenses 52 and 53, which are therefore stated in parentheses, as well as the downstream mirror lens 537, which is formed from the free-form surfaces 675, 676, and 677.

The drawing plane in FIG. 14 is the xz plane, which also contains the image point O"1_xz, which is formed in the detector plane DE using the lens 51. In the xz plane, the refractive power is at least approximately twice as large as in the yz plane. The raster detector, here the InGaAs camera 54, is positioned in the detection plane DE. The imaging properties shown here also apply for the further downstream anamorphic and largely achromatic lenses 52 and 53, which are therefore indicated in parenthesis, as well as for the downstream mirror lens 537.

Figure 15:
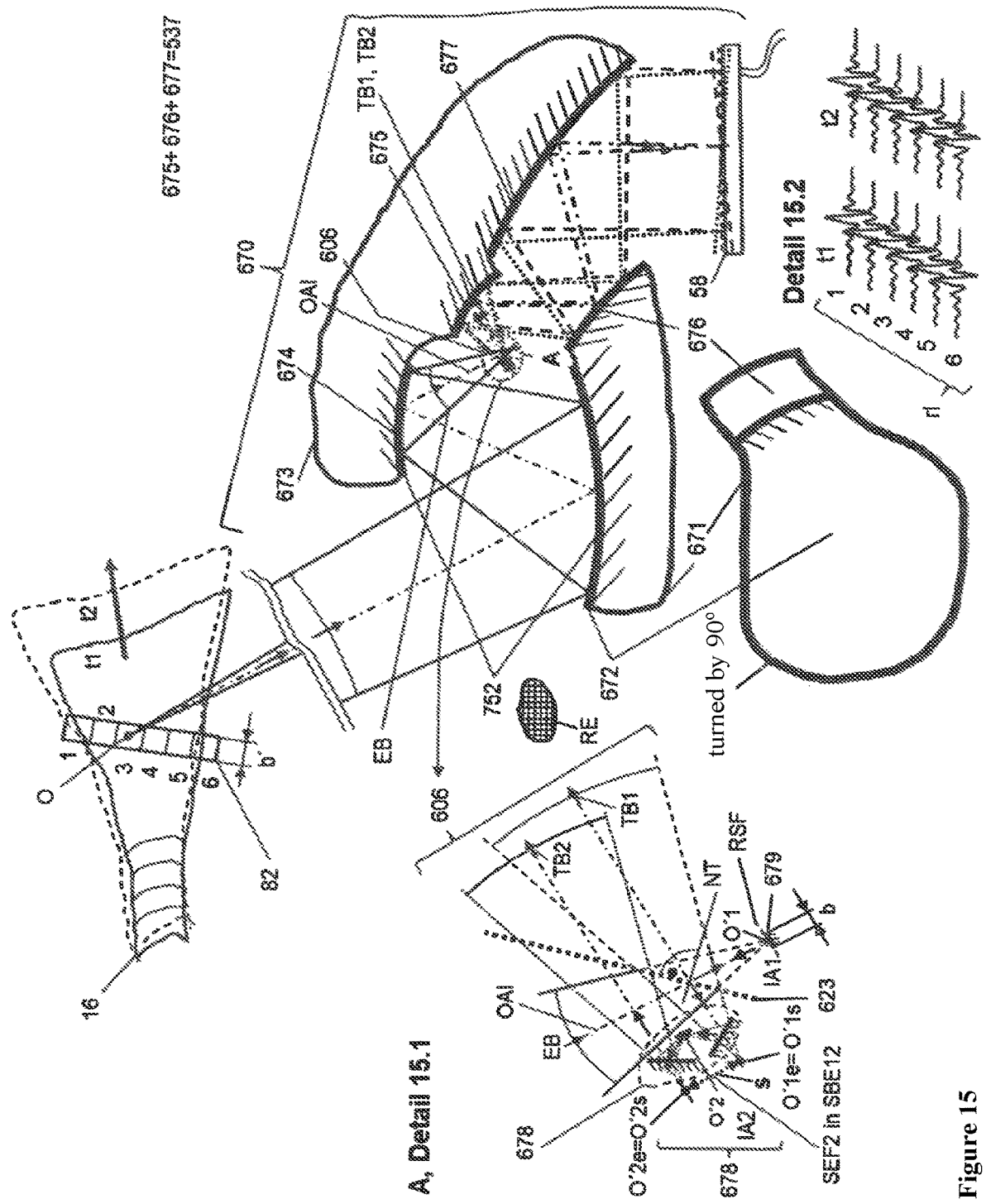
FIG. 15 is a schematic view of an exemplary use of an exemplary application on an exemplary FT spectrometer.

FIG. 15 shows a flowing hot exhaust cloud 16 above a factory facility at time t1, said cloud moving from left to right, and the cloud to be examined both spectrally in the far infrared spectral range and also spatially resolved. An arrangement 670 is inserted into the spectrometer system at ground level for the purpose of analyzing the hot exhaust cloud 16 at a larger distance. This arrangement 670 is formed with a Michelson-Type Interferometer 606 with the mirror blocks 671 and 673.

In this case, the image information about the exhaust cloud 16 plays a rather subordinated role for the measurement and analysis, because the object shape of the latter is of only minor interest for the analysis of air pollutants. Instead, the objective is to approximately determine the spectral composition based on the spatial resolution, which in particular permits conclusions about hazardous components. However, under no circumstances must significant spectral information that for example signifies toxic components be overlooked or not recorded, or allowed to slip through. It is initially not of uppermost interest where these toxic components are exactly localized in the exhaust cloud. It is already sufficient in many cases when the spectral information that signifies hazardous substances can at least be mapped to a single exhaust stack of a factory facility that generates the exhaust cloud, for example based on knowledge of the current wind direction.

The radiation emitted by the exhaust cloud 16, in particular in the far infrared spectral range, reaches the mirror block 671 with the reflective free-form surface 672 for purpose of focusing the arriving radiation. The mirror block 671 is shown at a reduced scale. Following reflection and further focusing using a second reflective free-form surface 674 on the mirror block 673, the radiation enters the Michelson-Type Interferometer 606. The apparent end mirror surface SEF2 in this case lies both in the apparent image plane SBE2 and also in the apparent image plane SBE12, to which the apparent image plane SBE1 is also mapped.

Following beam formation, the spatial interferograms are generated using the second reflective free-form surface 675 and using the reflective free-form surface 676, and using the third reflective free-form surface 677 on the bolometer array 58. The three reflective free-form surfaces 675, 676, and 677 form the anamorphic mirror lens 537.

In an exemplary embodiment 3 (without figure) on the basis of FIG. 15, two digital micro-mirror arrays are inserted in place of the two rigid mirrors in the arms of the Michelson-Type Interferometer; these track the movement of the exhaust cloud 16 synchronized by a computer-controller, and in this case respectively cause at least approximately the same object section to be detected. The metrology result can then be significantly improved by accepting certain unfocused regions in the spatial resolution of the exhaust cloud 16 by accumulating interferograms that increase the signal-to-noise ratio. The information for tracking and computer-controlling the digital micro-mirror arrays in real time is obtained by camera monitoring from the recorded movement of the exhaust cloud 16.

Figure 16:
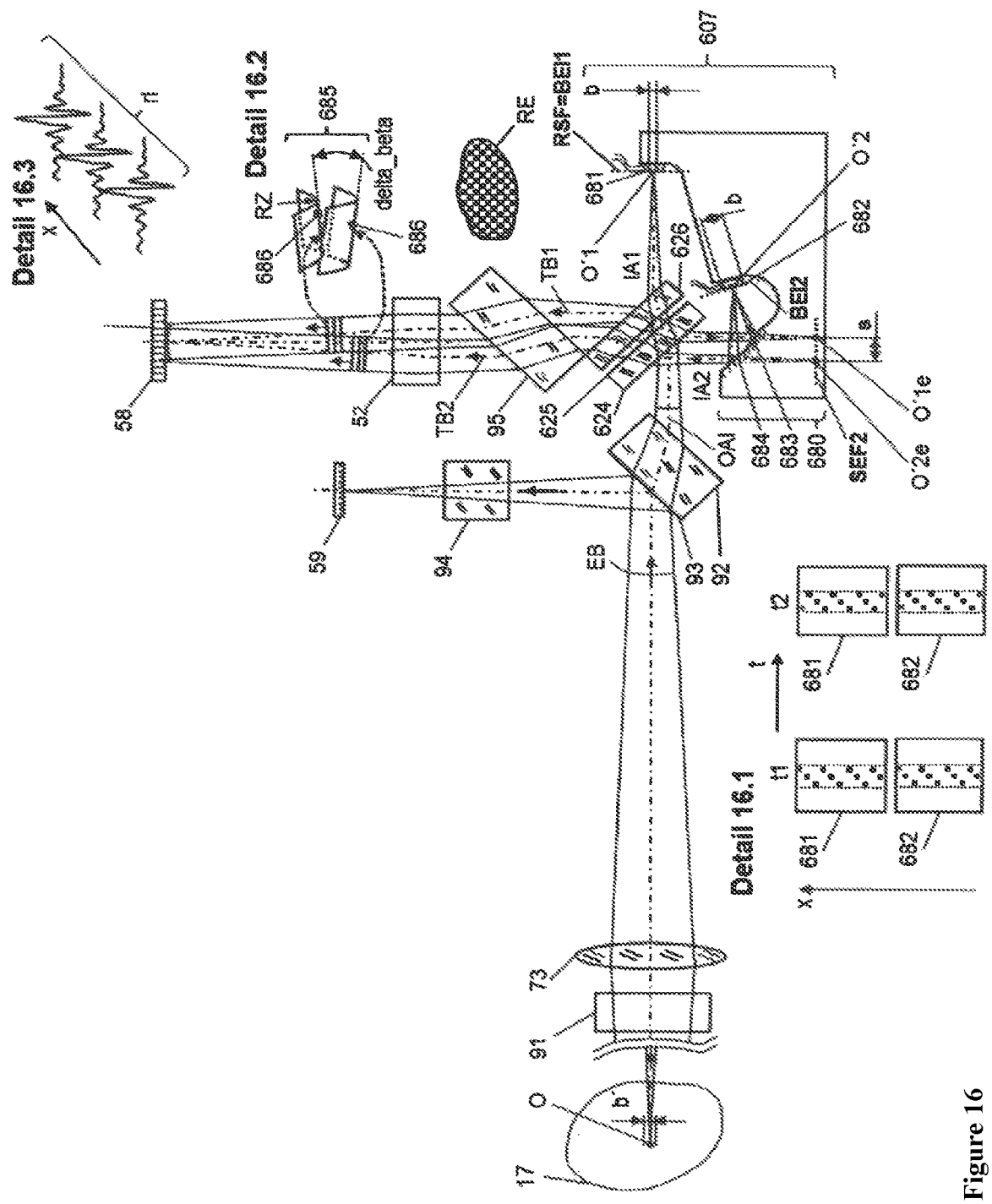
FIG. 16 is a schematic view of an exemplary FT spectrometer.

FIG. 16 shows an inaccessible organic measured object 17 at a medium distance that is emitting thermal radiation. The latter is scanned as a time series in narrow fields using a 2D mirror scanner 91. The light from the measured object 17 captured in the form of thermal radiation travels through an upstream lens 73 that partially renders the measured object 17 and is designed for the MIR spectral range, followed by a tilted CaF2 plate 92 for compensating astigmatism, and finally enters the Michelson-Type Interferometer 607 for the MIR spectral range. A beam splitter plate 624 with the beam splitter layer 625 and compensation plate 626 are arranged in this Michelson-Type Interferometer 607. Both plates can each comprise CaF2 and can in particular consist of CaF2. The active end reflectors for the MIR range are formed by a first digital micro-mirror array 681, in particular with gold-plating, and a second digital micro-minor array 682, in particular also with gold-plating. The plates 92 and 95, which can also preferably be fabricated from CaF2, are essentially only required for compensating astigmatism, which is generated by the greatly tilted beam splitter plate. The remaining opening error is corrected in the lens 73. The field of view is discriminated on the first digital micro-mirror array 681 in the Michelson-Type Interferometer 607. Since the triple minor arrangement does not feature an essentially vertical beam incidence onto the micro-mirror array 682, only a comparatively narrow field in lateral direction is possible, and the field of view may not be entirely perfectly discriminated on the digital micro-minor array 682, at least in the edge regions. The detail FIG. 16.1 shows the active regions programmed into the digital micro-minor arrays 681 and 682. For each x region, there is only one active region—drawn in black here—from which light is subsequently detected using the bolometer matrix detector 58.

One pair of coherent cylindrical waves is generated at the output of the Michelson-Type Interferometer 607 from each active region using an anamorphic lens 52, which is also formed with a cylindrical component for the MIR spectral range using CaF2. These cylindrical waves originate from the image points O"1 and O"2 that are coherent in relation to each other and essentially separated from each other by the lateral shear s. Two selected image points O"1 and O"2 are shown here in the unfolded state of the optical arrangement in relation to the anamorphic lens 52. The detail FIG. 16.2 shows the cylindrical waves 685 that are tilted toward each other and that are caused to interfere on a bolometer matrix detector 58, wherein the curvature radius RZ of the cylindrical waves 685 is very small, for example in the order of magnitude of less than 20 micrometers. Different active regions are recorded by the two digital micro-minor arrays 681 and 682 at different times t1, t2, . . . , so that the narrow field is fully captured over time. After the latter is fully captured, a further narrow field, for example an adjacent one or one of particular interest, is recorded using the 2D mirror scanner 91. The detail FIG. 16.3 shows spatial interferograms rI that belong to individual active regions of a narrow field. It is once again stated for the record that the field of view is in this case discriminated in the Michelson-Type Interferometer. This approach allows the hyperspectral image of the measured object 17 to be obtained as a time series.

FIG. 16 also fully omits illustrating data lines. These data lines essentially correspond to those in FIG. 8.

Figure 17:
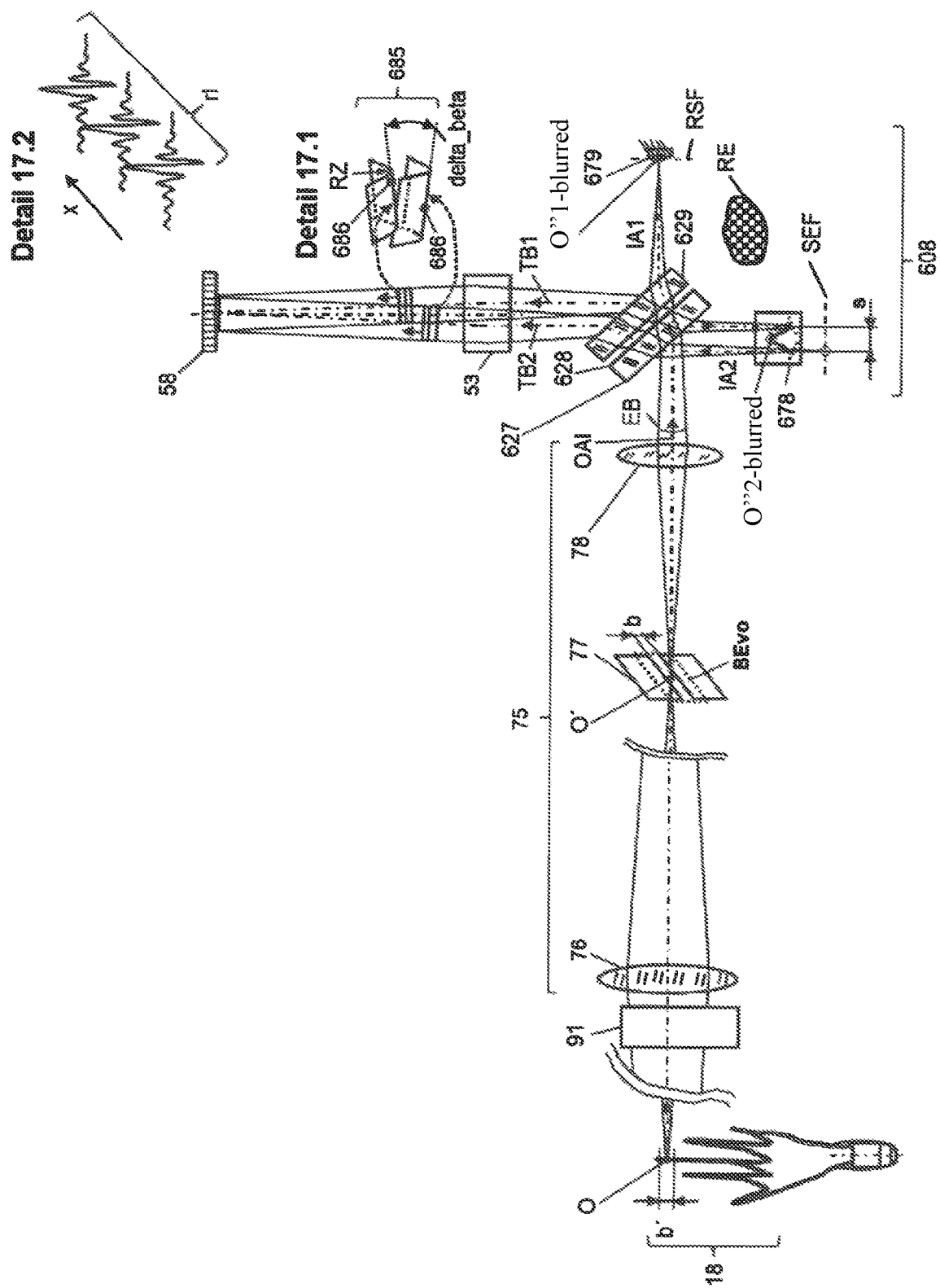
FIG. 17 is a schematic view of an exemplary FT spectrometer.

Whereas the previous figures showed the field of view discrimination generally occurring within the Michelson-Type Interferometer, the approach with a field of view discrimination upstream of the interferometer is shown starting with FIG. 17. Accordingly, no field of view discrimination occurs in the Michelson-Type Interferometer 608; instead, two images are generated that can also be rather unfocused due to aberrations. For this purpose, a two-stage upstream optics unit 75 in particular for the midinfrared spectral range (MIR) having a first lens 76, a gap aperture discriminator 77, and a second lens 78 is used. The gap aperture discriminator 77 is positioned in the image plane BEvo upstream of the Michelson-Type Interferometer 608. The measured object in FIG. 17 is in this case for example a jet engine flame 18 at a distance of several meters from the metrology system, operated in stationary mode. The hot exhaust gases of the latter also radiate in the MIR spectral range, and the objective is to record the hot exhaust gases in the MIR spectral range, both spectrally and also with their points of origin. The spectrums determined in the image can then be mapped to the respective spatial regions, and a hyperspectral image can be at least partially prepared.

A special advantage of this arrangement according to FIG. 17 is that the number of reflections in the respectively two arms of the Michelson-Type Interferometer 608, that is to say one reflection in the first interferometer arm IA1 and three reflections in the second interferometer arm IA2 reduces the astigmatism toward an opening error after leaving the Michelson-Type Interferometer 608. For this purpose, the Michelson-Type Interferometer 608 is constructed for the MIR with a beam splitter preferably consisting of a KBr beam splitter plate 627 and a KBR compensation plate 629, and a beam splitter layer 628. Passive end reflectors for the MIR range are additionally arranged in the Michelson-Type Interferometer 608. These end reflectors are preferably shown in the form of a narrow gold-plated plane mirror 679 in the first arm and in the form of an assembled triple periscope group 678 preferably with gold-plated plane mirror surfaces in the second arm of the Michelson-Type Interferometer 608. The latter is formed as a symmetrical arrangement in W shape and in air.

But this reduction of the aberration only occurs at the output of the Michelson-Type Interferometer 608 after twice passing the beam splitter functional assembly with the KBr substrates 627 and 629. As a result, a focused image is not generated in the Michelson-Type Interferometer 608, thus not readily permitting a field of view discrimination therein. Accordingly, a field of view discrimination is in this case not performed in the Michelson-Type Interferometer 608, but instead already prior to the beam entry into the interferometer, which however accordingly calls for an additional imaging stage 75 with a field of view discriminator. This field of view discriminator is in this case a gap aperture discriminator 77 arranged upstream of the Michelson-Type Interferometer 608 and that is positioned in the upstream image plane BEvo. The cylindrical waves 685 (shown in the detail FIG. 17.1) generated by means of an anamorphic mirror lens 53, in particular optimized for the NIR spectral range and also with a cylindrical mirror (not shown here), are subject to double beam interference on a bolometer matrix detector 58. One spatial interferogram rI exists for every x position, as symbolically illustrated in the detail FIG. 17.2. The opening errors existing in the Michelson-Type Interferometer 608 are corrected in the anamorphic mirror lens 53, so that largely undisturbed cylindrical waves are caused to interfere.

Figure 18:
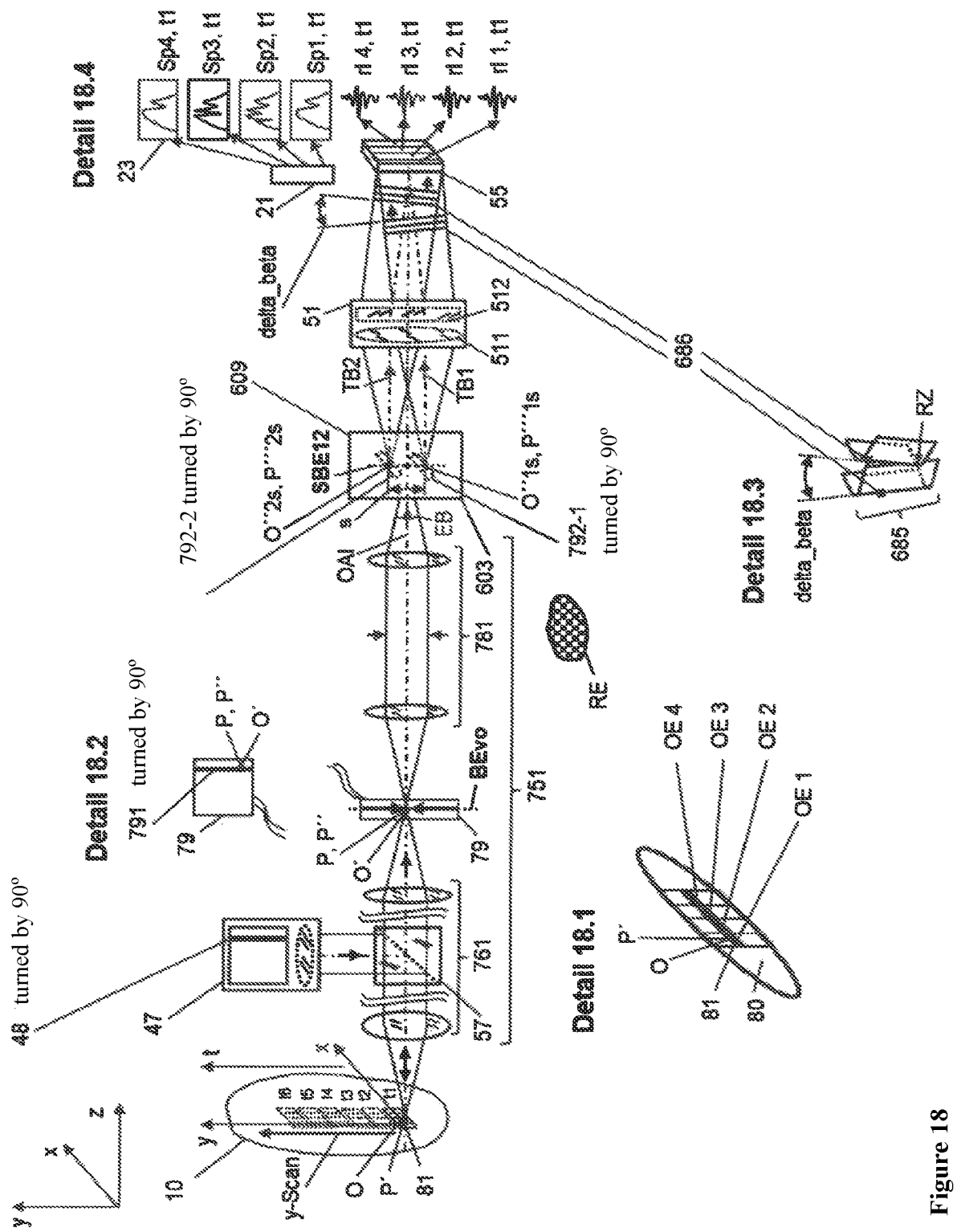
FIG. 18 is a schematic view of an exemplary FT spectrometer.

The field of view discrimination in FIG. 18 occurs in the visible spectral range, preferably using a liquid crystal display 79 (LCD) upstream of the Michelson-Type Interferometer 609 in a confocal arrangement 751 with the image plane BEvo arranged upstream of the Michelson-Type Interferometer 609. The Michelson-Type Interferometer 609 corresponds to the Michelson-Type Interferometer 603 already shown in FIG. 5, but is in this case formed without field of view discriminators in the interferometer. The exemplary embodiment described here for FIG. 18 therefore has no field of view discrimination in the interferometer.

The principle for the approach for a single shot line spectrometer with pronounced stripe-shaped illumination and spatial resolution in the stripe, that is to say using the pushbroom approach, is shown here with confocal discrimination of the object light. There is a one-dimensional y scan relative across the biological measured object 10 and laterally to the stripe. The scan is performed by moving the measured object 10 in y direction, which is secured on a y carriage not shown here.

A part of the measured object 10 is illuminated in the form of a stripe 80 with a controllable stripe light source 47 with an OLED array 48 and beamforming optics, after the light— here in the visible spectral range—has passed a coupling beam splitter cube 57 and a part of the first, assembled lens 761. The backscattered light passes the first, assembled lens 761 with the coupling beam splitter cube 57, and thus rendered—after passing a polarizer not shown here— reaches a liquid crystal display 79 (LCD) as a controllable gap aperture discriminator in the image plane of the lens 761, which is an upstream image plane BEvo in relation to the Michelson-Type Interferometer 603. Therein, there is a narrow pass-through area 791 (see detail FIG. 18.2) embedded—in the sense of programmed—into the liquid crystal display 79 that is fully covered by the field of the stripe 80, so that said pass-through area 791 in this case represents the field of view discriminator. The computer-controlled light source 47 and the liquid crystal display 79 are synchronized in relation to each other using the computer system 21. The data lines and control lines required for this purpose are not shown here. Using a computer controller, various regions can be illuminated in a synchronized manner on the measured object 10, for which there is then a matching pass-through area on the liquid crystal display 79. The liquid crystal display 79 with the respectively illuminated passthrough area 791 is recorded by a second assembled lens 781 and is then rendered into the Michelson-Type Interferometer 609 [sic: 603], which is comparable to the Michelson-Type Interferometer 603 shown in FIG. 5, but in this case is used without field of view discriminators. This system has a CMOS camera 55 as a raster detector for the visible spectral range. Here, a pair of cylindrical waves tilted toward each other is generated from each recorded object element OE (shown in the detail FIG. 18.1) whose peak lines 686 of the cylindrical wavefront 685 are tilted toward each other (see detail FIG. 18.3). These cylindrical waves generate spatial interferograms on a CMOS camera 55, shown here as examples r11 to r14 in lieu of a plurality of spatial interferograms in the detail FIG. 18.4, from which spectrums Sp are calculated, which are shown here as examples Sp1 to Sp4.

A liquid crystal display 79 as a controllable gap aperture discriminator in the upstream image plane BEvo essentially only allows a brightly luminescent stripe 80 on the measured object 10 to pass, the stripe 80 being generated by the controlled light source 47. This represents a confocal discrimination.

Figure 19:
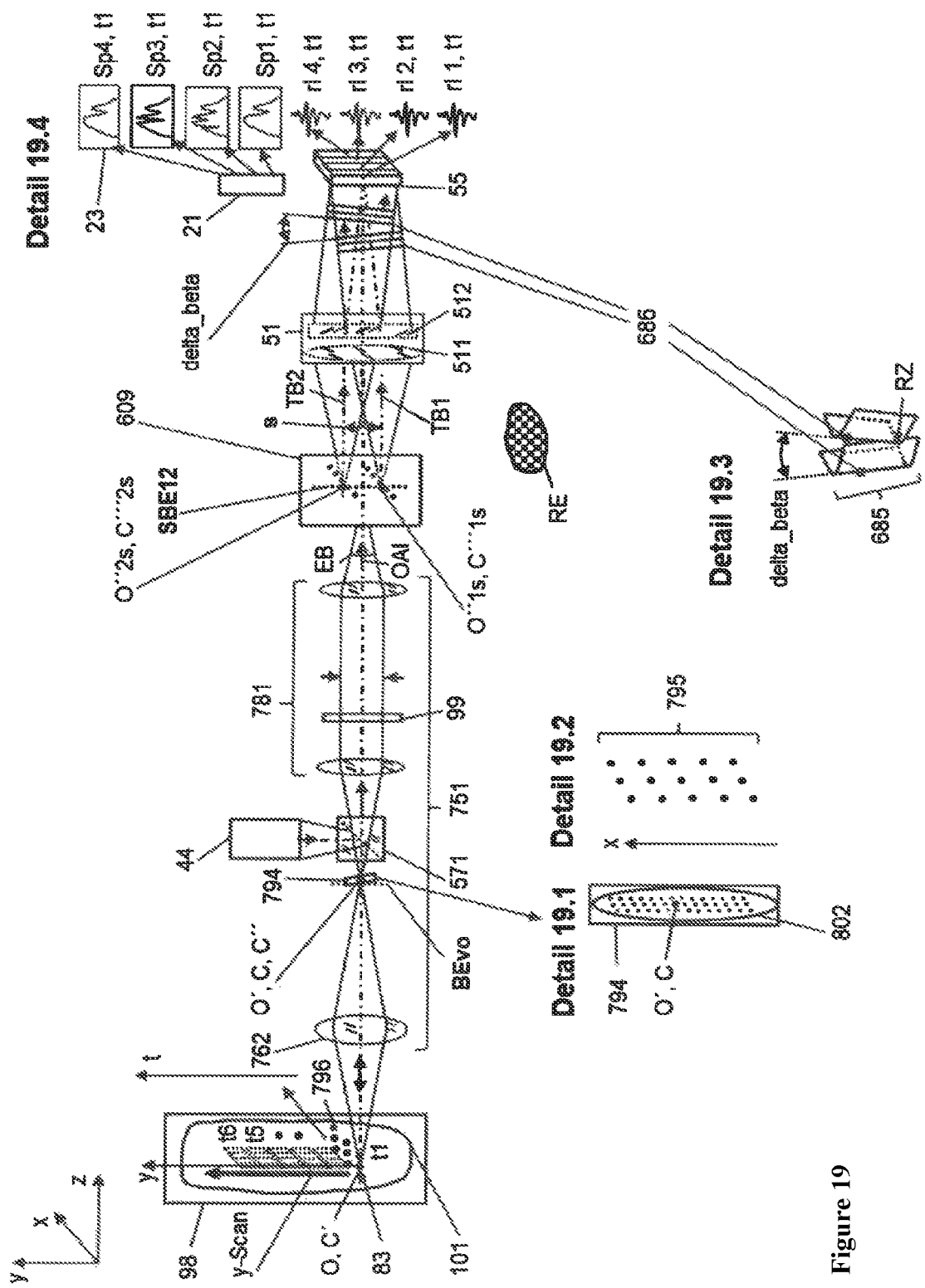
FIG. 19 is a schematic view of an exemplary FT spectrometer.

A confocal field of view discrimination shown in FIG. 19 is performed using a confocal arrangement 751 upstream of the Michelson-Type Interferometer 609. A pulsed UV light source 44 with integrated beam forming optics projects a stripe 802 of ultraviolet light onto a rigid aperture disk 794 with pinholes 802. The rigid aperture disk 794 is shown in the detail FIG. 19.1. This aperture disk 794 has a pinhole pattern 795 in a zigzag arrangement (see detail FIG. 19.2) of the pinholes, so that exactly only one pinhole is located in every x position.

Using the first lens 762 of the confocal arrangement 751, which is formed as a microscope lens, an image 796 of the illuminated pinhole pattern 795 is generated on the biological measured object 101 marked with fluorescent markers. Fluorescence occurs on the light points. Fluorescent light that originates from a focused image of a pinhole camera according to the confocal principle can upon returning pass the associated pinhole of the aperture disk 794, thus generating confocally selected light. After transmission of the light on the coupling beam splitter cube 571, the confocally selected florescent light enters the Michelson-Type Interferometer 603 using the second assembled lens 781 of the confocal arrangement 751 by passing the UV blocking filter 99; the Michelson-Type Interferometer 603 is shown in FIG. 5 and its operating principles are explained in the description for FIG. 5. However, in this case, the narrow mirrors 634 and 638 in the Michelson-Type Interferometer 603 (shown in FIG. 5) do not have a field of view restricting function. The exemplary embodiment described here for FIG. 19 therefore has no field of view discrimination in the Michelson-Type Interferometer 609. Using the anamorphic lens 51, respectively one cylindrical wave is created on a CMOS camera 55 for the visible spectral range for every image point O"1 and O"2 of an object point of the measured object 101 generated by beam splitting. The illustration here shows the apparent image points O"1s and O"2s in the apparent image plane SBE12. By way of double beam interference, respectively one pair of coherent cylindrical waves, whose peak lines 686 of the cylindrical wavefronts 685 are tilted toward each other (see detail FIG. 19.3) creates one spatial interferogram rI. The detail FIG. 19.4 only shows four spatial interferograms i11 to r14 that are mapped to four different pinholes as representative examples for a plurality of interferograms. By means of fast Fourier transformation (FFT) using a computer system 21 not shown here, the associated spectrums are calculated from said interferograms, shown here as examples for a plurality of spectrums as spectrums Sp1 to Sp4 (see detail FIG. 19.4). Due to the single shot approach for detecting spatial interferograms rI, and given matching integration times of the CMOS camera 55, the metrology setup is generally able to readily tolerate residual vibrations. Based on a precision y scan using a transport carriage 98, a stripe 802 respectively generated in a single shot, that is to say within the pulse time of the pulsed UV light source 44, can be used together with the associated spectrums Sp to incrementally generate an image section with hyperspectral information of the biological measured object 101. The pulsed UV light source 44 and the CMOS camera 55 are in this case synchronized.

Figure 20:
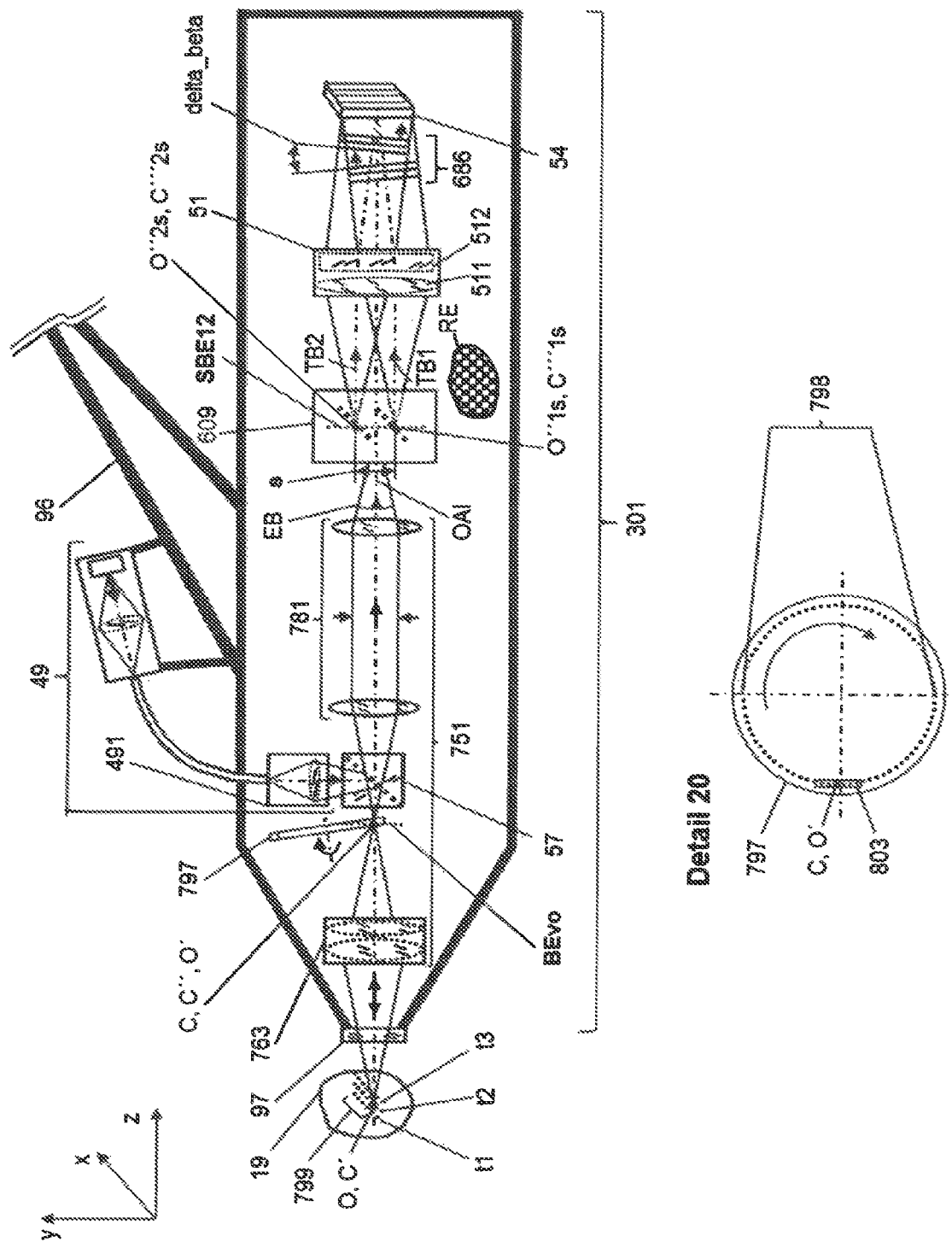
FIG. 20 is a schematic view of an exemplary FT spectrometer.

FIG. 20 shows a miniaturized mobile measurement head 301 with a confocal arrangement 751 on a robot arm 96 as a hyperspectral diagnostics instrument. This diagnostics instrument is used in an operating room. The robot arm 96 is arranged on a 5-axis robot not shown here, which in addition to translations in x and y direction also permits a comparatively precise computer-controlled depth axis movement in the z direction. Light is in this case fed into the mobile measurement head 301 using an external, fiber-coupled, near-infrared cold light source 49 with beamforming optics 491. After passing a coupling beam splitter cube 57, the light from the latter reaches a rotating aperture disk 797 with pinholes 798 that are arranged in a narrow circular ring. The detail FIG. 20 shows this aperture disk 797. Using the beamforming optics 491, a light stripe 803 is projected via the coupling beam splitter cube 57 onto several of the pinholes 798 located in a closed circular ring on the aperture disk 797. Using the first assembled, microscope lens stage 763, the illuminated pixels 798 are used for the confocal arrangement to illuminate the tissue 19. The images 799 of the luminescent pinholes 798 are generated there. The tissue 19 is part of a region for a surgical region on the open body of a patient under the conditions of a surgical procedure. The confocal principle states that essentially only light scattered by the surgical region 19 can pass the pinholes 798 of the aperture disk on the return path, which formed a focused focal point there in or on the tissue. The confocal field of view discrimination event occurs here using the pinholes 798 of the rotating aperture disk 797. The confocally selected light enters the Michelson-Type Interferometer 609 via the second imaging stage 781 of the confocal arrangement 751. Here, in FIG. 20, the narrow mirrors 634 and 638 of the Michelson-Type Interferometer 603 (shown in FIG. 5) however do not have a function that limits the field of view, because these mirrors in 609 are formed wider than the image resulting on the latter. The exemplary embodiment for FIG. 20 therefore has no field of view discrimination in the Michelson-Type Interferometer 609. Using the anamorphic lens 51, for every image point of the measured object respectively one cylindrical wave is generated on a detector, in particular on an InGaAs camera 54 for the near infrared spectral range, wherein only the apparent image points O"1s and O"2s are shown here symbolically. One pair each of coherent cylindrical waves forms a spatial interferogram by means of double beam interference. Due to the single shot approach for detecting interferograms, and given matching integration times of the InGaAs camera 54, residual vibrations of the 5-axis robot can generally be readily tolerated. A precision lateral movement can be used to incrementally prepare from an image stripe 803 respectively recorded in a single shot, that is to say within an integration time of the InGaAs camera 54, an image section with hyperspectral information of the tissue 19, which can then undergo a medical analysis. Using robotics, various positions along the depth axis can also be approached at various times t1, t2, t3, . . . to also examine the tissue 19 in the depth axis in a confocally discriminated manner, for the purpose of obtaining spectrums at various points along the depth axis. For reasons of clarity, FIG. 20 completely omits the illustration of the required driver, control, and data lines, and the computer system with its components.

The following is a detailed discussion, description, and/or definition of the employed terminology.

In this document, the term "light" is used as a synonym for electromagnetic radiation, that is to say in particular for the UV range up to the terahertz range.

This relates to a Fourier transformation spectrometer with a rather low to moderate spectral resolution, preferably in the range of delta_sigma equal to 4 $cm^{-1}$ up to 1000 $cm^{-1}$.

The term lateral shear is based on the phenomenon of interference between two reflecting light beams with lateral shift, that is to say transversal shift. In conventional arrangements, this typically involves reflecting a light beam under test on an outer surface and a light beam on an inner surface of a shear plate such that they are reflected spatially (and chronologically) shifted in relation to each other. A lateral shear can in particular be typically generated with a shear interferometer, wherein the shear interferometer is an optically comparatively simple device in the form of a plate for the purpose of conducting a wavefront analysis. It can be used to test the collimation of light beams, in particular of laser sources, whose coherence length is generally significantly greater than the optical thickness of the plate. The shear interferometer, which is formed as a plate, typically comprises an essentially high-value optical glass, such as N-BK7 or also quartz glass with particularly planar and smooth optical surfaces, that are normally arranged at a very small angle in relation to each other, and are therefore arranged essentially not parallel in relation to each other, and therefore have a very weak wedge-shaped character. During the test, a properly collimated beam, is incident on the shear interferometer in the form of a plate at an angle of approximately 45°, and is reflected twice. Due to the weak wedge-shaped character, the two reflected light beams are slightly tilted toward each other after passing the plate, and given perfect collimation of the input beam (planar wavefront), exhibit interference stripes downstream of the shear plate that are typically oriented in parallel to the direction of the lateral shear given perfect collimation, but that are rotated in relation to this direction of the lateral shear given imperfect collimation. This separation or lateral shift of the beams generated by the shear plate is referred to as shear, in particular as lateral shear. The lateral shear can also be generated by lattices or, as in the present case, by a suitable mirror group, in particular by a triple mirror periscope reflector according to the invention. Lateral shear is indicated in the respective drawings with the referenced symbol "s".

The term "Double-Beam Interferometer" in particular comprises a Michelson-Type Interferometer.

The acronym FIR in particular refers to the far infrared spectral range, wherein the latter in particular lies approximately between 50 μm and 1000 μm.

On a Michelson-Type Interferometer, the outbound and the return beam in particular at least approximately propagate in parallel to each other in each interferometer arm, and the beam splitting and beam unification essentially occur on the same beam splitter surface. The term "Michelson-Type Interferometer" is herein predominantly used in lieu of "Michelson Interferometer" because the arrangements described herein in particular have more than one plane mirror in at least one the interferometer arms IA1 and IA2, thus not referring to a pure "Michelson Interferometer" in the strict sense.

The acronym MIR in particular refers to the midinfrared range, which in particular lies between approximately 3 μm and 50 μm.

A field of view discriminator is in particular an opening in an aperture, wherein the opening preferably is a gap aperture 645, a pinhole, a pinhole array that comprises a plurality of pinholes, and/or a pass-through area 656, 657 of a liquid crystal display 655.

A nondiscriminating area of a field of view discriminator for example comprises the pass-through area on a gap-shaped field of view discriminator, that is to say in the simplest case the gap opening and/or the reflecting area, for example in a very narrow plane mirror as a field of view discriminator. The nondiscriminating area can also be represented by a spatial light modulator in transmission (liquid crystal display) and/or in reflection (digital micro-mirror array). The nondiscriminating area can also exhibit a fine structuring.

A field of view discriminator can in particular also have a narrow reflective area on a plane mirror and/or on a micro-mirror array, and/or also a narrow plane mirror.

The specified forms of a field of view discriminator are in particular designed to allow at least a part of a light beam to pass and cause the detection of the latter on a well-defined beam path into the further section of the beam path, most preferably in the form of a narrow stripe that preferably can correspond to a tenth up to a thousandths of the extent of the image, for example one tenth up to one thousandths of the height of the image of the measured object in the double beam interferometer. The de facto "one-dimensionality" of the narrow stripe—with image elements preferably in only a single line—ultimately permits generating respectively exactly one spatial interferogram from each of the image elements still remaining after selection. In other words, in particular those parts of a light beam are hidden or blocked by the field of view discriminators that are not intended to follow the predetermined beam path. The field of view discriminator can for example also be used to hide or block scattered light. This means that scattered light is likewise prevented from passing the field of view discriminator in the further section of the beam path. The term "spatial selection" refers to the selection or to the passing of the light that can pass or fall through the field of view discriminator, for example the gap, and is ultimately detected. In other words, not only the field of view is selected, but the stray light undesired in this case is minimized.

A prism, alternatively also called mirror prism, in particular has a refractive material, such as $CaF_2$, Si, BK7, quartz, and/or other commonly used optical materials. The prism can be at least partially coated, non-reflective, or can also be completely uncoated. The prism in particular has at least one entrance and/or exit surface suited for the entrance and/or exit of a light beam. The prism in particular also has at least one reflection surface or a mirror surface that under suitable conditions is designed to reflect or mirror at least a part of the light beam entering the prism. An essentially complete reflection can also occur in particular at angles of total reflection. The prism can in particular also have a second reflection surface or a mirror surface that under suitable conditions is designed to reflect or mirror at least a part of the light beam entering the prism a second time.

The prism can have a mirror surface on at least a section of a reflection surface. The surface area of a reflection surface can for example be at least partially coated with gold and/or silver and/or aluminum.

The terms reflection surface and mirror surface generally correspond to each other. A mirroring or a reflection can occur on an at least partially mirrored surface or in particular also under certain angles on a transition between media of different refractive indexes, for example when a light beam that passes through an optically dense medium is incident on a boundary surface to a medium of low optical density. A total reflection can occur under special angles, wherein essentially the entire part of the light beam is reflected in full.

A mirror prism that uses two reflection surfaces can in particular be a prism on which the two reflection surfaces describe a right angle and wherein the entrance and exit surface of the prism is positioned opposite said angle.

A beam splitter of a beam splitter unit in particular corresponds to a beam splitter cube or two individual plane parallel plates, that are preferably respectively formed from quartz glass, crystalline quartz, calcium fluoride (CaF2), zinc selenium (ZnS), or potassium bromide (KBr), and have a beam splitter layer or a polarizing beam splitter cube or a plate beam splitter with two plates and a beam splitter layer. A beam splitter is in particular designed to transmit at least a part of the incident light beam on an exit surface in order to generate the first partial beam and to reflect at least a further portion of the incident light beam in order to generate the second partial beam. A beam splitter is furthermore in particular designed to reflect at least a part of the first partial beam on the beam splitter surface and to transmit at least a part of the second partial beam.

A beam splitter unit has at least one planar beam splitter layer in particular in a beam splitter cube or in a system comprised of plane parallel plates. The beam splitter layer has a first side facing the incident light beam and a side facing away from the incident light beam. The beam splitter surface is designed to transmit incident light in parts in order to generate and partially reflect a first partial beam in order to generate a second partial beam. Two partial beams that project essentially vertically in relation to each other are then in particular generated in a conventional Michelson-Type Interferometer.

A reference plane that for example can be used to describe the arrangement of a (2n+1) mirror group is in particular spanned by the normal of the planar beam splitter surface and by the optical axis of the upstream lens at the input of the Michelson-Type Interferometer.

A (2n+1) mirror group can have mirror surfaces isolated from each other that can without directly contacting each other be arranged vertically in relation to a common reference plane.

Alternatively or additionally, a (2n+1) mirror group can also have at least two mirror surfaces that contact each other or are even formed together in a single unit. In this case, the mirror surfaces then correspond to mirror surface sections that are arranged in different planes vertically in relation to a common reference plane. In other words, two mirror surface sections in this case form a mirror with a bend.

The term "(2n+1) periscope group" corresponds to the term "(2n+1)-fold periscope group". Other than on a triple mirror arrangement, the plane mirror surfaces on a triple periscope group are at all times positioned vertically in relation to a common reference plane.

Cylindrical waves are in particular light waves that represent a section from a cylindrical surface.

In a Michelson-Type Interferometer, the first field of view discriminator unit and the second field of view discriminator unit lie in optically conjugated planes when the angles in the Michelson-Type Interferometer are adjusted with sufficient accuracy, and the optical distances in the two interferometer arms are equivalent. In this case, the same optical materials must be used in the two interferometer arms.

A focused image is in particular characterized in that it is nearly diffraction-limited.

An unfocused image is in particular characterized in that its image spots exceed the size of an Airy disk several times.

An astigmatism in particular comprises the phenomenon that in two intersection planes arranged vertically in relation to each other, two image points that are respectively formed by the beams of the respective intersection plane are significantly separated in their position along the depth axis, that is to say significantly separated in the propagation direction of the light. In relation to the invention, during detection, one of the image points is essentially preferably located in infinity, and the other image point preferably lies in the near range, preferably on the raster detector.

The term "depth axis" refers to the dimension in the propagation direction of the light.

The term "wave-optical depth of field focal range" is defined by the relation of the light wavelength divided by the square of the sine of the aperture angle of the associated light beam.

A mirrored surface is in particular designed to reflect approximately 80% to about 100%, in particular at least approximately 93% to about 100%, and preferably approximately 97% to approximately 100% of the incident light in at least a part of the wavelength spectrum of electromagnetic radiation.

An unreflective or non-reflective surface is in particular designed to reflect less than approximately 60%, in particular less than approximately 30%, and preferably less than approximately 5% of the incident light in at least a part of the wavelength spectrum of electromagnetic radiation.

An optical interference can be created during measurements of biological tissue by stray light that is distributed to several detector elements on a raster detector. This stray light is largely blocked by a confocal discrimination that reduces the optical interference. An optical interference can also be understood to mean that rays from an imperfect and/or slightly unfocused light beam that generate an image point for example on a detector element of a raster detector also reach one or several adjacent detector elements of the raster detector.

The following describes special embodiments and examples that can be combined with each other and in particular with the aspects of the invention, provided they do not exclude each other:

Fourier transformation spectrometer with at least partial hyperspectral imaging of a measured object as a product of a calculation using a computer system for calculating spectrums by means of Fourier transformation and the Fourier transformation spectrometer is formed with a lens arranged upstream of the Michelson-Type Interferometer that is used as imaging system for the measured object, with the optical axis OAT to generate at least one focused input beam for the Michelson-Type Interferometer, and the Michelson-Type Interferometer comprises:

a beam splitter with a planar beam splitter surface and wherein the beam splitter is used for both beam splitting, thus forming two partial beams, and also for at least partial beam unification using a lateral shear s between the two partial beams and a reference plane exists on the Michelson-Type Interferometer wherein the reference plane is spanned by the normal of the planar beam splitter surface and by the optical axis of the upstream lens on the input of the Michelson-Type Interferometer,
and a raster detector
and the Michelson-Type Interferometer has at least one light source
and at least one spatial interferogram is formed on the raster detector,
wherein either an at least approximately planar end mirror 633, 679 or a planar end mirror surface 638 is arranged in the first interferometer arm IA1 of the Michelson-Type Interferometer 601, 602, 603, 604, 605, 606, 607, 608, 609 and a triple periscope group 641, 642, 643, 644, 652, 653, 662, 678 is arranged in the second interferometer arm IA2 as end reflector, and the triple periscope group 641, 642, 643, 644, 652, 653, 662, 678 consists of an arrangement of in total three at least approximately planar mirrors 647, 648, 649, 663, 664, 665, 678-1, 678-2, 678-3, 683, 684 or at least approximately planar mirror surfaces 634, 635 in throat or W shape, and respectively with angles in relation to each other that are generally aligned vertically in relation to the reference plane RE,
or
respectively one triple periscope group 641, 642, 643, 644, 652, 653, 662, 678 is arranged as end reflector in each of the two interferometer arms IA1, IA2 of the Michelson-Type Interferometer 601, 602, 603, 604, 605, 606, 607, 608, 609
or
a (2n+1)-fold periscope group 640 with n=2, 3, 4 is arranged as end reflector in at least one of the two interferometer arms IA1, IA2 of the Michelson-Type Interferometer 601, 602, 603, 604, 605, 606, 607, 608, 609, the periscope group consisting of an arrangement of—in total (2n+1)—planar mirrors or planar mirror surfaces, in throat or W shape or in a mixed form, and respectively aligned in relation to each other at angles that are generally vertical in relation to a common reference plane RE,
and in all cases the total number of mirrors or mirror surfaces in the Michelson-Type Interferometer 601, 602, 603, 604, 605, 606, 607, 608, 609 is at least four, and—even given a total number greater than four—is generally an even number
and in all cases, the rays of a partial beam TB1, TB2 are respectively only reflected once on every mirror 648, 664 or on every mirror surface in the Michelson-Type Interferometer 601, 602, 603, 604, 605, 606, 607, 608, 609 upon passing an interferometer arm IA1, IA2.

Fourier transformation spectrometer,
wherein the beam splitter is formed as an amplitude beam splitter, as shown by a planar beam splitter layer 62, 625, 628 or a mylar foil 623 or a lattice.

Fourier transformation spectrometer,
wherein at least one field of view discriminator BFD1, BFD2, 633, 643, 635, 638, 654, 655, 77, 79, 794, 797 is mapped to the Michelson-Type Interferometer 601, 602, 603, 604, 605, 606, 607, 608, 609.

Fourier transformation spectrometer,
wherein at least one field of view discriminator BFD1, BFD2, 633, 643, 635, 638, 654, 655 is arranged in the Michelson-Type Interferometer 601, 602, 603, 604, 605, 606, 607, 608.

Fourier transformation spectrometer,
wherein at least one field of view discriminator BFD, 633, 643, 635, 638, 654, 655 is arranged downstream of the beam splitter 62, 623, 625, 628 of the Michelson-Type Interferometer 601, 602, 603, 604, 605, 606, 607, 608.

Fourier transformation spectrometer,
wherein a field of view discriminator BFD, 633, 638, 654, 655, 679 is arranged in an interferometer arm in a real mirror surface RSF.

Fourier transformation spectrometer,
wherein a field of view discriminator BFD1 is arranged in the first interferometer arm IA1 in a surface optically conjugated in relation to the apparent end mirror surface SEF2 of the second interferometer arm IA2.

Fourier transformation spectrometer,
wherein in a second field of view discriminator BFD2, 634, 635, 654 is arranged in the second interferometer arm IA2, wherein said second field of view discriminator is optically conjugated in relation to the field of view discriminator BFD1, 633, 638, 655 in the first interferometer arm IA1 and is at approximately formed geometrically equivalent to the first field of view discriminator BFD1, 633, 638, 654.

Fourier transformation spectrometer,
wherein at least one field of view discriminator (BFD, 77, 79, 794, 797) is arranged directly upstream of the Michelson-Type Interferometer (608, 609).

Fourier transformation spectrometer,
wherein at least one field of view discriminator BFD is mapped to the image of a measured object 10, 101, 11, 14, 15, 16, 17, 18, 19 in the beam path in the Michelson-Type Interferometer 601, 602, 603, 604, 605, 606, 607, that is formed using the upstream lens 70, 71, 73, 75, 752, 78, 781.

Fourier transformation spectrometer,
wherein a first field of view discriminator BFD1 is mapped to the end mirror 633, 638 and a second field of view discriminator BFD2 is mapped to the triple periscope group 641, 642, 643, 644, 652, 653, 662, 678.

Fourier transformation spectrometer,
wherein the field of view discriminator BFD is formed by the end mirror 633, 638 or by a mirror of the triple periscope group 641, 642, 643, 644, 652, 653, 662, 678.

Fourier transformation spectrometer,
wherein at least one field of view discriminator BFD is formed as a raster mirror or as a raster mirror surface.

Fourier transformation spectrometer,
wherein computer-controllable motion elements are mapped to the elements of the raster mirror or the raster mirror surface.

Fourier transformation spectrometer,
wherein these two field-of-view discriminators BFD1, BFD2 are arranged optically conjugated in relation to each other when placing respectively one field of view discriminator BFD1, BFD2 in each interferometer arm IA1, IA2 of the Michelson-Type Interferometer 601, 602, 603, 604, 605, 606, 607.

Fourier transformation spectrometer,
wherein at least one field of view discriminator BFD is formed as a gap-shaped shading aperture 666, 77.

Fourier transformation spectrometer,
wherein at least one field of view discriminator BFD is formed as a micro-gap shading aperture array.

Fourier transformation spectrometer,
wherein at least one field of view discriminator BFD is formed as a pinhole shading aperture.

Fourier transformation spectrometer,
wherein at least one field of view discriminator BFD is formed as a one-dimensional or two-dimensional pinhole shading aperture array in the form of an aperture disk 794, 797.

Fourier transformation spectrometer,
a micro-gap shading aperture array is formed with micro gaps in a laterally shifted arrangement.

Fourier transformation spectrometer, wherein the micro-gap shading aperture array is formed with mechanically moving elements.

Fourier transformation spectrometer,
wherein a fine structured field of view discriminator in gap shape or in dotted line shape is mapped to the measured object 10, 14, 15 or to the field of a light source 43, 44, 46, 47 and the lengthwise direction of the field of view discriminator is aligned vertically in relation to the reference plane RE.

Fourier transformation spectrometer,
wherein the light source 47 itself is formed of fine luminescent elements in a straight line or in a zigzag line, and the lengthwise direction of said light source is aligned vertically in relation to the reference plane RE.

Fourier transformation spectrometer,
where in the field of the measured object 10, 101, 11, 14, 15, 19 and the field of the light source 40, 44, 46, 47, 48, 49 are at least in a partial region arranged optically conjugated in relation to each other.

Fourier transformation spectrometer,
wherein the Michelson-Type Interferometer 601 is formed as an air type or a prism type, or as a hybrid air-prism arrangement.

Fourier transformation spectrometer,
wherein a confocal arrangement 751 is arranged upstream of the Michelson-Type Interferometer 608, 609.

Fourier transformation spectrometer,
wherein the confocal arrangement 751 is formed with a rigid aperture disk 794 or a rotating aperture disk 797.

Fourier transformation spectrometer,
wherein the confocal arrangement 751 is formed with a spatial light modulator in reflection or transmission.

Fourier transformation spectrometer,
wherein the confocal discriminator elements 795, 798 of a confocal arrangement 751 are at least approximately optically conjugated with at least one effective mirror surface in the arm of a Michelson-Type Interferometer 608, 609.

Fourier transformation spectrometer,
wherein at least one field of view discriminator BFD is formed in the Michelson-Type Interferometer 605, 607 as a controllable spatial light modulator in reflection 654, 655, 681, Fourier transformation spectrometer,
wherein at least one field of view discriminator is formed in the Fourier transformation spectrometer system 20 as a controllable spatial light modulator in transmission 79.

Fourier transformation spectrometer,
wherein motion devices in the depth axis are mapped to the measured object 10, 101, 15 or to the mobile measurement head 30, 301 or to a component of the mobile measurement head 30, 301.

| Reference symbol list with explanations | |
|---|---|
| Reference symbols | Identifier |
| 1 | Back of an older patient subject to diagnosis |
| 10 | Biological measured object |
| 101 | Biological measured object with fluorescent markers |
| 11 | Skin feature that from a medical point of view must be carefully examined as it can either be a birthmark or a melanoma. |
| 12 | High risk region, highlighted in color on the monitor Following analysis of the spectral data, the risk level can be determined by artificial intelligence. |
| 13 | Region on the back 1 recorded by means of a spectrometer scan |
| 14 | Measured object for incident light measurement |
| 15 | Partially transparent measured object for a transmitted light measurement |
| 16 | Hot, flowing exhaust cloud in the distance as measured object |
| 17 | Inaccessible organic measured object at medium distance that is emitting thermal radiation |
| 18 | Jet engine flame as measured object |
| 19 | Tissue on the open body of a patient under the conditions of a surgical procedure |
| 20 | Fourier transformation spectrometer system |
| 21 | Computer system for controlling the components, such as the light source and raster detector, and with a computer program for analyzing the spatial interferograms ri and with calculation of spectrums |
| 22 | Analysis program for calculated spectrums, also in order to localize high-risk regions for a melanoma during the medical examination |
| 23 | Monitor for rendering the analyzed data |
| 25 | Control and synchronization devices for the computer-controlled drivers 26 and 27 |
| 26 | Computer-controlled driver with synchronization devices for a digital micro-mirror array 654 that operates synchronized to the digital micro-mirror array 655 |
| 27 | Computer-controlled driver with synchronization devices for the digital micro-mirror array 655 that operates synchronized to the digital micro-mirror array 654 |
| 28 | Datalink to databases |
| 30 | Mobile measurement head |
| 301 | Miniaturized mobile measurement head on the robot arm as a hyperspectral diagnostic instrument |
| 31 | Handle of the mobile measurement head 30 |
| 32 | Start button for recording data |
| 40 | Pulsed striped light source in the NIR range |
| 41 | Light source driver |

-continued

| Reference symbols | Identifier |
| --- | --- |
| 42 | Datalink |
| 43 | Pulsed striped light source, controllable by the computer 21, whose light is coaxially coupled into the illumination beam path by a coupling beam splitter cube 57 |
| 44 | Pulsed UV light source with integrated beamforming optics for projecting a light stripe 802 onto a rigid aperture disk 794 |
| 45 | Imaging optics for a light source for generating structured light |
| 46 | Light source for generating structured light with integrated imaging optics for stripe-shaped object illumination for a transmission measurement |
| 47 | Computer-controlled stripe light source with an OLED array 48, synchronized with a liquid crystal display 79 |
| 48 | OLED array as light source |
| 49 | External fiber coupled cold light source in the near infrared spectral range with beamforming optics for illuminating a rotating aperture disk 797 with pinholes 798 with a light stripe 803 |
| 491 | Beam forming optics for illuminating a rotating aperture disk 797 with a light stripe 803 |
| 50 | Optics unit of the mobile measurement head 30 with a Michelson-Type Interferometer with a lens arranged downstream thereof at the output thereof and a raster matrix detector for detecting spatial interferograms rI. |
| 51 | Anamorphic and largely achromatic lens arranged downstream of the Michelson-Type Interferometer in order to generate interfering cylindrical waves tilted toward each other on a raster detector of coherent image points of a measured object. |
| 511 | Rotational component of the anamorphic lens 51 |
| 512 | Cylindrical component of the anamorphic lens 51 |
| 52 | Anamorphic lens also formed with cylindrical component for the MIR-CaF2 spectral range, which principally corresponds to the optical overall function of the lens 51. |
| 53 | Anamorphic mirror lens with cylindrical mirror for the MIR-KBr spectral range, which principally corresponds to the optical overall function of the lens 51. |
| 537 | Anamorphic mirror lens, consisting of the three reflective free-form surfaces 675, 676, and 677, which principally corresponds to the optical overall function of the lens 51. |
| 54 | InGaAs camera for the near infrared spectral range (NIR) |
| 55 | CMOS camera for the visible spectral range (VIS) |
| 56 | Control link and datalink |
| 57 | Coupling beam splitter cube for light to illuminate a measured object |
| 571 | Coupling beam splitter cube with reflection layer for UV light and with transmission properties of the splitter layer for fluorescent light in the VIS |
| 58 | Bolometer matrix detector |
| 59 | CMOS camera for monitoring for the visible spectral range (VIS) |
| 601 | Michelson-Type Interferometer with lateral shear s |
| 602 | Michelson-Type Interferometer with lateral shear s, which is here formed as a glass block with a triple periscope group 642 that is formed as a prism arrangement in W shape. |
| 603 | Michelson-Type Interferometer with lateral shear s, which is here formed as a glass block with compensation plate 637, a narrow, planar mirror surface 638, and with a triple periscope group 642 that is formed as a prism arrangement in W shape. The Michelson-Type Interferometer 603 has two field of view discriminators in the form of a narrow plane mirror 634 and a planar mirror surface 638. |
| 604 | Michelson-Type Interferometer with lateral shear s, which is here formed as a glass block with compensation plate 632 and with a linear planar end mirror 633, and with a triple periscope group 643 in throat shape. |
| 605 | Michelson-Type Interferometer with lateral shear s with two triple periscope groups 652 and 653 in air, and respectively with one digital micro-mirror array 654 and 655 |
| 606 | Michelson-Type Interferometer with lateral shear s for the FIR with foil beam splitter |
| 607 | Michelson-Type Interferometer with lateral shear s for the MIR spectral range with CaF2 substrates for the beam splitter |
| 608 | Michelson-Type Interferometer with lateral shear s for the MIR with plate beam splitter made of KBr and passive end reflectors 678 and 679, but without field of view discriminators in the interferometer |
| 609 | Michelson-Type Interferometer with lateral shear s, which is formed here as a glass block with compensation plate 637 - like the Michelson-Type Interferometer 603, but without field of view discriminators - and with a triple periscope group 642 in W shape. In place of the narrow |

-continued

| Reference symbols | Identifier |
|---|---|
| | plane mirror 634 and the narrow, planar mirror surface 638 in the Michelson-Type Interferometer 603, slightly wider plane mirrors are inserted in their place in the Michelson-Type Interferometer 609, which is not shown separately here. There is then essentially no field of view discrimination in the Michelson-Type Interferometer 609 itself. |
| 62 | Planar beam splitter layer |
| 621 | Beam splitter block |
| 622 | Beam splitter cube |
| 623 | Mylar foil as beam splitter that represents the beam splitter surface |
| 624 | Beam splitter plate made of CaF2 |
| 625 | Planar beam splitter layer for the MIR range, formed here specifically for the wave number range 4000 $cm^{-1}$ to 1200 $cm^{-1}$ |
| 626 | Compensation plate made of CaF2 |
| 627 | Beam splitter plate made of KBr |
| 628 | Planar beam splitter layer for the long-wave MIR range, formed here specifically for the wave number range 4000 $cm^{-1}$ to 400 $cm^{-1}$ |
| 629 | Compensation plate made of KBr |
| 632 | Mirror plate with adjusted thickness with reflective rear side in the arm of the Michelson-Type Interferometer The thickness of the mirror plate is adjusted for matching the optical distance. |
| 633 | Linear planar end mirror, represents a first field of view discriminator BFD1 |
| 634 | Narrow plane mirror in a triple periscope group<br>This represents a second field of view discriminator BFD2. |
| 635 | Linear mirror in a triple periscope group in throat shape 643<br>This linear mirror represents a second field of view discriminator BFD2. |
| 637 | Compensation plate with narrow, planar mirror surface 638 |
| 638 | Narrow, planar mirror surface<br>This narrow mirror surface represents an end mirror surface and a first field of view discriminator BFD1. |
| 639 | Cover plate made of glass |
| 640 | (2n + 1)-fold periscope group, with n = 1, 2, 3, . . .<br>A (2n + 1)-fold periscope group consists of an arrangement of in total (2n + 1) planar mirrors or planar mirror surfaces in throat or W shape or in a mixed shape, and respectively with angles in relation to each other that are aligned vertically in relation to a common reference plane RE. In the Michelson-Type Interferometer, this periscope group respectively represents an end mirror arrangement.<br>The (2n + 1)-fold periscope group is in this case formed and arranged such that the angle of incidence of the main beam of a partial beam in the Michelson-Type Interferometer on one of the planar mirrors or on one of the planar mirror surfaces is in this case generally larger than two degrees. |
| 641 | Triple periscope group<br>A triple periscope group consists of an arrangement of in total three planar mirrors or planar mirror surfaces in throat or W shape or in a mixed shape, and respectively with angles in relation to each other wherein the planar mirrors or planar mirror surfaces are aligned vertically in relation to a common reference plane RE. In the Michelson-Type Interferometer, the triple periscope group respectively represents an end mirror arrangement.<br>The triple periscope group is in this case formed and arranged such that the angle of incidence of the main beam of a partial beam in the Michelson-Type Interferometer on one of planar mirrors or one of the planar mirror surfaces in this case is generally larger than two degrees, wherein the aperture angle of the partial beam is generally smaller than the angle of incidence of the main beam; there is then under no circumstances a vertical incidence of rays onto one of the planar mirrors or one the planar mirror surfaces. |
| 642 | Triple periscope group, formed as a prism arrangement in W shape according to the definition for a triple periscope group 641. |
| 643 | Triple periscope group, formed as a prism arrangement in throat shape according to the definition for a triple periscope group 641. |
| 644 | Triple periscope group in metal, formed as an arrangement in throat shape and in air according to the definition for 641 |
| 645 | Metal base body with periscope group |
| 645-1 | Metal base body in the first arm IA1 of a Michelson-Type Interferometer |
| 645-2 | Metal base body in the second arm IA2 of a Michelson-Type Interferometer |
| 646 | Relief that is advantageous for technical manufacturing reasons |
| 647 | First plane mirror |
| 648 | Second plane mirror, formed narrow |
| 649 | Third plane mirror |

-continued

| Reference symbols | Identifier |
| --- | --- |
| 650 | Bare surface |
| 651 | Bare surface |
| 652 | Triple periscope group in a metal block 645-1, formed as an arrangement in throat shape and in air according to the definition for 641.<br>A mirror surface is formed by a digital micro-mirror array 654. |
| 653 | Second periscope group in a metal block 645-2, formed as an arrangement in throat shape and in air according to the definition for 641.<br>A mirror surface is formed by a digital micro-mirror array 655. |
| 654 | Digital micro-mirror array (or digital micro-mirror device, DMD)<br>This digital micro-mirror array - with the micro mirrors selecting the light by programming - represents the first field of view discriminator BFD1 in the Michelson-Type Interferometer 605. |
| 655 | Second digital micro-mirror array (DMD)<br>This digital micro-mirror array - with the micro mirrors selecting the light by programming - represents the second field of view discriminator BFD2 in the Michelson-Type Interferometer 605. |
| 656 | Total region used for field of view discrimination on a digital micro-mirror array 654 |
| 657 | Total region used for field of view discrimination on the second digital micro-mirror array 655 |
| 658 | Reflective, preprogrammed region for field of view discrimination on a digital micro-mirror array 654<br>This reflective region selects the light that is ultimately detected and can be incrementally shifted laterally by computer control. |
| 659 | Reflective, preprogrammed region for field of view discrimination on the second digital micro-mirror array 655<br>This reflective region selects the light that is ultimately detected and can be incrementally shifted laterally by computer control, synchronized to the reflective region 658 of the digital micro-mirror array 654. |
| 660 | Device holding the digital micro-mirror array 655 in a fixed position |
| 661a, 661b | Individual micro-mirrors of the digital micro-mirror array 655 |
| 662 | Assembled asymmetric triple periscope group according to the definition for 641, formed as an arrangement in W shape, in air, and with gap-shaped shading aperture 666 and gap 667 of the latter |
| 663 | First gold-plated plane mirror of the triple periscope group 662 |
| 664 | Second gold-plated plane mirror of the triple periscope group 662 |
| 665 | Third gold-plated plane mirror of the triple periscope group 662 |
| 666 | Gap-shaped shading aperture, |
| 667 | Gap of the shading aperture 666 |
| 670 | Arrangement with mirror optics and with a Michelson-Type Interferometer 606 for measuring at a distance in the far infrared spectral range (FIR) |
| 671 | Mirror block with two reflective free-form surfaces (672 and 676) and for the far infrared spectral range (FIR) |
| 672 | Reflective free-form surface on the mirror block 671 |
| 673 | Mirror block with three reflective free-form surfaces (674, 675, and 677) and for the far infrared spectral range (FIR) |
| 674 | Second reflective free-form surface, first reflective surface on the mirror block 673 |
| 675 | Second reflective free-form surface on the mirror block 673 |
| 676 | Reflective free-form surface in saddle shape on the mirror block 671 |
| 677 | Third reflective free-form surface on the mirror block 673 for coupling out for purposes of detecting the spatial interferograms ri |
| 678 | Assembled symmetric triple periscope group according to the definition for 641, formed as an arrangement in W shape and in air for the MIR or FIR spectral range with three gold-plated plane mirrors 678-1, 678-2 and 678-3 |
| 678-1 | First gold-plated plane mirror for the MIR or FIR spectral range |
| 678-2 | Narrow second gold-plated plane mirror for the MIR or FIR spectral range<br>The latter acts as a field of view discriminator. |
| 678-3 | Third gold-plated plane mirror for the MIR or FIR spectral range |
| 679 | Gold-plated plane mirror for the MIR or FIR spectral range<br>This gold-plated plane mirror is the only end mirror in the interferometer arm IA1 and which acts as a field of view discriminator |
| 680 | Reflector block for the MIR spectral range, formed with a triple periscope group with the plane mirrors 683 and 684 and a digital micro-mirror array 682 |
| 681 | First digital micro-mirror array with gold plating of the micro mirrors for the MIR spectral range in the Michelson-Type Interferometer 607<br>This digital micro-mirror array 681 represents an end mirror in the Michelson-Type Interferometer 607 and - with the micro mirrors |

-continued

| Reference symbols | Identifier |
|---|---|
| | selecting the light by programming - at the same time also represents the first field of view discriminator BFD1. |
| 682 | Second digital micro-mirror array with gold plating of the micro mirrors for the MIR spectral range in the reflector block 680 in the Michelson-Type Interferometer 607<br>This digital micro-mirror array 682 in the Michelson-Type Interferometer 607 - with the micro mirrors selecting the light by programming - at the same time also represents the second field of view discriminator BFD2. |
| 683 | First mirror in the reflector block 680 |
| 684 | Third mirror in the reflector block 680 |
| 685 | Cylindrical wavefronts |
| 686 | Peak lines of cylindrical wavefronts tilted toward each other |
| 70 | Upstream lens as focusing imaging system with the optical axis OAI at the input of the Michelson-Type Interferometer 601, which generates focused input beams for the Michelson-Type Interferometer 601.<br>The upstream lens 70 has an autofocus function. |
| 71 | Upstream lens as focusing imaging system with the optical axis OAI on the input of the Michelson-Type Interferometer 602 and with a telecentric aperture 72 in the common focal plane of the individual lenses.<br>The upstream lens is therefore telecentric on both sides and generates focused input beams for the Michelson-Type Interferometer 602. |
| 72 | Telecentric aperture |
| 73 | Upstream lens as focusing imaging system with the optical axis OAI for the MIR spectral range with CaF2 substrates, which generates focused input beams for the Michelson-Type Interferometer. |
| 75 | Two-stage upstream lens as focusing imaging system with the optical axis OAI for the midinfrared spectral range (MIR), which is formed with an integrated field of view discriminator.<br>It generates focused input beams for the Michelson-Type Interferometer. |
| 751 | Confocal arrangement with an upstream focusing lens 781 arranged upstream of the Michelson-Type Interferometer 603, the lens 781 having the optical axis OAI and generating focused input beams for the Michelson-Type Interferometer. |
| 752 | Upstream lens as focusing imaging system, formed from the free-form surfaces 672 and 674 and with the optical axis OAI.<br>These free-form surfaces 672 and 674 generate focused input beams for the Michelson-Type Interferometer 606, and are arranged upstream of the latter. |
| 76 | First lens of an upstream two-stage lens 75 |
| 761 | First assembled lens in a confocal arrangement 751 with coupling beam splitter cube 57 mapped thereto. |
| 762 | First lens with a confocal arrangement 751 that is formed as a microscope lens |
| 763 | First assembled microscope lens stage in a confocal arrangement 751 |
| 77 | Elongated gap aperture discriminator |
| 78 | Second lens of an upstream two-stage lens 75, which itself represents the upstream lens with the optical axis OAI and that generates focused input beams for the Michelson-Type Interferometer. |
| 781 | Second assembled lens with the optical axis OAI in a confocal arrangement 751, which generates focused input beams for the Michelson-Type Interferometer 603 and therefore represents an upstream lens. |
| 79 | Liquid crystal display (LCD) as a controllable field of view discriminator in the image plane BEI |
| 791 | Narrow pass-through area embedded/programmed into the liquid crystal display (LCD) 79 |
| 792-1 | Image of the embedded/preprogrammed narrow pass-through area 791 in the first interferometer arm IA1 |
| 792-2 | Image of the embedded/preprogrammed narrow pass-through area 791 in the second interferometer arm IA2 |
| 794 | Rigid aperture disk with a pinhole pattern |
| 795 | Illuminated pinhole pattern in a zigzag arrangement of pinholes |
| 796 | Image of the illuminated pinhole pattern |
| 797 | Rotating aperture disk with pinholes |
| 798 | Pinholes arranged on a circular ring |
| 799 | Images of illuminated pinholes arranged on a circular ring |
| 80 | Light stripe that is projected and slightly over-sized in the height and length so that the measurement field is generally fully illuminated. |
| 801 | Lightstripe<br>that is projected onto a partially transparent measured object 15 using an NIR stripe light source. |

-continued

| Reference symbols | Identifier |
|---|---|
| 802 | Stripes of ultraviolet light projected onto a rigid aperture disk 794 with a pinhole pattern 795 |
| 803 | Light stripes projected onto a rotating aperture disk 797 with pinholes 798 of which several are illuminated |
| 81 | Measurementfield recorded at a time tl |
| 82 | Measurement field with a moving measured object recorded by a stationary measurement head at time tl, for example a drifting exhaust cloud |
| 83 | Measurement field with illumination using pinhole images, that is recorded at a time t1. |
| 90 | Transport carriage for y scan by the optics unit 50 of the mobile measurement head 30 without illustration of the computer-controllable drive |
| 91 | 2D mirror scanner |
| 92 | Tilted CaF2 plate for compensating astigmatism |
| 93 | Coupling out beam splitter layer for monitoring |
| 94 | CaF2 plate arranged vertically in relation to the axis for compensating the opening error that is corrected in the upstream lens 92 |
| 95 | Tilted CaF2 plate for compensating astigmatism |
| 96 | 5-axis robot arm for precision-guiding the measurement head |
| 97 | Safety window, transparent for the near infrared spectral range (NIR) |
| 98 | Transport carriage for y scan of a measured object |
| 99 | Blocking filter for ultraviolet light |
| AHS | Output main beam |
| alpha | Aperture angle, equivalent to half the opening angle |
| b | Width of the two field of view discriminators BFD1 and BFD2, which is at least approximately equal. |
| b' | Width of the lateral measured object increment as a reverse image of the two field of view discriminators BFD1 and BFD2 |
| b" | Approximate width of the lateral measured object increment as an unfocused reverse image of the width b of the two field of view discriminators BFD1 and BFD2 |
| BEI1 | Image plane in the interferometer arm IA1 in which the field of view discriminator BFD1 is located. The image plane BEI1 and the image plane BEI2 are at least approximately optically conjugated. |
| BEI2 | Image plane in the interferometer arm IA2 in which the field of view discriminator BFD2 is located |
| BEvo | Image plane upstream of the Michelson-Type Interferometer, in which a field of view discrimination is performed |
| BFD1's | Apparent image of the first field of view discriminator BFD1 in the apparent image plane SBE12 |
| BFD1 | First field of view discriminator. The field of view discriminator BFD1 is mapped to the image plane BEI1. A field of view discriminator can for example be a gap aperture, a pinhole array, a pass-through area of a liquid crystal display or a narrow reflective region on a mirror or on a micro-mirror array. A field of view discriminator has a nondiscriminating, or a selecting, region formed for example as a fine aperture opening to allow light to pass through, or a reflecting region, wherein only the selected light is ultimately detected. |
| BFD2's | Apparent image of the second field of view discriminator BFD2 in the apparent image plane SBE12 |
| BFD2 | Second field of view discriminator, also refer to BFD1. The field of view discriminator BFD2 is mapped to the image plane BEI2. |
| BFD1'r | Real reverse-imaged of the first field of view discriminator BFD1 on the measured object. The real images BFD1'r and BFD2'r coincide in the adjusted state of the Michelson-Type Interferometer. |
| BFD2'r | Real reverse-imaged image of the second field of view discriminator BFD2 on the measured object |
| BTB | Laterally limited partial image beam. The latter is formed both by beam splitting and also by limiting using laterally limited optical devices, for example the latter using a gap aperture, a stripe mirror, or a narrow mirror. |
| C | Point on a selected pinhole of an aperture disk 794 or 797 |
| C' | Real image point of the point C on a measured object |
| C" | Real image of the image point C' on the aperture disk 794 or 797 |
| C'''1s | Apparent image point in the first interferometer arm IA1 after unfolding the beam path. This apparent image point C'''1e is optically conjugated in relation to a real image point O"1 of a measured object, and coincides with the |

-continued

| Reference symbols | Identifier |
|---|---|
| | apparent image point O"1s, symbolically represented in the FIGS. 19 and 20. |
| C'''2s | Apparent image point in the second interferometer arm IA2 after unfolding the beam path<br>This apparent image point C'''2e is optically conjugated in relation to a real image point O"2 of a measured object, and coincides with the apparent image point O"2s, symbolically represented in the FIGS. 19 and 20. |
| delta_beta | Angle between interfering wavefronts |
| sS | Sum of the lateral shear for two periscope groups |
| sD | Difference of the lateral shear for two periscope groups |
| DE | Detection plane at the output of the Michelson-Type Interferometer |
| EB | Input beam that is generally a focused beam<br>However, a plurality of beams, one for each recorded object point, exist on the input of the Michelson-Type Interferometer, so that an image can be generated. However, the figures respectively only show an exemplary single input beam that originates from a single object point. |
| Effective mirror surface of a Michelson-Type Interferometer | The effective mirror surface of a Michelson-Type Interferometer is represented in an interferometer arm with only one end mirror by a real mirror surface of said end mirror, which is a real mirror surface RSF. By contrast, in a Michelson-Type Interferometer with three or more than three mirror surfaces in an interferometer arm, which represent a mirror group, the effective mirror surface is generally represented by an apparent end mirror surface SEF that results by unfolding the mirror group. An apparent end mirror surface SEF only exists when more than a single end mirror is located in an arm of the Michelson-Type Interferometer. This is generally the case for a triple periscope or for a $(2n + 1)$-fold periscope group with $n = 2, 3, \ldots$ in the arm of a Michelson-Type Interferometer. |
| Effective mirror tilt in the Michelson-Type Interferometer | The effective mirror tilt alpha_SMI in the Michelson-Type Interferometer is created after unfolding the Michelson-Type Interferometer as the residual tilt of the two effective end mirror surfaces, which in turn can either be real or also apparent. The heavy beams of the two partial beams TB1 and TB2 at the output of the Michelson-Type Interferometer are then at all times tilted toward each other by the angle 2*alpha_SMI. alpha_SMI is equal to zero on an ideally adjusted Michelson-Type Interferometer. |
| EHS | Input main beam |
| End reflector | An end reflector can also be formed as a single mirror, preferably as a plane mirror, but can also represent an arrangement with several mirrors. |
| F511<br>(F521, F531) | Front focal point of the lens 511 in the downstream anamorphic lens 51 (52, 53) in the yz plane, which represents the reference plane RE |
| F'511<br>(F'521, F'531) | Rear focal point of the lens 511 in the downstream anamorphic lens 51 (52, 53) in the yz plane, which represents the reference plane RE |
| f511<br>(f521, f531) | Rear focal length of the lens 511 (521, 531, 581, 591) in the downstream anamorphic lens 51 (52, 53, 58, 59)<br>f511 = f51yz applies.<br>(f521 = f52yz, f531 = f53yz) |
| F51xz<br>(F52xz, F53xz) | Front focal point of the anamorphic lens 51 (52, 53) in the xz plane |
| F'51xz<br>(F'52xz, F'53xz) | Rear focal point of the anamorphic lens 51 (52, 53, 58, 59) in the xz plane<br>F'511 = F'51yz applies.<br>(F'521 = F'52yz, F'531 = F'53yz) |
| F51yz<br>(F52yz, F53yz) | Front focal point of the anamorphic lens 51 (52, 53) in the yz plane, which represents the reference plane RE<br>F511 = F51yz applies.<br>(F521 = F52yz, F531 = F53yz) |
| F'51yz<br>(F'52yz, F'53yz) | Rear focal point of the anamorphic lens 51 (52, 53) in the yz plane, which represents the reference plane RE |
| FFT | Fast Fourier Transformation, an effective algorithm used for calculating a spectrum from an interferogram |
| FIR | Far infrared spectral range |
| Michelson-Type Interferometer | On a Michelson-Type Interferometer, the outbound and the return beam in each arm of the latter are at least approximately parallel. The real mirror surface (RSF), represented by a single plane mirror in an interferometer arm or the apparent end mirror surface (SEF) in a multi-mirror arrangement in an interferometer arm are generally arranged at least approximately vertically in relation to the reference plane RE. In a Michelson-Type Interferometer, the partial beams TB1 and TB2 are at least approximately vertically incident onto a mirror surface (RSF) or an apparent end mirror surface (SEF). |
| MIR | Midinfrared spectral range |
| NIR | Far infrared spectral range |

-continued

| Reference symbols | Identifier |
|---|---|
| | Reference symbol list with explanations |
| NT | Normal of the beam splitter plane, which together with the optical axis OAI spans the reference plane RE.<br>The beam splitter plane is represented by a beam splitter layer 62 or by a mylar foil 623, or by a lattice. |
| O | Illuminated or self-luminescent object point on the measured object |
| O' | Real image point of the object point O |
| O'1 | Real image point of the object point O in the first interferometer arm IA1 |
| O'1s | The apparent image point of the object point O after onetime imaging O'1s is mapped to the first arm IA1 of the Michelson-Type Interferometer.<br>The apparent image point O'1s is located in the apparent image plane SBE1 and - given sufficiently precise adjustment of the Michelson-Type Interferometer - is also located in the apparent image plane SBE12 upstream of the anamorphic lens 51 (52, 53, 537).<br>For apparent image points located along the depth axis, shifts along the depth axis due to refractive materials must also be taken into account if present. |
| O"1s | Completely unfolded, and therefore apparent image point of the object point O upstream of the anamorphic lens 51 that originates from the first arm IA1 of the Michelson-Type Interferometer, given a two-stage upstream lens 74 or a confocal arrangement 751. |
| O'1-unfocused | Unfocused image spot of the object point 0 in the first interferometer arm IA1 due to astigmatism |
| O'2 | Real image point of the object point O in the second interferometer arm IA2 |
| O'2s | Apparent image point of the object point O after one time imaging, which is mapped to the second arm IA2 of the Michelson-Type Interferometer.<br>The apparent image point O'2s is located in the apparent image plane SBE2 and - given sufficiently precise adjustment of the Michelson-Type Interferometer - is also located in the apparent image plane SBE12 upstream of the anamorphic lens 51 (52, 53, 537).<br>For apparent image points located along the depth axis, shifts along the axis due to refractive materials must also be taken into account if present, for example given the presence of a beam splitter cube in the interferometer made of optical glass. |
| O"2s | Apparent image point of the object point O upstream of the anamorphic lens 51 that originates from the second arm IA2 of the Michelson-Type Interferometer, given a two-stage upstream lens 74 or a confocal arrangement 751. |
| O"2-unfocused | Unfocused image spot of the object point O in the second interferometer arm IA2 due to astigmatism |
| O'''2-unfocused | Unfocused image spot of the object point O in the second interferometer arm IA2 due to astigmatism |
| O'1e | Unfolded image point of the object point O after unfolding the first interferometer arm IA1 in the apparent end mirror surface SEF1.<br>O"1e and O"2e represent coherent light source points. |
| O'2e | Unfolded image point of the object point O after unfolding the second interferometer arm IA2 in the apparent end mirror surface SEF2, given field of view discrimination in the Michelson-Type Interferometer |
| O" | Image point of the object point O after two-time imaging |
| O"1 _xz | Image point of the object point O on the raster detector in the xz plane |
| O'''1s | Apparent image point of the object point O in the apparent image plane SBE1 after unfolding the first interferometer arm IAl, for example in a confocal arrangement 751 (in FIG. 18), given a field of view discrimination upstream of the Michelson-Type Interferometer |
| O'''2s | Apparent image point of the object point O in the apparent image plane SBE2 after unfolding the second interferometer arm IA2, for example in a confocal arrangement 751 (in FIG. 18), given a field of view discrimination upstream of the Michelson-Type Interferometer |
| OAI | Optical axis of the upstream lens 70, 71, 73, 752, 78, 781, 752, which generally faces the [ . . . ] IA2 of the Michelson-Type Interferometer<br>In the unfolded state of the arrangement, the optical axis OAI coincides with the z axis. |
| P | Point on a liquid crystal display (LCD) 79, for example on a pixel of the latter |
| OE | Object element<br>The object elements OE_1, OE_2 . . . OE_n are arranged in x direction, which then form a stripe-shaped measurement field. |
| P' | Image of the point P after imaging by the first lens 761 |
| P" | Image of the point P after imaging by the second lens 781 |
| P'''1s | Apparent image point of the point P in the apparent image plane SBE12 after unfolding the first interferometer arm IA1 |

-continued

| Reference symbols | Identifier |
|---|---|
| | The apparent image point P'''1s (here in FIG. 18) coincides with an apparent image point O''1s. |
| P'''2s | Apparent image point of the point P in the apparent image plane SBE12 after unfolding the second interferometer arm IA2<br>The apparent image point P'''2s (here in FIG. 18) coincides with an apparent image point O''2s. |
| RE | Reference plane spanned by the optical axis OAI of the lens (70, 71, 73, 75, 781, 752) arranged upstream of the Michelson-Type Interferometer and by the normal of the planar beam splitter layer 62, 625, 628 or the mylar foil 623.<br>The raster detector is in a standard case vertical in relation to the reference plane RE. |
| rI | Spatial interferogram |
| RSF | Real mirror surface<br>The real mirror surface is in this case generally represented in the first interferometer arm IA1 and is an end mirror surface. This real mirror surface is coincidental with a real planar end mirror 633, 638, 679 or also with the digital micro-mirror array 681 if the latter is inserted as an end mirror. |
| RZ | Radius of a cylindrical wave, which becomes very small or approaches zero on the raster detector |
| s | Lateral shear after passing a (2n + 1)-fold periscope group with n = 1, 2, 3 - as described above - for the case that only a single (2n + 1)-fold periscope group is arranged in the interferometer. The lateral shear represents the lateral shift of coherent image points. |
| s1 | Lateral shear after passing a first (2n + 1)-fold periscope group with n = 1, 2, 3 - as described above |
| s2 | Lateral shear after passing a second (2n + 1)-fold periscope group with n = 1, 2, 3 - as described above |
| SBE1 | Apparent image plane of the anamorphic lens 51 (52, 53, 537) from the interferometer arm IA1 with the apparent image point O'1s, where appropriate, respectively also O''1s, where appropriate, respectively also C'''1s, and where appropriate respectively also P'''1s |
| SBE2 | Apparent image plane of the anamorphic lens 51 (52, 53, 537) from the interferometer arm IA2 with the apparent image point O'2s, where appropriate, respectively also O''2s, where appropriate, respectively also C'''2s, and where appropriate respectively also P'''2s.<br>The two apparent image planes SBE1 and SBE2, which have the same position along the depth axis, also lie in the apparent image plane SBE12, given sufficiently precise adjustment of the Michelson-Type Interferometer. |
| SBE12 | Apparent image plane upstream of the anamorphic lens 51 (52, 53, 537) with the apparent image points O'1s and O'2s<br>The two apparent image planes SBE1 and SBE2, which have the same position along the depth axis, also lie in the apparent image plane SBE12. The apparent image plane SBE12 and also the two apparent image planes SBE1 and SBE2 are shown together in FIG. 5 and in the FIGS. 13 and 14.<br>(the illustration of the two apparent image planes SBE1 and SBE2 was omitted in the remaining figures, and only the apparent image plane SBE12 is shown.)<br>The apparent image points of objects separated by the lateral shear s, here for example the image points O'1s and O'2s and also O''1s and O''2s, also lie in the apparent image plane SBE12. The apparent image points (O'1s and O'2s and also O''1s and O''2s) are respectively coherent and are therefore capable of interference. Image points (C'''1s and C'''2s in FIG. 18 and 19 and also P'''1s and P'''2s in FIG. 18) of the points C and P are likewise separated in the apparent image plane SBE12 with the lateral shear s.<br>As is already known, a common position along the depth axis of the two apparent image planes SBE1 and SBE2 in the depth axis, which justifies the model of an apparent image plane SBE12, in addition to balancing (matching the position along the depth axis) the interferometer does however also imply a sufficiently precise angular adjustment of the Michelson-Type Interferometer. This means that the selected wave fronts directly at the output of the Michelson-Type Interferometer and upstream of the anamorphic lens (51, 52, 53, 537), which belong to the two selected partial beams, are tilted toward each other by no more than one half wavelength. The value "half wavelength" refers to the lateral expansion of these wavefronts in a direction parallel in relation to the reference plane RE and laterally in relation to the direction of light propagation, thus resulting in the tilt angle between the wavefronts. The tilt axis in this case is arranged vertically in relation to the reference plane RE. This must be observed for light of the shortest wavelength that is still detected and is therefore |

| Reference symbols | Identifier |
|---|---|
| | used for calculating spectrums. This precise adjustment of the Michelson-Type Interferometer is mandatory for achieving a high contrast of at least 50% when detecting the spatial interferograms, in order to ultimately obtain comparatively low-noise spectrums. Persons skilled in the art of interferometry are broadly familiar with these relationships. This document at all times assumes this sufficiently precise adjusted state of the Michelson-Type Interferometer. |
| SEF1 | Apparent end mirror surface in the first interferometer arm IA1 In the sense of a substitute mirror surface.<br>The apparent end mirror surface SEF1 is determined by the unfolding of a triple periscope group, which is arranged in the first interferometer arm IAl. This also applies for the unfolding of a (2n + 1)-fold periscope group, with n = 1, 2, 3, . . . . |
| SEF2 | Apparent end mirror surface in the second interferometer arm IA2 in the sense of a substitute mirror surface.<br>The apparent end mirror surface SEF2 is determined by the unfolding of a triple periscope group, which is arranged in the second interferometer arm IA2. This also applies for the unfolding of a (2n + 1)-fold periscope group, with n = 1, 2, 3, . . . . |
| Sp | Spectrum that was calculated from a spatial interferogram using FFT |
| TB1 | First partial beam after beam splitting<br>However, there are simultaneously a plurality of partial beams that each originate from an object point. The partial beam TB1 resulting from the object point O and shown in the figures is therefore only representative for a plurality of such partial beams. A partial beam is also mapped to a wavefront, for example at the output of the interferometer. |
| TB2 | Second partial beam after beam splitting<br>However, there are simultaneously a plurality of partial beams that each originate from an object point. The partial beam TB2 resulting from the object point O and shown in the figures is therefore only representative for a plurality of such partial beams. |
| VIS | Visual spectral range |
| x direction | Vertical in relation to the reference plane RE<br>The lengthwise direction of a striped, or the lengthwise direction of a striped light source or also of a gap is parallel in relation to the x direction. |
| y direction | Parallel in relation to the reference plane RE<br>In the unfolded state, the direction of the lateral shear is parallel in relation to the y direction. |
| z direction | Propagation direction of the interference light in detection direction<br>The z direction is parallel in relation to the optical axis OAI. |

The invention claimed is:

1. A Fourier Transformation Spectrometer ("FT spectrometer"), comprising:
a Michelson-Type Interferometer comprising:
at least one beam splitter unit, wherein the beam splitter unit is designed to split an incident light beam of a spatially expanded object into a first partial beam and a second partial beam; and
to at least partially overlay the first partial beam and the second partial beam with a lateral shear s;
a first beam deflection unit designed to deflect the first partial beam at least a first time;
a second beam deflection unit designed to deflect the second partial beam at least a first time;
wherein at least one among the first beam deflection unit and the second beam deflection unit represents a (2n+1) periscope group with (2n+1) mirror surfaces and all (2n+1) mirror surfaces are arranged vertically in relation to a common reference plane, in order to respectively deflect the first partial beam (2n+1) times, and wherein the (2n+1)-fold deflection generates the lateral shear(s) between the first partial beam and the second partial beam, and wherein n is a natural number ≥1;
wherein the FT spectrometer additionally comprises:
at least one lens arranged opposite the beam splitter unit such that the incident light beam passes the lens at least partially before the light beam is split on the beam splitter unit and the first partial beam and the second partial beam respectively generate a plurality of coherent image points of the spatially expanded object in an image plane in light direction downstream of the beam splitter unit and upstream of a detector;
the detector to record a plurality of spatial interferograms on the basis of the spatial overlay of the first partial beam and the second partial beam, which corresponds at least to the partial imaging of the plurality of coherent image points; and
at least one computing unit for the Fourier transformation of the plurality of spatial interferograms to generate a plurality of spectrums, and based thereon, to generate at least a partial area of at least one hyperspectral image of the spatially expanded object.

2. The FT spectrometer according to claim 1, wherein the reference plane is spanned by the normal of the beam splitter unit and by an optical axis of the upstream lens.

3. The FT spectrometer according to claim 1, wherein the (2n+1) periscope group corresponds to a throat or a W shape.

4. The FT spectrometer according to claim 1, wherein each of the mirror surfaces is arranged to reflect the first partial beam or the second partial beam-OB once.

5. The FT spectrometer according to claim 1,
wherein at least one among the first beam deflection unit and the second beam deflection unit is designed to deflect the first partial beam or the second partial beam-OB once through single reflection on a mirror surface of the corresponding beam deflection unit; and/or
wherein at least one among the first beam deflection unit and the second beam deflection unit is designed to deflect the first partial beam or the second partial beam-OB three times through triple reflection on three mirror surfaces of a triple periscope group of the corresponding beam deflection unit.

6. The FT spectrometer according to claim 1, wherein the first beam deflection unit and the second beam deflection unit together have a number of mirror surfaces that either corresponds to $(2n+1+1)$ or $(2n_1+1+2n_2+1)$, and wherein n is a natural number $\geq 1$, $n_1$ is a natural number $\geq 1$ and $n_2$ is a natural number $\geq 1$.

7. The FT spectrometer according to claim 1,
wherein the Michelson-Type Interferometer further comprises at least one field of view discriminator unit arranged downstream of the beam splitter unit in light direction, the field of view discriminator unit arranged such that the first partial beam and/or the second partial beam is spatially selected, and
wherein at least one field of view discriminator unit is arranged between at least two of the $(2n+1)$ mirror surfaces of the $(2n+1)$ periscope group of the at least one beam deflection unit such that the first partial beam and/or the second partial beam is spatially selected.

8. The FT spectrometer according to claim 7, wherein at least one field of view discriminator unit is integrated into one of the mirror surfaces of the first beam deflection unit and/or the second beam deflection unit.

9. The FT spectrometer according to claim 7, wherein the Michelson-Type Interferometer also comprises at least one field of view discriminator unit arranged downstream of the first beam splitter unit in light direction, and a second field of view discriminator unit arranged such that the first partial beam and the second partial beam are spatially selected, and such that the first field overview discriminator unit is optically conjugated in relation to the second field of view discriminator unit.

10. The FT spectrometer according to claim 7, wherein the field of view discriminator unit comprises at least one of the following:
a gap-shaped shading aperture,
a micro-gap shading aperture array,
a pinhole shading aperture,
a one-dimensional or a two-dimensional pinhole shading aperture array in the form of an aperture disk,
a micro-gap shading aperture array with a plurality of micro gaps in a laterally shifted arrangement,
a micro-gap shading aperture array with mechanically movable elements, and
a reflective gap-shaped region that represents a part of the first and/or the second beam deflection unit.

11. The FT spectrometer according to claim 1, wherein at least one of the first beam deflection unit and the second beam deflection unit comprises a prism with at least one reflection surface that is designed to reflect the first partial beam and/or the second partial beam at least once.

12. The FT spectrometer according to claim 1, further comprising a confocal arrangement arranged upstream of the Michelson-Type Interferometer, wherein the confocal arrangement comprises a rigid aperture disk or a rotating aperture disk.

13. The FT spectrometer according to claim 1, wherein the beam splitter unit represents an amplitude beam splitter, and comprises a planar beam splitter layer, a mylar foil, or a lattice.

14. A method for interferometric measurement using an FT spectrometer with a Michelson-Type Interferometer, the method comprising:
splitting an incident light beam transmitted from a spatially expanded object into a first partial beam and a second partial beam using a beam splitter unit;
at least a one-time deflection of the first partial beam using a first beam deflection unit;
at least a one-time deflection of the second partial beam using a second beam deflection unit;
wherein the first partial beam and/or the second partial beam is deflected $(2n+1)$ times on at least either of the first beam deflection unit and the second beam deflection unit, using a $(2n+1)$ periscope group with $(2n+1)$ mirror surfaces in order to generate a lateral shear(s) between the first partial beam and the second partial beam, and wherein n is a natural number $\geq 1$;
sending the incident light beam through a lens prior to the splitting to generate a plurality of coherent image points of the spatially expanded object in an image plane between the beam splitter unit and a detector;
spatially at least partially overlaying the first partial beam and the second partial beam using the beam splitter unit;
at least partially rendering the plurality of coherent image points while at the same time generating a plurality of spatial interferograms on a detector field of the detector on the basis of the spatial overlay;
recording the plurality of spatial interferograms using the detector; and
Fourier transforming the plurality of spatial interferograms to generate a plurality of spectrums, and based thereon,
generating a hyperspectral image of at least a section of the spatially expanded object.

15. The method for interferometric measurement according to claim 14, further comprising the steps initiated and at least partially executed by at least one computer unit:
multiple simultaneous recording of the plurality of spatial interferograms at respectively different points in time;
Fourier transforming the plurality of spatial interferograms recorded at respectively different points in time to generate a plurality of spectrums; and
generating at least one hyperspectral image of the spatially expanded object.

16. The FT spectrometer according to claim 1, further comprising a confocal arrangement arranged upstream of the Michelson-Type Interferometer, wherein the confocal arrangement comprises a spatial light modulator in reflection or transmission.

* * * * *